United States Patent [19]

Strasser et al.

[11] Patent Number: 5,151,354
[45] Date of Patent: Sep. 29, 1992

[54] FERMENTATION PROCESSES USING AMYLOLYTIC ENZYME PRODUCING MICROORGANISMS

[75] Inventors: Alexander Strasser, Dusseldorf; Feodor B. Martens, HE Leiden; Jurgen Dohmen, Meerbushl; Cornelius P. Hollenberg, Chopinstr 7, D-4000 Dusseldorf, all of Fed. Rep. of Germany

[73] Assignee: Cornelius Hollenberg, Dusseldorf, Fed. Rep. of Germany

[21] Appl. No.: 748,161

[22] Filed: Aug. 21, 1991

Related U.S. Application Data

[60] Division of Ser. No. 85,107, Aug. 13, 1987, which is a continuation-in-part of Ser. No. 62,943, Jun. 16, 1987, abandoned.

[30] Foreign Application Priority Data

Aug. 21, 1986 [EP] European Pat. Off. ........... 86111586
Jul. 17, 1987 [EP] European Pat. Off. ........ 87110370.1

[51] Int. Cl.$^5$ ......................... C12P 7/06; C12N 1/19; C12C 11/00; A21D 8/04
[52] U.S. Cl. .................................. 435/161; 435/256; 426/11; 426/16; 426/19; 426/20; 426/29
[58] Field of Search ...................... 435/69.1, 161, 256; 935/59; 426/7, 11, 12, 16, 18, 19, 20, 28, 29

[56] References Cited

U.S. PATENT DOCUMENTS

4,794,175 12/1988 Nunberg et al. .................... 536/27

FOREIGN PATENT DOCUMENTS

0096430 12/1983 European Pat. Off. .
0126206 11/1984 European Pat. Off. .
0163491 12/1985 European Pat. Off. .
0173668 5/1986 European Pat. Off. .
0185327 6/1986 European Pat. Off. .
0260404 3/1988 European Pat. Off. .
0214883 1/1985 New Zealand .
86/07091 5/1986 PCT Int'l Appl. .
86/03778 7/1986 PCT Int'l Appl. .

OTHER PUBLICATIONS

Pretorius, "Molecular Cloning and Characterization of the STA2 Glucoamylase Gene of *S. diastaticus*," Gene, 100:94–100.

Meaden et al, "A Plasmid System for the Genetic Manipulation of Brewing Strains," EBC Congress 1985, pp. 219–226.

Sills et al., "Production of Amylolytic Enzymes by Several Yeast Species," J. Inst. Brew. 88:313–316 (Sep. 1982).

Wilson et al., "Isolation and Characterization of *Schw. alluvius* Amylolytic Enzymes," Applied and Environmental Microbiology, 44(2):301–307 (Aug. 1982).

Frelot et al., "Strain Selection for the Purpose of Alcohol Production from Starch Substrates," Biotechnology Letters, 4(11):705–708 (1982).

(List continued on next page.)

*Primary Examiner*—Richard A. Schwartz
*Assistant Examiner*—Michelle Johnson
*Attorney, Agent, or Firm*—Iver P. Cooper

[57] ABSTRACT

This invention provides a method for producing amylolytic enzymes by culturing a microorganism, having received as a result of recombinant DNA technology DNA sequences from a donor yeast comprising the coding sequences for the amylolytic enzymes wherein the host microorganism is capable of expressing said amylolytic enzymes. Furthermore, this invention provides microorganisms genetically engineered as to being able to produce and express the amylolytic enzymes, a vector containing the DNA sequences, coding for the amylolytic enzymes and the respective DNA sequences. The said host microorganisms are useful in the production of biomass and many fermentation processes, preferably in the production of special beers.

14 Claims, 42 Drawing Sheets

OTHER PUBLICATIONS

Mellor et al., "Factors Affecting Heterologous Gene Expression in *S. cerevisiae*," Gene, 33:215–226 (1985).

Tubb et al., "Constructing Amylolytic Strains of Yeast for Commercial Applications," Proceedings of the AIKO Yeast Symposium 1:229 (1983).

Reipen et al., "Non-Selective Transformation of *S. cerevisiae*," Current Genetics, 6:189–193 (1982).

Pardo et al., "Cloning of the STA2 and SGA Genes Encoding Glucoamylases in Yeasts and Regulation of their Expression by the STAIO Gene of *S. cerevisiae*," Nucleic Acids Research, 14(12):4701–4718 (1986).

Dhawale et al., "Interspecific Protoplast Fusion of Schwanniomyces Yeast," Biotechnology Letters, 5(12):825–830 (1983).

Filho et al., "Stable Yeast Transformants that Secrete Functional α-Amylase Encoded by Cloned Mouse Pancreatic cDNA," Bio/Technology, 4:310–315 (1986).

Panchal et al., "Susceptibility of Saccharomyces spp. and Schwanniomyces spp. to Aminoglycoside Antibiotic G418," Applied and Environmental Microbiology 47(5):1164–66 (1984).

Klebe et al., "A General Method for PEG-Induced Genetic Transformation of Bacteria and Yeast," Gene 25:333–341 (1983).

Rothstein et al., "Secretion of a Wheat α-Amylase Expressed in Yeast," Nature, 308:662–665 (1984).

Yamashita et al., "Secretion of *S. diastaticus* Glucoamylase from *Sch. pombe*," Agric. Biol. Chem., 48(7):1931–1932 (1984).

Yamashita et al., "Cloning and Expression of the *S. fibuligera* α-Amylase Gene in *S. cerevisiae*," Agric. Biol. Chem. 49(10):3089–3091 (1985).

Yamashita et al., "Molecular Cloning of a Glucoamylase-Producing Gene in the Yeast Saccharomyces," Agric. Biol. Chem. 47(11)2689–2692 (1983).

Panchal et al., "Genetic Manipulations of Brewing and Related Yeast Strains," Food Technology pp. 99–106, 111 (Feb. 1984).

Sills et al., "Genetic Manipulation of Amylolytic Enzyme Production by Yeasts," Proceedings of the AIKO Yeast Symposium 1:209–228 (1983).

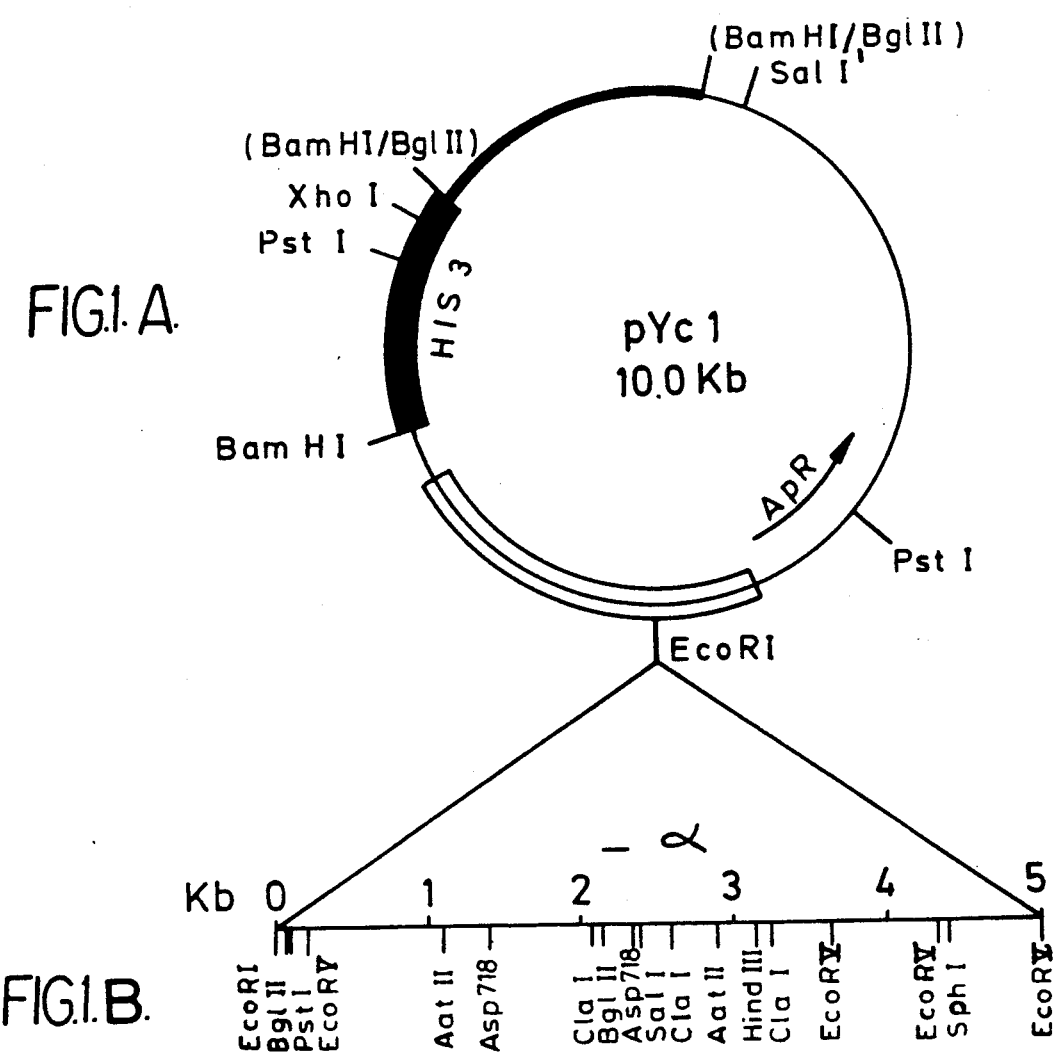
FIG.1.A.
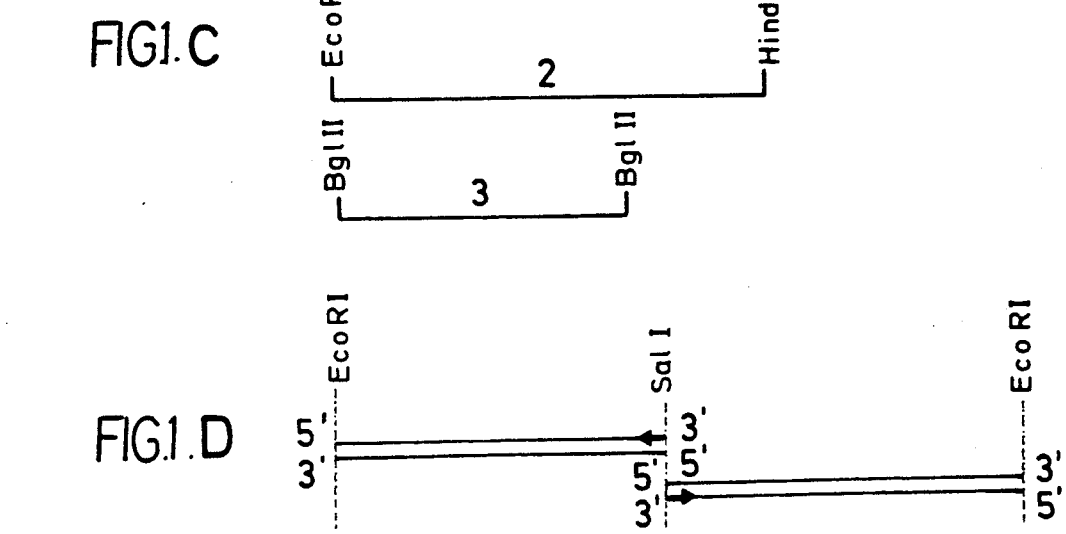
FIG.1.B.
FIG.1.C
FIG.1.D

FIG.2A

```
         10         20         30         40         50         60
GGTACCTGAGCTAAATTTAGAACCGGGCTATAGATCCGCTTGTCTAAAGAAGAGATAATGA 70         80         90        100        110        120
AGAAAACAATTAACCGAGCACTCTTATTAAGTTTTTTCTATTTTCTTTTGCTCCTACTT 130        140        150        160        170        180
CAATAATTTATCTAAATTGTATTGTGCGTTAGATCAGAATGTACTGATAACAGAGAGTAT 190        200        210        220        230        240
TATCATACACTTGTGGATTTCAAAAGGCGGAATCAAAAGCATACGTAGTCAAACCCTTGG 250        260        270        280        290        300
TTATTTGATGCAATTAAGGTTGTAGTCGTTCTTACCGATCCATCATTATACCCCACACGG 310        320        330        340        350        360
TTTCATGGTATGTAGGTGTTTCAATAGTGAAGTACAATGAATGTTTGGTAATGCTGTAT 370        380        390        400        410        420
GTGGATCAGTAATTATGTTAAACAATTAAGTCTGAAAATTATTAAAATTTTACCTACAA 430        440        450        460        470        480
ATTAAGCCGAAATCCAATCGAAGGTGCCGCCCAGCTGGTGTATAAATTACTCTTGAAATT
```

FIG. 2A. CONT.

```
       490         500         510         520         530         540
CAAGTTGAACGTTGATCTCTCTAAAGCAAAGCTGTTATTCTACAATACTAAATAAAATAA 550         560         570         580         590         600
AAGCAAGACATGAGATTTTCAACTGAAGGATTTACAAGTAAAGTTGTTGCAGCAATTTA
              MetArgPheSerThrGluGlyPheThrSerLysValValAlaAlaIleLeu 610         620         630         640         650         660
GCATTCTCAAGATTGGTATCTGCTCAACCGATTATTTTTGACATGAGAGATGTTAGCTCG
AlaPheSerArgLeuValSerAlaGlnProIleIlePheAspMetArgAspValSerSer 670         680         690         700         710         720
TCAGCTGATAAATGGAAAGACCAATCGATTATCAATCGTTACTGATAGGTTTGCCAGA
SerAlaAspLysTrpLysAspGlnSerIleIleTyrGlnIleValThrAspArgPheAlaArg 730         740         750         760         770         780
TCTGATGGCTCGACCACAGCTGACTGTTTAGTGAGTGATCGCAAGTACTGTGGTGGATCT
SerAspGlySerThrThrAlaAspCysLeuValSerAspArgLysTyrCysGlyGlySer 790         800         810         820         830         840
TATAAAGGGATTATCGACAAGTTGGATTATATTCAAGGTATGGGTTTCACTGCGATCTGG
TyrLysGlyIleIleAspLysLeuAspTyrIleGlnGlyMetGlyPheThrAlaIleTrp 850         860         870         880         890         900
ATCTCCCAGTTGTTGAGCAAATTCCTGACAATACTGCTTATGGTTATGCTTACCATGGT
IleSerProValValGluGlnIleProAspAsnThrAlaTyrGlyTyrAlaTyrHisGly
```

FIG 2B

```
           910        920        930        940        950        960
TATTGGATGAAAAATATTGATGAATTGAACACTAATTTTGGTACCGCTGATGAATTGAAA
TyrTrpMetLysAsnIleAspGluLeuAsnThrAsnPheGlyThrAlaAspGluLeuLys 970        980        990       1000       1010       1020
CAATTAGCTAGCGAATTGCATTTCAGAGAAGCATGTATGATGGTCGACGATGTTACAACCAT
GlnLeuAlaSerGluLeuHisPheArgSerMetTyrAspGlyArgArgCysTyrAsnHis 1030       1040       1050       1060       1070       1080
TATGCTTGGAACGGAGATGGTTCAAGCGTAGATTATTCTAGTTTCACTCCATTCAATCAA
TyrAlaTrpAsnGlyAspGlySerValAspTyrSerSerPheThrProPheAsnGln 1090       1100       1110       1120       1130       1140
CAATCTTACTTCCACGATTATTGTTGATTACAAATTATAATGATCAAACCAATGTTGAA
GlnSerTyrPheHisAspTyrCysLeuIleThrAsnTyrAsnAspGlnThrAsnValGlu 1150       1160       1170       1180       1190       1200
GATTGTTGGGAAGGTGATACTGAAGTCTCCCCTTCCAGATTTAAGTACCGAGGATAATGAA
AspCysTrpGluGlyAspThrGluValSerProSerLeuProAspLeuSerThrGluAspAsnGlu 1210       1220       1230       1240       1250       1260
GTTATAGGAGTATTTCAAACTTGGGTGTCAGATTTTGTTCAAAACTATTCAATTCGATGGT
ValIleGlyValPheGlnThrTrpValSerAspPheValGlnAsnTyrSerIleAspGly 1270       1280       1290       1300       1310       1320
TTAAGAATTGATAGTGCAAAGCACGTAGATACCGCTTCATTAACGAAGTTTGAGGACGCT
LeuArgIleAspSerAlaLysHisValAspThrAlaSerLeuThrLysPheGluAspAla
```

FIG.2B. CONT.

```
     1330      1340      1350      1360      1370      1380
TCTGGTGTTTATAACTTAGGTGAAGTTTATCAAGGAGATCCAACTTATACTTGTCCATAT
SerGlyValTyrAsnLeuGlyGluValTyrGlnGlyAspProThrTyrThrCysProTyr 1390      1400      1410      1420      1430      1440
CAGAATTATATGAAAGGAGTTACCAACTATTCCATTATATCCAGTATATAGATTCTTC
GlnAsnTyrMetLysGlyValThrAsnTyrProLeuTyrTyrProValTyrArgPhePhe 1450      1460      1470      1480      1490      1500
AGTGATACTTCGGCGACTTCCAGTGAGTTAACTTCAATGATCTCCACGTTACAGTCATCT
SerAspThrSerAlaThrSerSerGluLeuThrSerMetIleSerThrLeuGlnSerSer 1510      1520      1530      1540      1550      1560
TGTTCGGACGTCTCTTTGTTGGGAAACTTTATTGAAAACCATGACCAAGTTAGATTTCCA
CysSerAspValSerLeuLeuGlyAsnPheIleGluAsnHisAspGlnValArgPhePro 1570      1580      1590      1600      1610      1620
TCAGTTACCTCAGACACATCCTGATTAAGAATGACATGGCTTTTATAATTTTGGGTGAT
SerValThrSerAspThrSerLeuIleLysAsnAspMetAlaPheIleIleLeuGlyAsp 1630      1640      1650      1660      1670      1680
GGTATCCCAATTATTATTGGCCAAGAACAAGGTCTCAATGGTGGTTCCGATCCTGCC
GlyIleProIleIleTyrTyrGlyGlnGluGlnGlyLeuAsnGlyGlySerAspProAla 1690      1700      1710      1720      1730      1740
AATAGAGAAGCTTTATGGTTAAGTGGATATATAACGATTCAGAATACTACGAGCTAATC
AsnArgGluAlaLeuTrpLeuSerGlyTyrAsnThrAspSerGluTyrTyrGluLeuIle 1750      1760      1770      1780      1790      1800
AGTAAACTAAATCAAATCAAGAAATCAAGCTATTAAGAAGGATTCTGCCTATTCAACTTAC
SerLysLeuAsnGlnIleArgAsnGlnAlaIleIleLysLysAspSerAlaTyrSerThrTyr
```

FIG 2C

```
         1810      1820      1830      1840      1850      1860
AAATCCTCAGTTGTTTCTTCTTCAGACCACTATATAGCCACTAGGAAGGGTAGCGATGCT
LysSerSerValValSerSerSerAspHisTyrIleAlaThrArgLysGlySerAspAla 1870      1880      1890      1900      1910      1920
AATCAATTGATTTCCATTTTTAATAATTTAGGTTCAAACGGGTCACAGGATATTACTGTC
AsnGlnLeuIleSerIlePheAsnAsnLeuGlySerAsnGlySerGlnAspIleThrVal 1930      1940      1950      1960      1970      1980
AGCAACACCGGCTATTCTAGTGGTGATAAAGTTATCGATATTATTTCTTGCAATTCCGTT
SerAsnThrGlyTyrSerSerGlyAspLysValIleAspIleIleSerCysAsnSerVal 1990      2000      2010      2020      2030      2040
TTAGCTGGTGACTCCGGAAGCTTATCTGTATCAATTTCTGGTGGAATGCCACAAGTTTAC
LeuAlaGlyAspSerGlySerLeuSerValSerIleSerGlyGlyMetProGlnValTyr 2050      2060      2070      2080      2090      2100
GCTCCGTCCTCTGTTCTTTCGGGATCTGGCATCTGCAATCAATAGATTGATCCAGCGCTA
AlaProSerSerValLeuSerGlySerGlyIleCysAsnGlnEnd 2110      2120      2130      2140      2150      2160
ACCCTTTTTTTAGCAACGACAAGTTTATTTTAGAAAAAGTTTTCTAAGAATGGTCAAAAC 2170      2180      2190      2200      2210      2220
AAGTTCTTATTACTTCTATGTCCCTGGATATCTGTTTTCAATGTTCTCTGACTCCACATT 2230      2240      2250      2260      2270      2280
CCTCATGTTTAGTTCTCTATTTTTTGTCGATCTTCTAAGTTTTTTTATTCTTAATTTTAA

2290
TCCAAAAGTT
```

Peptide 1: GLY-GLY-ASN-VAL-LEU-PRO-THR-GLN-GLU-PRO-GLY-TYR-THR-VAL-
ALA-GLU-SER-ARG Peptide 2: ALA-THR-SER-TYR-PRO-VAL-GLY-PHE-ASP-VAL-SER-CYS-ALA-
SER-GLU-TRP-LYS Peptide 3: GLY-VAL-PHE-PRO-GLY-ALA-GLY-LYS-GLU-GLU-VAL-TYR-TYR-ASP-
TRP-TYR-THR-GLN-ARG Peptide 4: TRP-GLY-TYR-ASP-THR-ILE-GLU-LYS Peptide 5: THR-LEU-PHE-ALA-ASN-ASP-VAL-GLY-ASP-PRO-ILE-ASP-GLY-
ASN-ILE-TYR-GLY-VAL-HIS-PRO-VAL-TYR-LEU-ASP-GLN-ARG

FIG. 3

• — • CELL DENSITY (LOG OD 600)
□ — □ TOTAL α AMYLASE ACTIVITY
▲ — ▲ SPECIFIC ACTIVITY (ACTIVITY/OD 600)

• • CELL DENSITY (LOG OD 600)
□ □ TOTAL α AMYLASE ACTIVITY
▲ ▲ SPECIFIC ACTIVITY (ACTIVITY/OD 600)

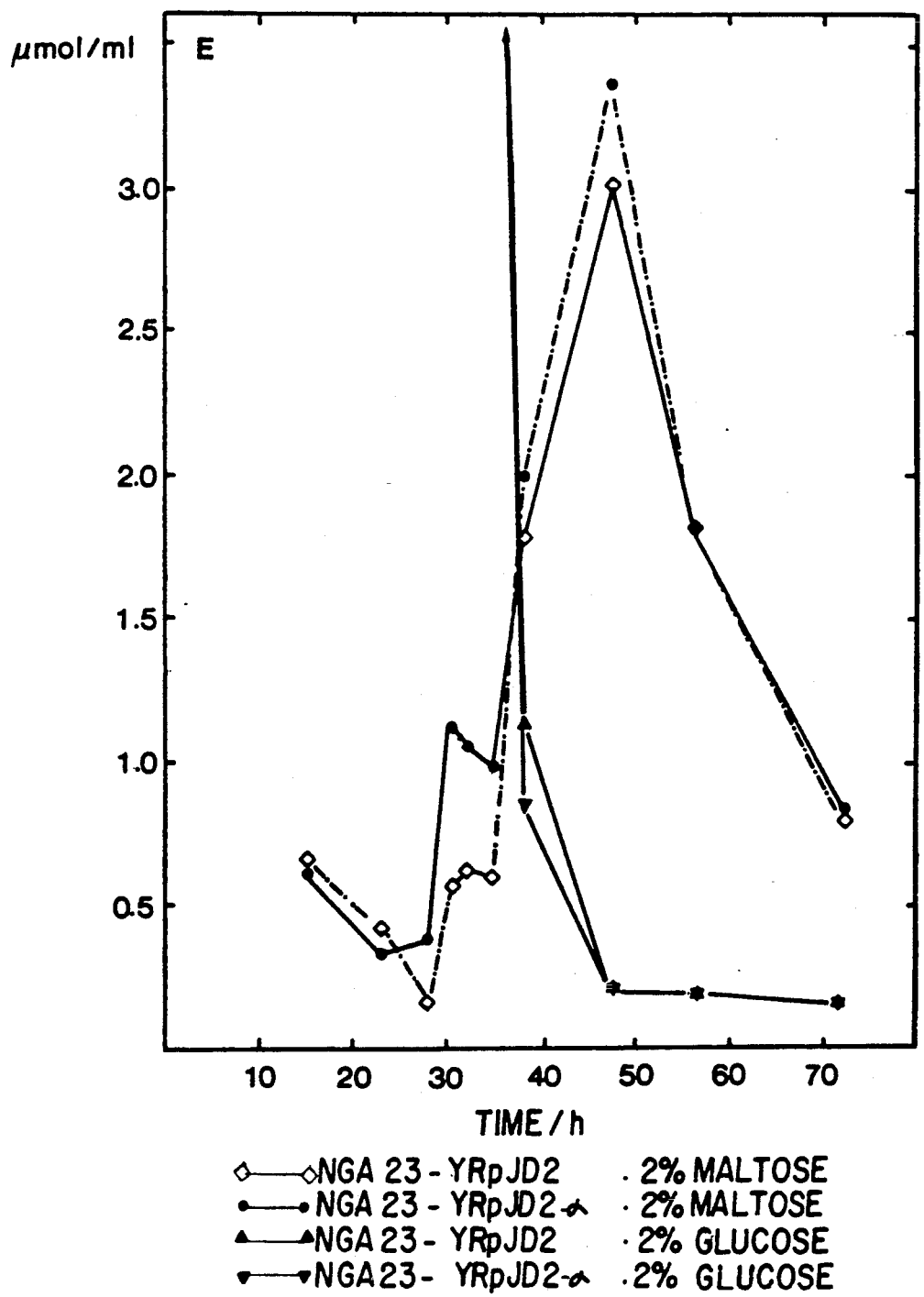

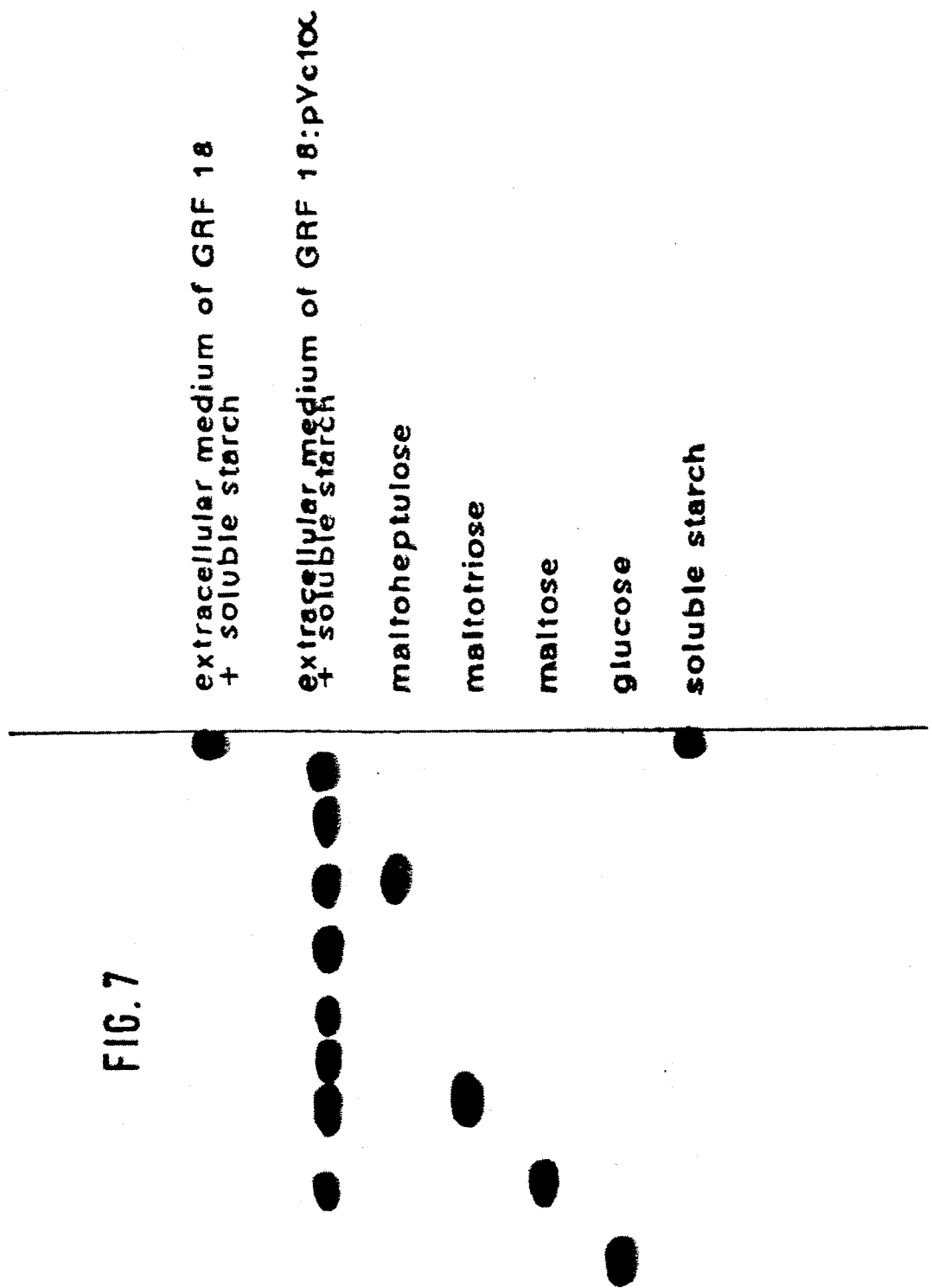

FIG. 8(I)
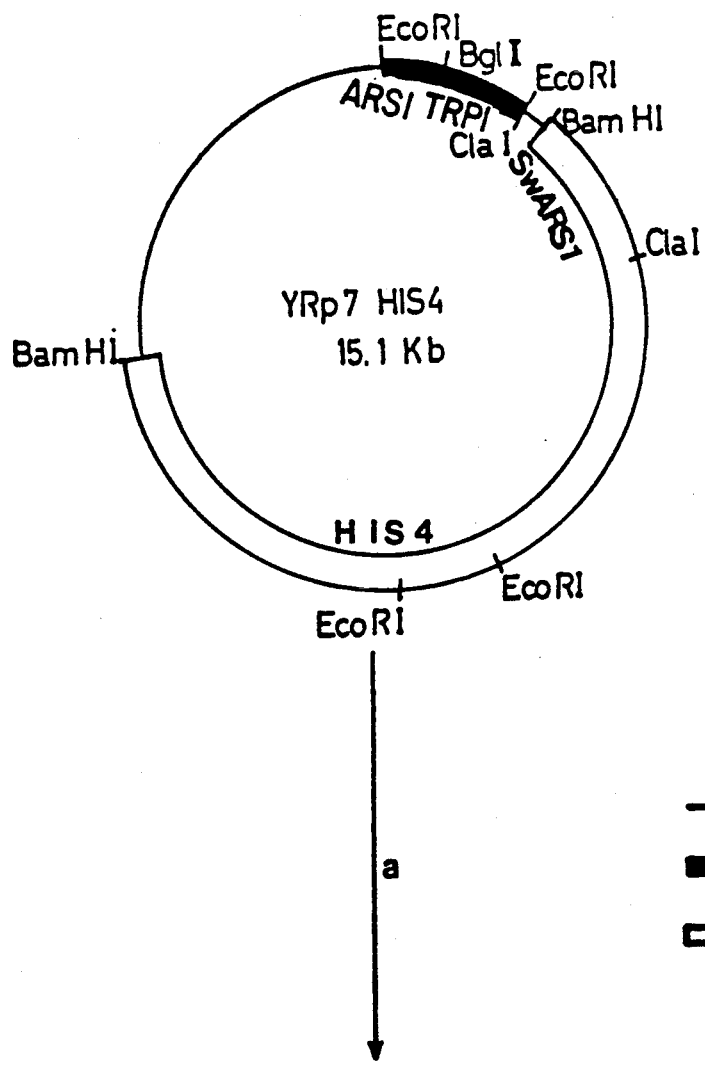
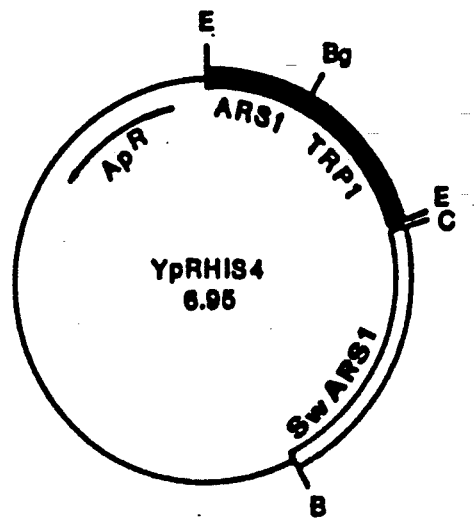

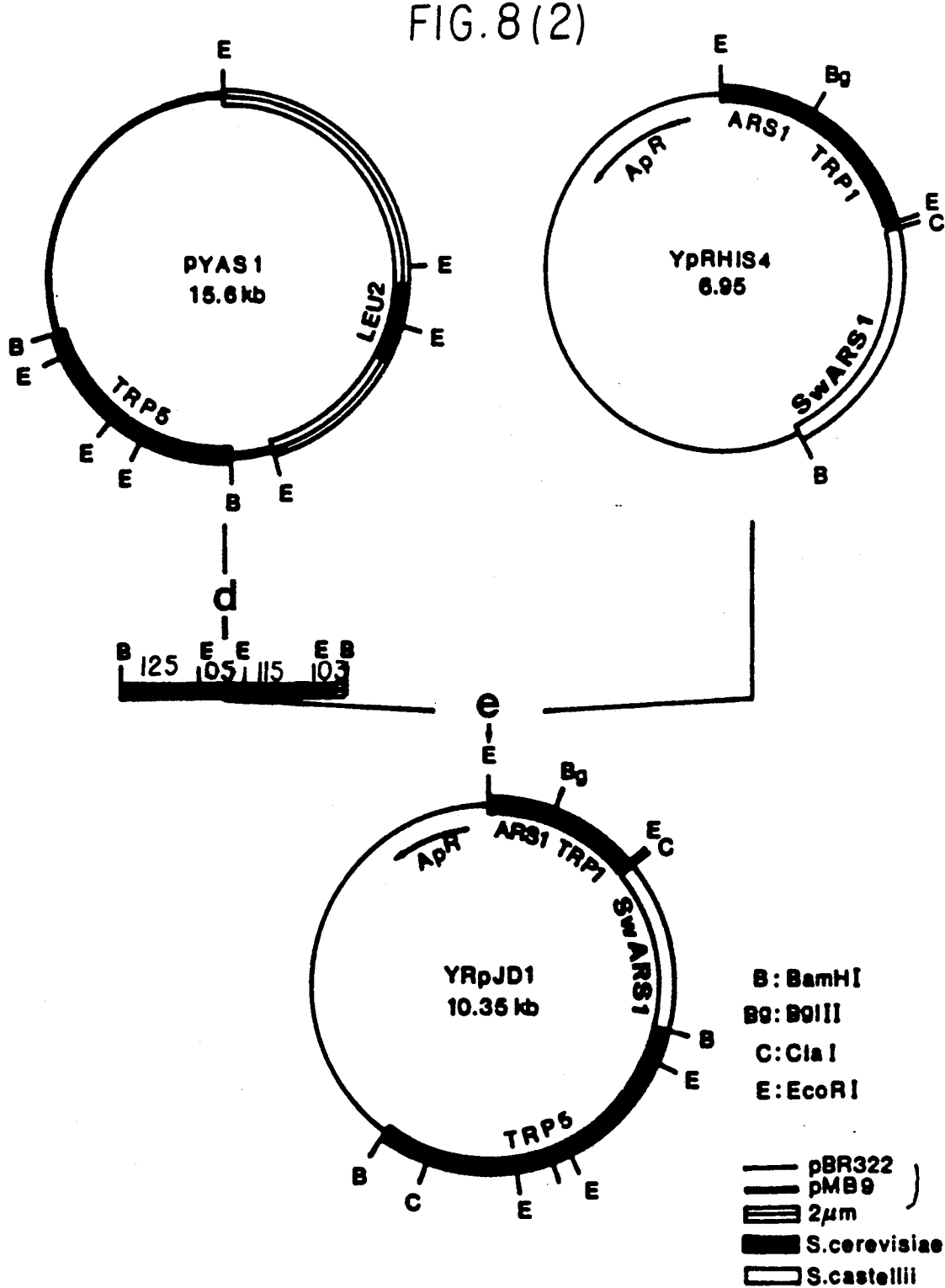

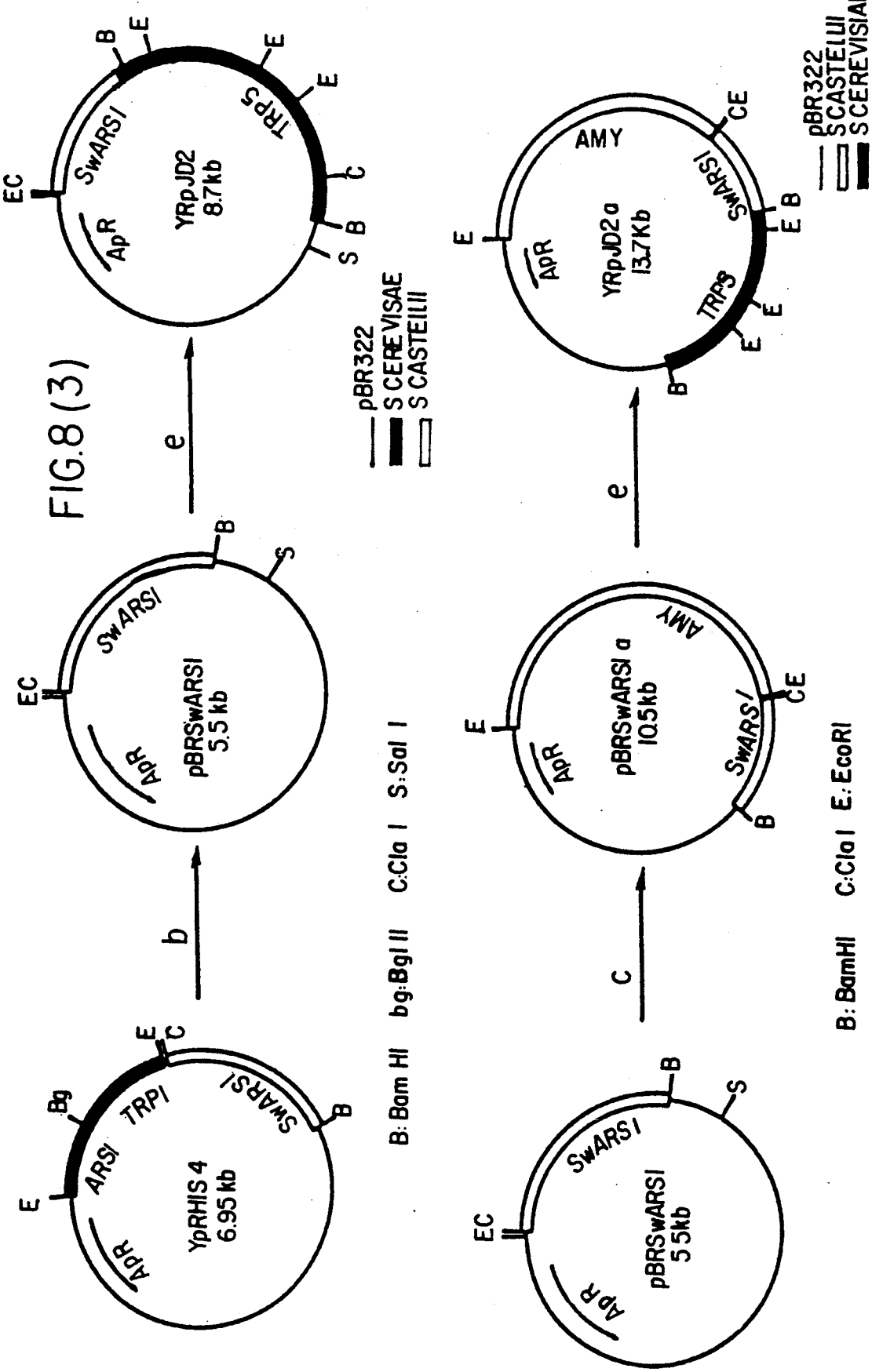

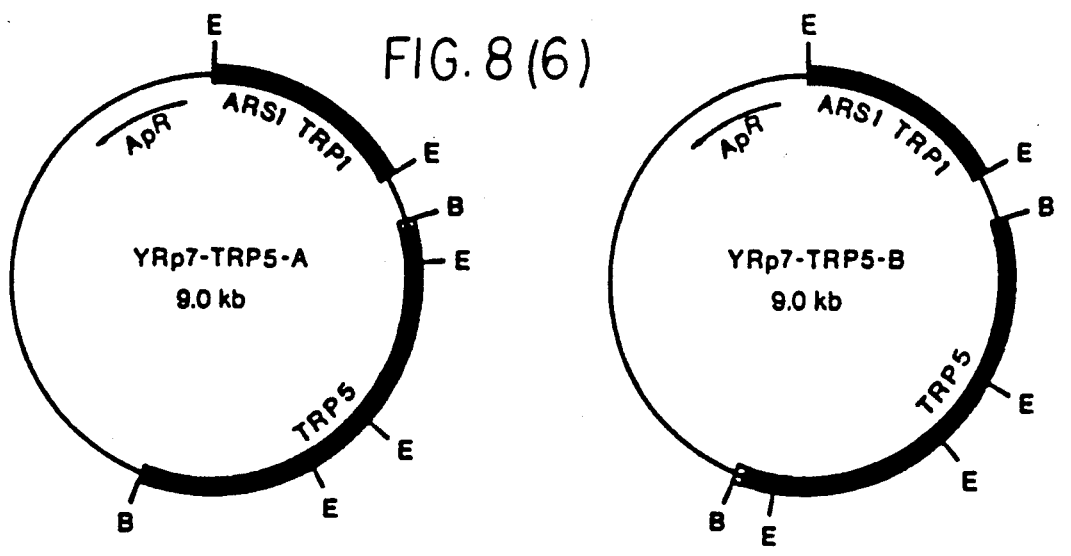
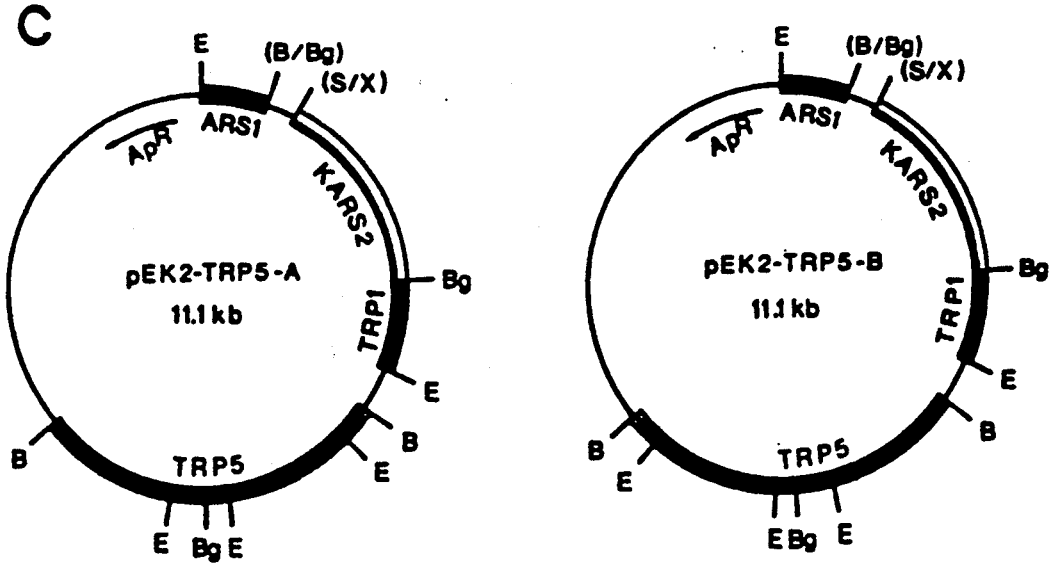
FIG. 8(6)

FIG. 9(I)A
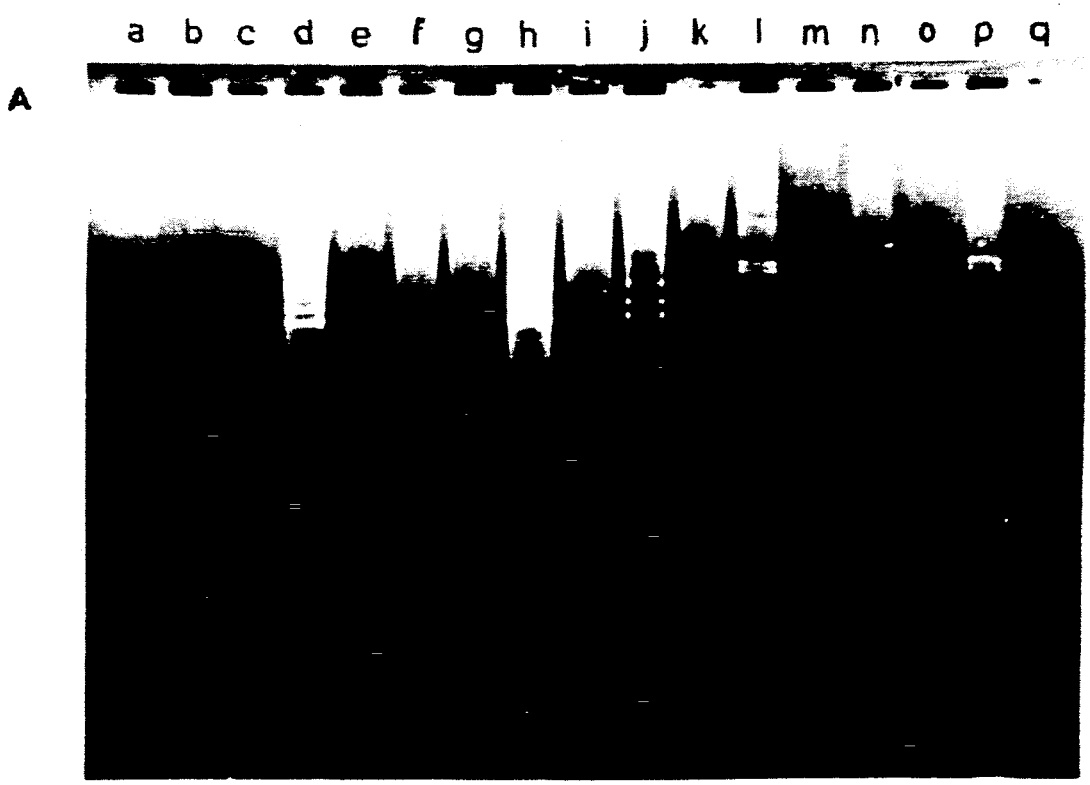
FIG. 9(I)B

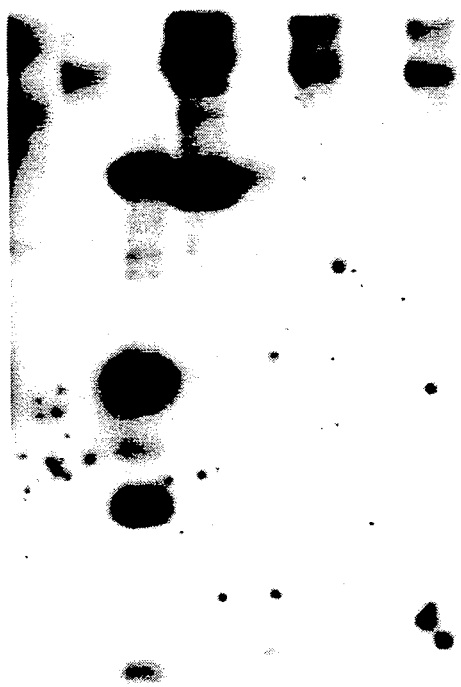
FIG.9(2)C

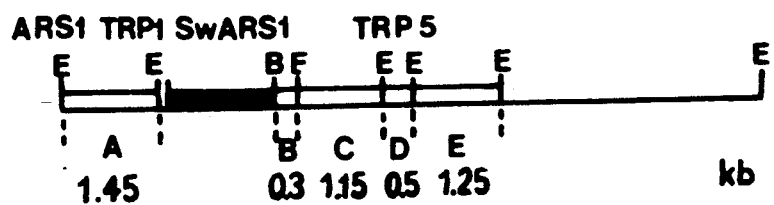
FIG.9(2)D

FIG.10(1)A
a b c d  e f g h i j k l m n o p
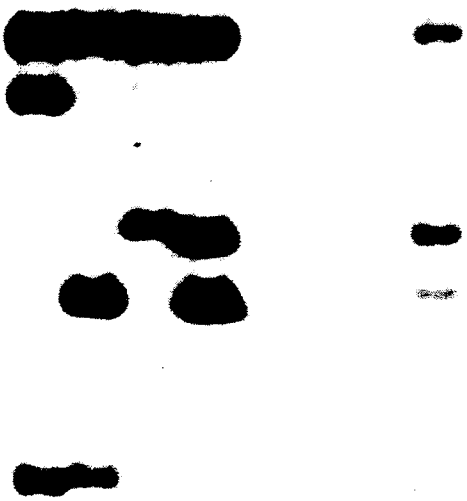
15h
FIG.10(1)B

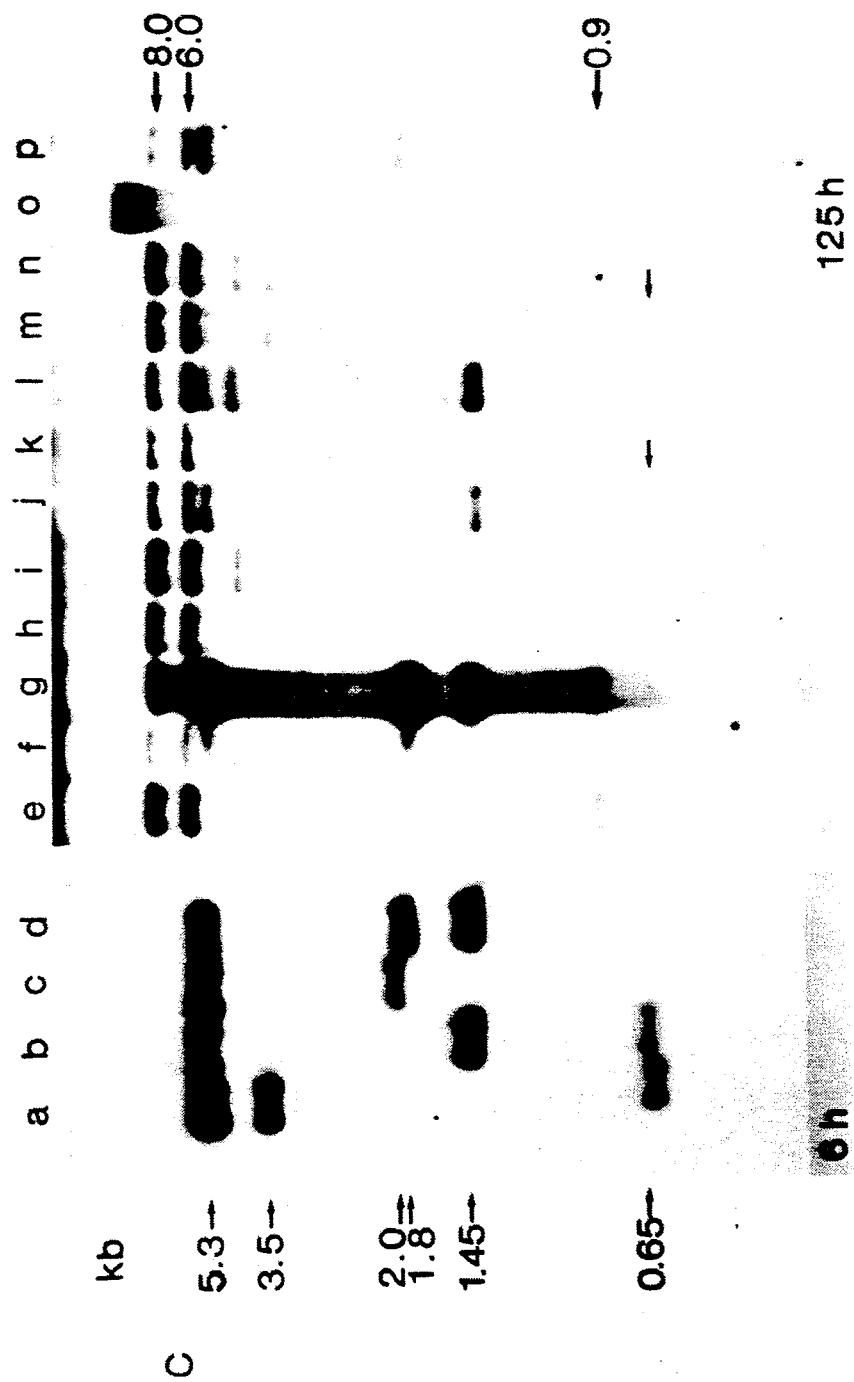
FIG.10(2)C

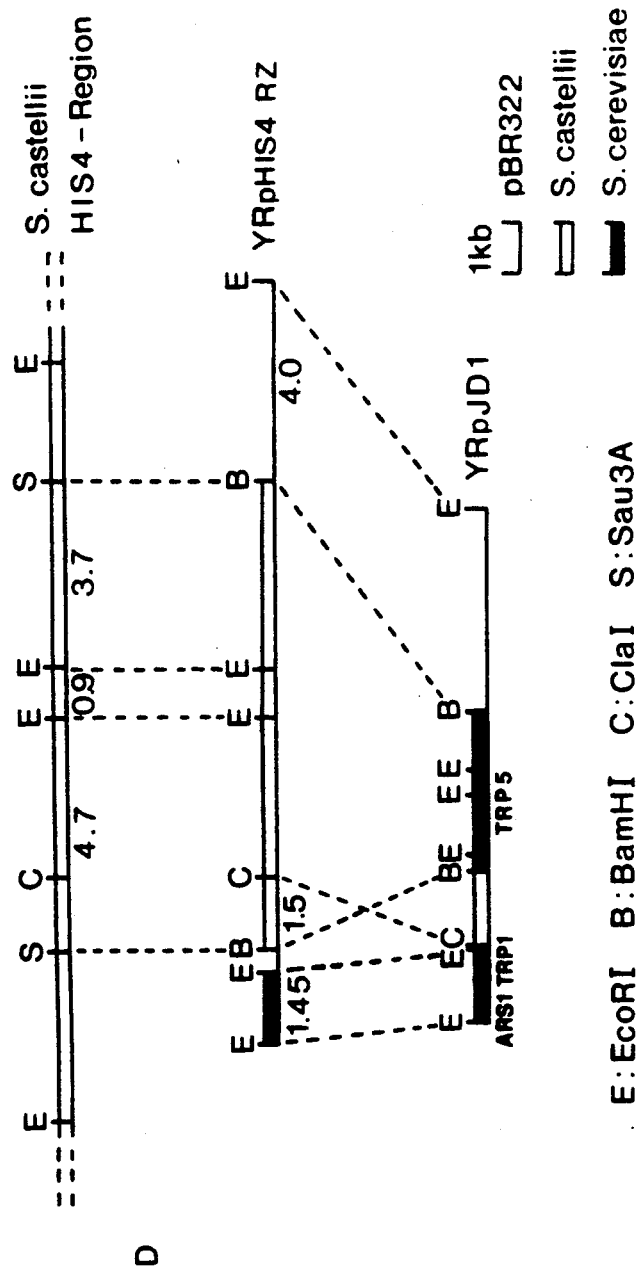
FIG.10(2)D

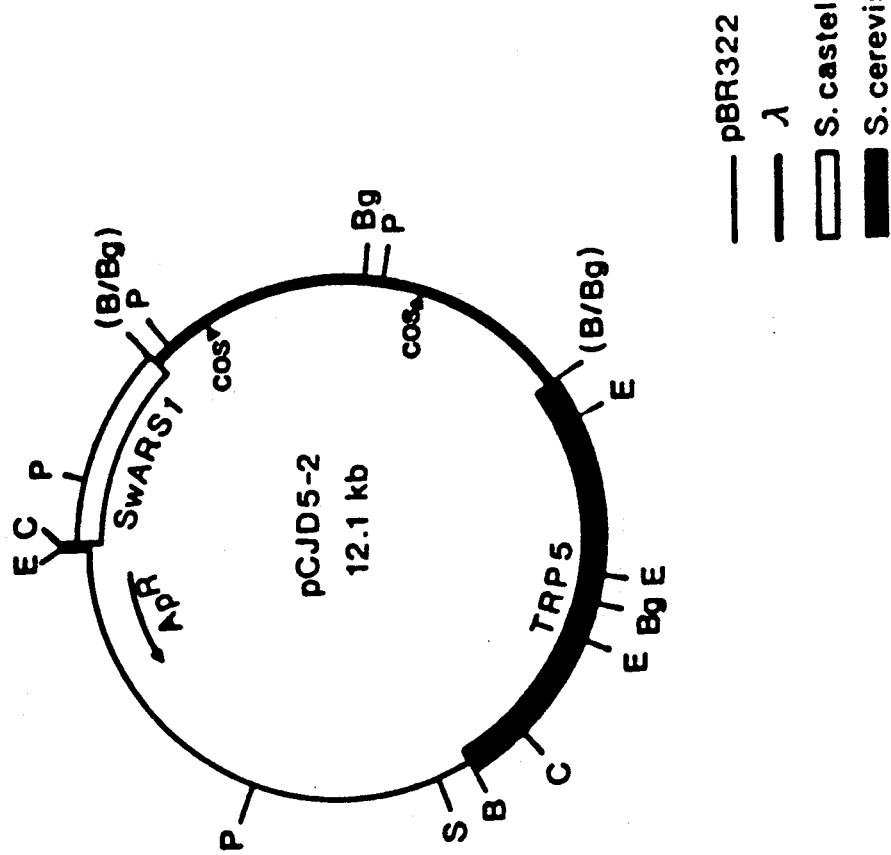
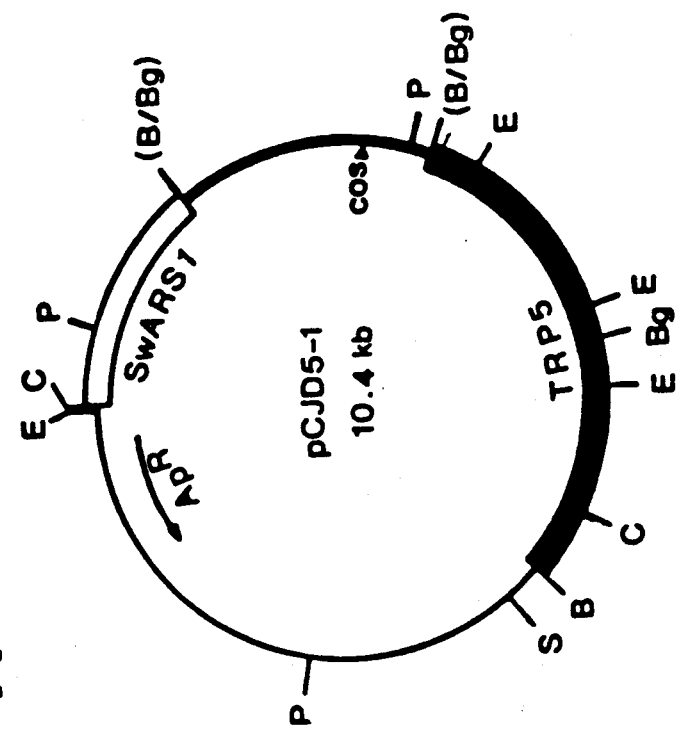
FIG.13(I)

FIG 15 (1)
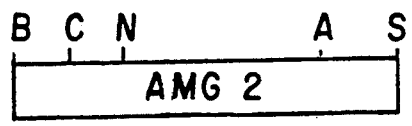
| | |
|---|---|
| A : Ava I | ───── pBR 322 |
| Bg : Bgl II | ▬▬▬▬▬ Saccharomyces cerevisiae |
| B : Bam HI | |
| E ; Eco RI | ▭▭▭▭▭ Kluyveromyces lactis |
| N : Nru I | |
| P ; Pvu II | ▢▢▢▢▢ Schwanniomyces castellii |
| Ps : Pst I | |
| S : Sal I | ▭▭▭▭▭ 2 μ DNA |
| X : Xho I | |
| | ───── λ DNA |
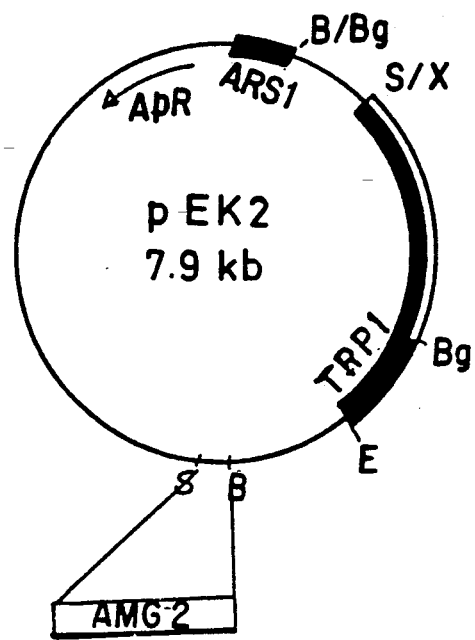

FIG.15(2)
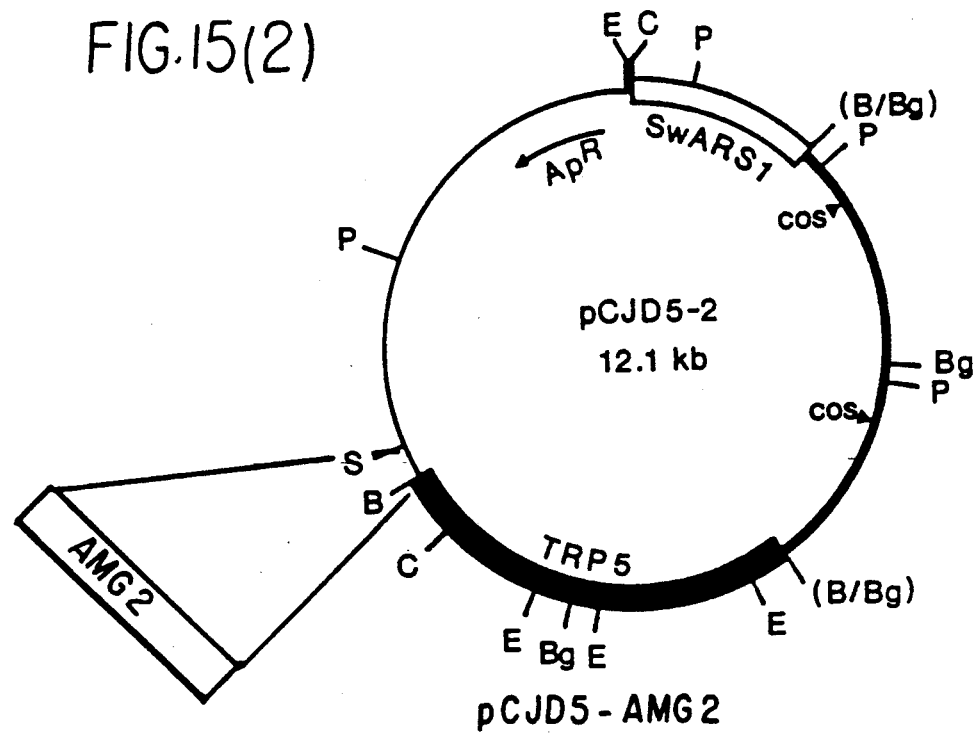
pCJD5-AMG2
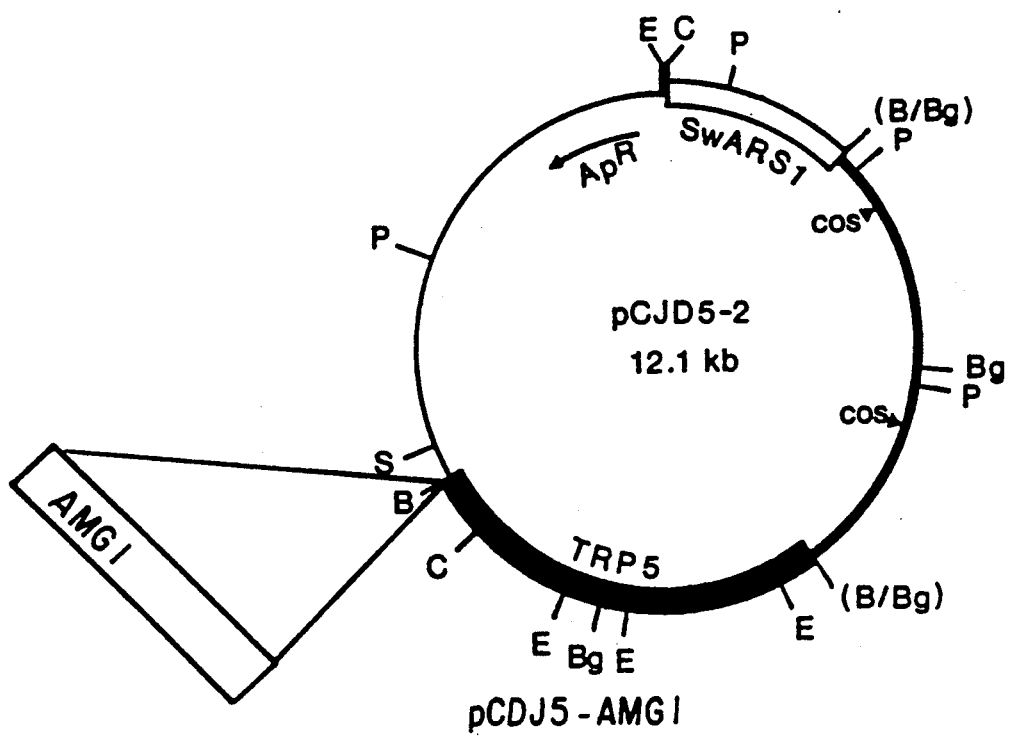
pCDJ5-AMG1

FIG.15 (3)
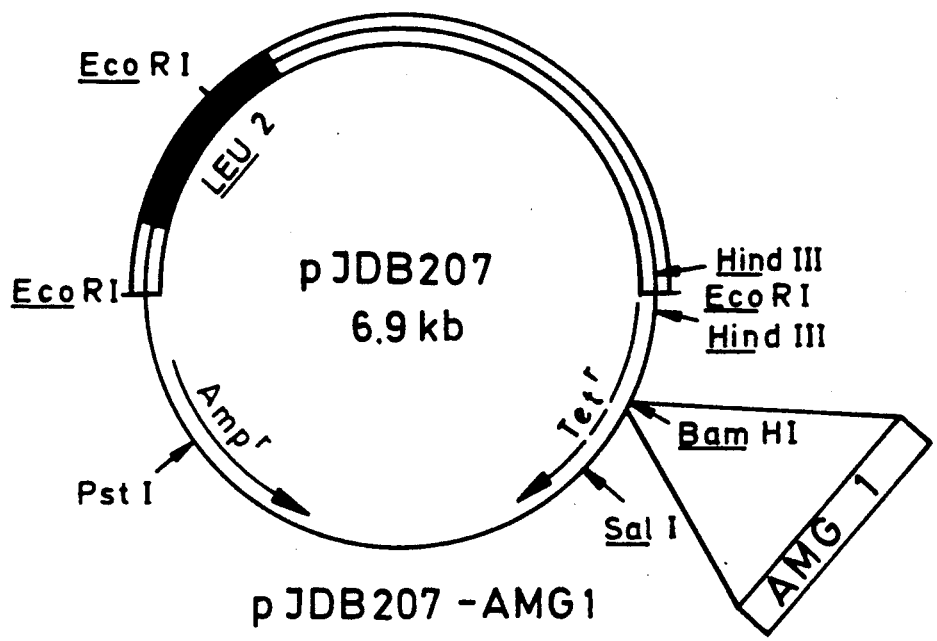
pJDB207-AMG1
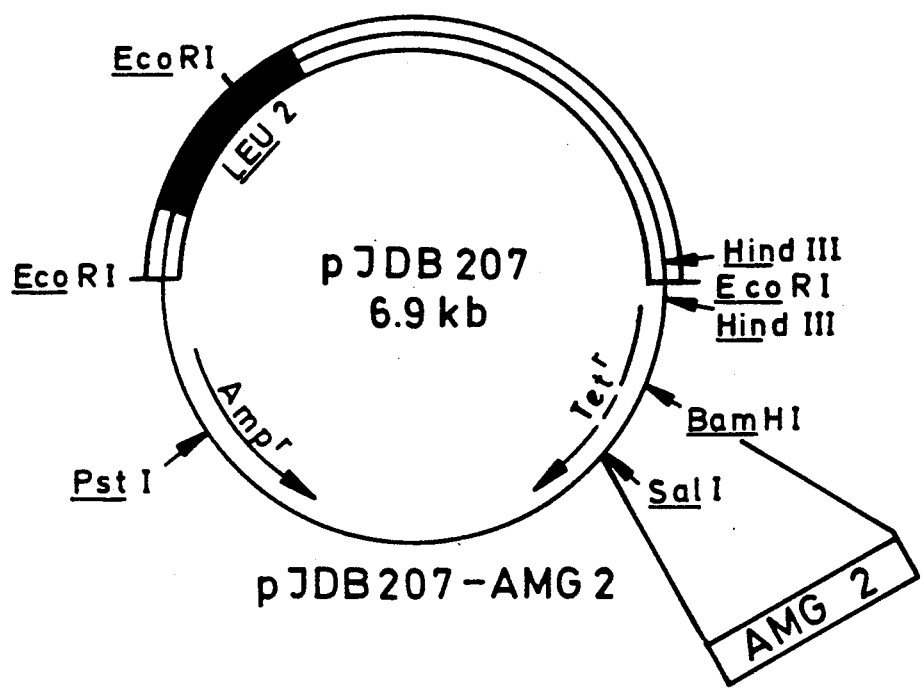
pJDB207-AMG2

FIG.17A

```
                                                        -310
                                         AGATCTACATTTTAAACCCCAG

-250
TCTACTCCAGATATTGGAGTATAACCCCATTCTTACCGTTATATCCATGACCCGCATCGA

-200
AATTTTCAAAGGATTTCGAGGAAATTCTTTCCTAAAATACGAAGTGTTATTGGTGATTCA

-150
ATTACTACGGAAACTACTCATATGGTAGTAGAGTTGGTGAATGTAGCGCAATTGTAATTT

-100
GCGAAGTTATAGTAATAGTTTGGCAAACTGGAGAATTTTTCATTATTGGGAAAATATAAA

-50                                                       -1
TAAAGGCAAGTATCCATTGAAATTTTAAAATGAACTCATGACTGTATTATAACAAGCAAG
```

FIG.17B

```
         10         20         30         40         50         60
ATGATTTTTCTGAAGCTGATTAAAAGTATAGTAATTGGTTTGGGATTAGTTAGTGCTATC
MetIlePheLeuLysLeuIleLysSerIleValIleGlyLeuGlyLeuValSerAlaIle 70         80         90        100        110        120
CAAGCAGCCCCTGCCTCTTCGATTGGATCTAGTGCTTCAGCATCTAGTTCAAGTGAGAGT
GlnAlaAlaProAlaSerSerIleGlySerSerAlaSerAlaSerSerSerSerGluSer 130        140        150        160        170        180
TCTCAGGCTACAATTCCCAATGATGTAACATTAGGTGTTAAACAAATTCCTAATATCTTT
SerGlnAlaThrIleProAsnAspValThrLeuGlyValLysGlnIleProAsnIlePhe 190        200        210        220        230        240
AATGACTCTGCTGTCGATGCTAATGCAGCTGCTAAAGGGTATGACTTGGTAAATGTTACT
AsnAspSerAlaValAspAlaAsnAlaAlaAlaLysGlyTyrAspLeuValAsnValThr 250        260        270        280        290        300
AATACTCCAAGAGGATTAACCGGTATCTTAAAATTAAAAGAAGCTACCAATATTTATGGT
AsnThrProArgGlyLeuThrGlyIleLeuLysLeuLysGluAlaThrAsnIleTyrGly 310        320        330        340        350        360
TATGATTTTGATTATTTAAACTTAACTGTTGAATACCAAGCTGATACCAGATTAAACGTT
TyrAspPheAspTyrLeuAsnLeuThrValGluTyrGlnAlaAspThrArgLeuAsnVal 370        380        390        400        410        420
CATATTGAACCAACTGATTTATCTGATGTATTTGTTTTACCAGAGCATTTAGTTGTTAAA
HisIleGluProThrAspLeuSerAspValPheValLeuProGluHisLeuValValLys 430        440        450        460        470        480
CCACTGGTGGAAGGTGATGCACAATCTTATAACTTCGACAATTCCGATTTGGTTTTCGAA
ProLeuValGluGlyAspAlaGlnSerTyrAsnPheAspAsnSerAspLeuValPheGlu 490        500        510        520        530        540
TACTCTAATACTGACTTCTCCTTTGAAGTTATTAGATCATCTACTAAAGAAGTTTTATTT
TyrSerAsnThrAspPheSerPheGluValIleArgSerSerThrLysGluValLeuPhe 550        560        570        580        590        600
TCTACTAAAGGTAATCCATTGGTTTTTTCAAATCAATTCATTCAATTCAATTCGTCATTG
SerThrLysGlyAsnProLeuValPheSerAsnGlnPheIleGlnPheAsnSerSerLeu 610        620        630        640        650        660
CCAAAGAACCATGTTATTACTGGTCTTGGTGAATCTATTCACGGTTTAGTTAACGAACCA
ProLysAsnHisValIleThrGlyLeuGlyGluSerIleHisGlyLeuValAsnGluPro 670        680        690        700        710        720
GGTAGCGTTAAAACATTATTTGCTAATGATGTTGGTGATCCAATCGATGGTAATATTTAT
GlySerValLysThrLeuPheAlaAsnAspValGlyAspProIleAspGlyAsnIleTyr 730        740        750        760        770        780
GGTGTCCATCCAGTTTATCTTGATCAAAGATATGACACTGAAACTACCCATGCTGTTTAT
GlyValHisProValTyrLeuAspGlnArgTyrAspThrGluThrThrHisAlaValTyr 790        800        810        820        830        840
TGGAGAACTTCTGCTATTCAAGAAGTATTAATCGGTGAGGAATCTATTACTTGGAGAGCT
TrpArgThrSerAlaIleGlnGluValLeuIleGlyGluGluSerIleThrTrpArgAla 850        860        870        880        890        900
CTTTCAGGTGTTATTGATTTATACTTCTTTAGTGGTCCTACACCAAAAGATGCCATTCAA
LeuSerGlyValIleAspLeuTyrPhePheSerGlyProThrProLysAspAlaIleGln
```

FIG. 17C

```
          910        920        930        940        950        960
CAGTATGTCAAAGAGATTGGTTTACCAGCTTTCCAACCATACTGGTCGTTAGGTTACCAT
GlnTyr Val LysGlu Ile GlyLeuProAla PheGln Pro Tyr Trp Ser LeuGly Tyr His 970        980        990       1000       1010       1020
CAATGTAGATGGGGTTACGATACTATCGAAAAATTATCTGAAGTTGTTGAAAACTTCAAG
Gln CysArgTrpGlyTyr AspThr Ile GluLysLeuSer Glu Val Val Glu AsnPheLys 1030       1040       1050       1060       1070       1080
AAATTTAATATTCCATTAGAAACTATCTGGTCAGACATTGATTACATGGACTCTTATAAA
LysPheAsnIleProLeu GluThr Ile Trp Ser AspIleAspTyr Met AspSer Tyr Lys 1090       1100       1110       1120       1130       1140
GATTTCACTTATGATCCACACAGATTCCCACTAGATGAATATCGTAAATTCCTTGATGAG
AspPheThr TyrAspProHisArg ProLeuAspGlu Tyr ArgLysPhe LeuAspGlu 1150       1160       1170       1180       1190       1200
TTGCACAAAAATAATCAACACTATGTTCCTATTTTGGATGCTGCTATTTACGTTCCAAAC
LeuHis Lys AsnAsnGlnHis Tyr Val Pro Ile LeuAspAlaAla Ile Tyr Val ProAsn 1210       1220       1230       1240       1250       1260
CCAAACAATGCTACGGATAACGAATACCAACCTTTCCACTATGGTAATGAAACCGATGTC
Pro AsnAsnAlaThr AspAsnGlu Tyr GlnProPheHis Tyr Gly AsnGluThr AspVal 1270       1280       1290       1300       1310       1320
TTCTTAAAGAATCCAGATGGTTCATTATATATTGGTGCTGTTTGGCAGGTTACACTGTTT
PheLeu LysAsnProAspGlySerLeuTyr Ile GlyAlaValTrpGln Val Thr LeuPhe 1330       1340       1350       1360       1370       1380
TCCAGATTTCTTAGCAGAAAACATTCAGATATGGATAAAGTCATTAAAGATTGGTATGAA
Ser ArgPheLeuSer ArgLys His Ser AspMetAspLys Val Ile LysAspTrp Tyr Glu 1390       1400       1410       1420       1430       1440
TTAACTCCTTTTGATGGTATTTGGGCTGATATGAATGAAGTCTCATCATTCTGTGTTGGT
LeuThr Pro PheAspGly Ile TrpAla AspMetAsnGlu Val Ser Ser Phe CysVal Gly 1450       1460       1470       1480       1490       1500
TCTTGTGGTACTGGTAAATACTTCGAAAACCCAGCATATCCTCCATTTACTGTTGGAAGT
Ser CysGly ThrGly LysTyr PheGlu AsnPro AlaTyr Pro Pro PheThr Val GlySer 1510       1520       1530       1540       1550       1560
AAAGCTACCTCTTATCCAGTTGGTTTCGATGTTTCTAACGCATCTGAATGGAAATCTATT
LysAlaThr Ser Tyr Pro Val Gly PheAspVal Ser AsnAlaSer GluTrpLysSer Ile 1570       1580       1590       1600       1610       1620
CAAAGCTCAATTTCTGCTACTGCTAAGACTTCTTCAACTTCTTCCGTATCGTCGTCTTCA
GlnSer Ser Ile Ser AlaThr AlaLysThr Ser Ser Thr Ser Ser Val Ser SerSer Ser 1630       1640       1650       1660       1670       1680
TCCACAATCGATTATATGAACACTTTAGCTCCAGGTAAAGGTAATATTAATTATCCACCA
Ser Thr Ile AspTyr MetAsnThr Leu AlaProGly LysGly Asn Ile AsnTyr Pro Pro 1690       1700       1710       1720       1730       1740
TATGCTATTTACAACATGCAAGGTGACTCCGATCTTGCTACTCATGCAGTATCTCCAAAT
Tyr AlaIleTyrAsnMetGln Gly AspSer AspLeuAlaThr His AlaValSer ProAsn 1750       1760       1770       1780       1790       1800
GCTACACATGCTGATGGTACAGTTGAATATGATATTCACAATCTTTATGGTTACTTGCAA
AlaThrHis AlaAspGly ThrVal GluTyr Asp Ile HisAsnLeuTyr Gly Tyr LeuGln
```

FIG. 17D

```
         1810       1820       1830       1840       1850       1860
GAAAATGCTACTTATCATGCATTATTGGAAGTTTTTCCTAACAAGAGACCATTCATGATT
Glu AsnAlaThr Tyr His AlaLeuLeuGlu Val PhePro Asn LysArg ProPheMet Ile 1870       1880       1890       1900       1910       1920
TCCAGATCAACCTTTCCAXGCGCTGGTAAATGGACCGGCCATTGGGGTGGTGACAACACT
SerArgSerThrPhePro   AlaGly LysTrpThr GlyHis TrpGlyGlyAspAsnThr 1930       1940       1950       1960       1970       1980
GCTGATTGGGCTTATGCTTACTTCTCTATCCCTCAAGCATTCTCAATGGGTATTGCTGGC
AlaAspTrpAlaTyrAlaTyr PheSer Ile ProGlnAlaPheSer MetGly IleAlaGly 1990       2000       2010       2020       2030       2040
CTTCCATTCTTTGGTGCCGATGTTTGTGGTTTCAATGGTAATTCTGATTCTGAATTATGT
Leu Pro PhePheGly AlaAspVal Cys Gly Phe AsnGly Asn Ser AspSer GluLeu Cys 2050       2060       2070       2080       2090       2100
TCAAGATGGATGCAATTAGGTTCTTTCTTCCCATTCTACAGAAACCACAACTATTTAGGT
Ser Arg TrpMetGln Leu GlySer PhePheProPhe Tyr ArgAsn His AsnTyr LeuGly 2110       2120       2130       2140       2150       2160
GCTATTGATCAGGAACCATATGTCTGGGAATCAGTTGCTGAAGCTACTAGAACTTCTATG
Ala Ile AspGlnGluPro Tyr Val TrpGluSer Val Ala Glu Ala Thr ArgThr SerMet 2170       2180       2190       2200       2210       2220
GCCATTAGATACTTATTATTACCATATTACTACACTTTATTACATGAATCTCATACTACT
Ala Ile ArgTyr LeuLeuLeu ProTyr Tyr Tyr Thr Leu Leu His GluSer His Thr Thr 2230       2240       2250       2260       2270       2280
GGTTTACCAATCTTAAGAGCTTTCTCGTGGCAATTCCCTAACGATCGTTCCTTAAGTGGT
GlyLeu Pro Ile LeuArg Ala PheSer Trp Gln PhePro Asn AspArgSerLeu SerGly 2290       2300       2310       2320       2330       2340
GTCGATAACCAATTTTTTGTCGGTGATGGTTTAGTTGTTACTCCTGTCTTAGAACCTGGT
Val AspAsnGlnPhe PheVal GlyAspGly LeuVal Val Thr Pro ValLeu GluProGly 2350       2360       2370       2380       2390       2400
GTTGATAAGGTTAAAGGTGTTTTCCCAGGAGCTGGTAAAGAGGAAGTTTACTACGACTGG
Val AspLysVal Lys Gly ValPhePro GlyAlaGly LysGluGlu Val Tyr Tyr AspTrp 2410       2420       2430       2440       2450       2460
TACACCCAAAGAGAAGTTCACTTTAAAGACGGTAAGAATGAAACTTTAGATGCACCATTA
Tyr Thr GlnArgGlu Val His PheLysAspGly LysAsnGluThr LeuAspAlaProLeu 2470       2480       2490       2500       2510       2520
GGTCATATTCCATTACACATTAGAGGTGGTAACGTCTTGCCAACTCAAGAGCCAGGTTAT
Gly His Ile ProLeu His Ile ArgGly Gly AsnVal LeuProThr GlnGlu ProGlyTyr 2530       2540       2550       2560       2570       2580
ACTGTTGCTGAGTCAAGACAAAATCCATTTGGTTTAATTGTCGCTTTAGATAACGATGGC
Thr Val AlaGlu SerArgGln AsnPro PheGlyLeu Ile Val AlaLeuAspAsn AspGly 2590       2600       2610       2620       2630       2640
AAAGCTCAAGGTAGCTTATACCTTGATGATGGTGAATCATTAGTAGTAGACTCTTCATTG
LysAlaGlnGly Ser Leu Tyr LeuAspAspGlyGluSer Leu Val Val AspSer SerLeu 2650       2660       2670       2680       2690       2700
TTGGTTAGTTTCTCTGTTTCTGATAACACATTATCAGCATCTCCATCTGGTGACTATAAA
LeuVal Ser PheSer Val Ser AspAsnThr LeuSer Ala Ser ProSer GlyAsp Tyr Lys
```

FIG. 17E

```
      2710      2720      2730      2740      2750      2760
GCTGATCAACCTTTAGCTAATGTTACCATCTTAGGGGTTGGCCATAAACCAAAATCAGTT
Ala AspGln Pro Leu Ala Asn Val Thr Ile Leu Gly Val Gly His Lys Pro Lys Ser Val 2770      2780      2790      2800      2810      2820
AAATTTGAAAACGCTAATGTTGATTTCACCTACAAGAAATCAACCGTTTTCGTTACTGGC
Lys Phe Glu Asn Ala Asn Val Asp Phe Thr Tyr Lys Lys Ser Thr Val Phe Val Thr Gly 2830      2840      2850      2860      2870      2880
TTAGATAAATACACCAAGGATGGTGCATTTTCTAAGGATTTCACCATTACTTGGTAATTT
Leu Asp Lys Tyr Thr Lys Asp Gly Ala Phe Ser Lys Asp Phe Thr Ile Thr Trp 2890      2900      2910      2920      2930      2940
TAACATCCACTTAGTTCAATTCCATTCTTTTCTTTTTCCCGTGAAATTCTGAATTTGAAA 2950      2960      2970      2980      2990      3000
TTATTTGAATGATATCATTTTAGTTTTCTTCAGCTTATGCTATGTTTATTTCGATTTTAA 3010      3020      3030      3040      3050      3060
ATGTTAAAAGTTTTTTATGTTTATGTTGTTTTATTGATGTAGTTGATAAAATATAGCAAA 3070      3080      3090      3100      3110      3120
TACATCGAAAAATTTGCGATGAAATTTTGCAGCTCATTAGAAATGTAGTCAATCATTAGT 3130      3140      3150      3160      3170      3180
CACATTGGACCACTATATAACAAACAACAACTATTCCAAGAAAAATATATGTAAGGATAC 3190      3200      3210      3220      3230      3240
TAGATCATAAATTCTTATTGACTTTGTTTTTTTTAACAATAGTTACATAAGGAATATTCG 3250      3260      3270      3280      3290      3300
TTTACTACAAAACCATTGGTCTTGTAAAGAAGCAGACGAGGCGTATGTTTGTGGTTGCGG 3310      3320
CCGCAATACTAGTTTACAAAG
```

FERMENTATION PROCESSES USING AMYLOLYTIC ENZYME PRODUCING MICROORGANISMS

This is a division, of application Ser. No. 07/085,107 filed Aug. 13, 1987, which is a Continuation-in-Part of U.S. Ser. No. 07/062,943, filed Jun. 16, 1987, now abandoned the contents of each of which are hereby incorporated by reference.

Species of the yeast genus Schwanniomyces hydrolyse starch to glucose as the result of the production of two extracellular enzymes, namely amylase ($\alpha$-1,4-glucan 4-glucanohydrolase E.C.3.2.1.1) and glucoamylase (syn. amyloglucosidase) ($\alpha$-1,4-glucanglucohydrolase, E.C.3.2.1.3. With debranching activity E.C.3.2.1.9.).

The amylolytic systems of Schwanniomyces castellii and Schwanniomyces alluvius are well documented (Oteng-Gyang et al., 1981; Sills et al., 1982, 1984a, 1984b; Wilson et al., 1982).

It is desirable to work with Schwanniomyces spp. because the $\alpha$-amylase has the liquefying activity and the glucoamylase has the debranching activity, and because the amylolytic system is sensitive to pasteurization conditions normally employed in brewing. (Sills et al., 1984a and b).

The yeast Saccharomyces, having none of the mentioned activities of the yeast Schwanniomyces, is the mostly used organism in brewery, baking processes and in the ethanol fermentation industry. In the fermentation processes, starch is conventionally used as a raw material. Since, however, as mentioned, Saccharomyces cerevisiae is not able to hydrolyse starch, the traditional conversion of starch into ethanol and $CO_2$ by Saccharomyces cerevisiae requires two enzymatic degradation processes prior to the fermentation activity by Saccharomyces cerevisiae, namely liquefication, carried out by adding $\alpha$-amylase and saccharification by adding glucoamylase with debranching activity (Fogarty et al., 1979).

In the European patent application no. 0 125 615, the use of yeast of the genus Schwanniomyces for the production of low calorie beers has already been described. Using yeast of the genus Schwanniomyces provides an organism in the fermentation procedures which is able to produce the amylolytic enzymes, and therefore the mentioned enzymes do not have to be added prior to the fermentation procedure. Nevertheless, the yeast Schwanniomyces is not at all as efficient and adapted as Saccharomyces cerevisiae in brewery and industrial ethanol production. In the above mentioned European patent application, it has therefore been proposed to use Schwanniomyces in addition to the more efficient genus Saccharomyces, the latter still being the essential microorganism for the fermentation of degraded carbohydrates to ethanol and the starch degrading enzymes from Schwanniomyces. The enzymes are still added separately as usual in the state of the art.

Several amylolytic enzymes encoding genes could be cloned and expressed in Saccharomyces cerevisiae, namely the $\alpha$-amylase gene of mice (Thomsen, 1983) and of wheat (Rothstein et al., 1984) and the glucoamylase gene of Saccharomyces diastaticus (Yamashita and Fukui, 1983), of Aspergillus niger (Nunnberg et al., 1984; Innis et al., 1985), Candida albicans (Cohen et al. 1985) and Rhizopus oryzae European Patent Application 85 115 910.3).

The amylolytic enzymes produced by the above mentioned donor organisms are, however, not useful for the purposes of the present invention. For the use of genetically manipulated Saccharomyces cerevisiae in brewing and baking procedures and the production of industrial ethanol, it is highly desirable to clone the respective genes derived from very closely related organisms, since the production and application of the expressed enzymes is much more acceptable for the food industry and has the required enzymological and chemical properties for industrial processes. Therefore, the amylolytic enzymes of the microorganism Schwanniomyces, which can be produced by recombinant DNA technology in a number of host microorganisms, are more suitable for a number of applications due to the close relationship of the microorganism Schwanniomyces and the host microorganisms used, and due to the low temperature optimum, the temperature sensitivity, and the high stability of the amylolytic enzymes produced by Schwanniomyces.

The $\alpha$-amylase gene of Schwanniomyces is the first $\alpha$-amylase gene cloned from a yeast species and is, as a gene from a narrowly related yeast organism, more compatible with the fermentation processes required in the food industry, for example the brewing and baking processes.

In addition, compared to other $\alpha$-amylases, the $\alpha$-amylase of Schwanniomyces has an optimal enzyme activity at a lower temperature of about 37° C., which allows application at lower fermentation or process temperatures. In addition, the $\alpha$-amylase of Schwanniomyces can be inactivated at 50° C.

The glucoamylase of Schwanniomyces has a special debranching activity and is hence able to hydrolyse starch virtually completely into glucose, whereas the glucoamylase of Candida albicans or Saccharomyces diastaticus has no debranching activity, and hence are not able to hydrolyse starch completely into glucose. The glucoamylase of Schwanniomyces, besides its specially suited enzymological and chemical properties, including optimum of pH and temperature, has the additional advantages over the glucoamylases encoded by other genes already cloned in that this enzyme originates from a yeast species and can be heat inactivated at pasteurization conditions (Sills et al., 1983) which are normally employed in the brewing process.

It would therefore be most advantageous for the brewing process, the production of industrial ethanol and yeast biomass to provide cultures of Saccharomyces cerevisiae with its high $CO_2$ production, its good fermentation efficiency, its high ethanol tolerance, with the ability to hydrolyze starch entirely by synthesising and secreting $\alpha$-amylase and glucoamylase. Also for the $CO_2$ production in baking, amylolytic enzyme producing strains can be of great advantage.

It was therefore an object of the present invention to provide a microorganism suitable for brewing and baking processes, the production of industrial ethanol and of biomass having the ability to hydrolyze starch entirely if required by being capable of synthesising and secreting $\alpha$amylase and glucoamylase.

The desired microorganisms can be provided by genetical manipulation of the microorganisms used by recombinant DNA technology. Recombinant DNA technology is used to clone the commercially interesting genes coding for $\alpha$-amylase and glucoamylase, whereby DNA fragments are cloned which contain the $\alpha$-amylase and/or glucoamylase genes of a yeast of the genus Schwanniomyces. After transformation of a host microorganism, the cloned genes coding for amylolytic enzymes are expressed in a host microorganism, for example, *Saccharomyces cerevisiae* and the gene products are secreted into the medium. The enzymatic pre-treatment of starch and/or non-fermentable dextrins, which was necessary to provide the fermenting microorganisms with fermentable sugar, can therefore be avoided, with all advantages with respect to a less expensive and a simplified fermentation processes, for example, in the fields of brewing, production of industrial ethanol and production of biomass. For the baking process, amylolytic yeast can be of great advantage for the preparation of certain types of doughs.

One of the advantages of providing a fermenting microorganism, for example *Saccharomyces cerevisiae*, having the ability to produce α-amylase and/or glucoamylase is based on the fact that the starch can be continuously and quantitatively degraded, and the biomass or ethanol is simultaneously produced by aerobic or anaerobic conversion of the low molecular carbohydrates resulting from the degradation of the starch. In the case of the above mentioned brewing processes, the result of this complete degradation of the starch is a low calorie beer, since the resulting low molecular carbohydrates are easily fermented by the genetically manipulated microorganisms into ethanol and $CO_2$.

A further example for the use of amylolytic *Saccharomyces cerevisiae* strains in beer brewing is the production of special beers like low carbohydrate beer, diet beer and special flavoured beer. In addition these strains allow a broadening of the range of starch-containing raw materials for beer brewing.

Although the general idea of the present invention described above comprises the use of various host microorganisms which are suitable in one of the afore mentioned fermentation processes or the production of biomass, a preferred example of constructing a microorganism so as to be able to express and secrete amylolytic enzymes is now described.

For the construction of a yeast of the species *Saccharomyces cerevisiae*, a transformation system with a particular marker was developed, providing both regulation of the amylase genes and over-production of their gene product in the yeast cells.

According to the present invention, in addition a shuttle cosmid vector has been constructed which can be used as a shuttle vector for transformation of Schwanniomyces, Saccharomyces, *Escherichia coli* and *Schizosaccharomyces pombe*.

According to a preferred embodiment of the present invention, the yeast *Schwanniomyces castellii* acts as a donor for the cloning of α-amylase and/or glucoamylase genes. The yeast *Saccharomyces cerevisiae* acts as a host yeast being capable of expressing the mentioned genes for the amylolytic enzymes after having received the cloned genes adapted for expression by transformation procedures and further being capable of secreting the gene products.

As a result of genetic manipulation, furthermore, an overproduction of the amylolytic enzymes in the yeast *Schwanniomyces alluvius* is possible. This over-production of amylolytic enzymes in Schwanniomyces strains are of great advantage for the production of these enzymes as such, which after recovering in a known manner, can still be used as described above in fermentation processes in which it is still necessary to add the amylolytic enzymes separately.

The new Schwanniomyces vectors control the function of replication and maintenance in Schwanniomyces. This replication sequence (SwARS1) isolated from Schwanniomyces chromosomal DNA is responsible for autonomous replication in, and high frequency transformation of Schwanniomyces. The SwARS1-element is also functional in *Saccharomyces cerevisiae* and hence leads to high frequency transformation of *Saccharomyces cerevisiae* mutants with SwARS1-plasmid.

One suitable representative of Schwanniomyces vectors is pCJD5-1, a hybrid plasmid composed of the SwARS1 sequence, the cos (cohesive) sequence of bacteriophage λ, the pBR322 sequence and the TRP5 gene of *Saccharomyces cerevisiae* used as a selectable marker.

This plasmid is a new *Saccharomyces cerevisiae-Schwanniomyces alluvius-Escherichia coli* cosmid shuttle vector with suitable cloning sites for the construction of genomic DNA libraries.

The present invention provides furthermore a new simple and quick transformation procedure for the yeasts *Schwanniomyces alluvius, Saccharomyces cerevisiae, Schizosaccharomyces pombe, Kluyveromyces lactis.*

Using the above vector and transformation system it is possible to provide new genetically engineered yeast strains of the genus *Saccharomyces cerevisiae* which are capable of synthesizing amylases in culture for mass production.

A consequence of this mass production will be the use of this modified *Saccharomyces cerevisiae* strain in aerobic and anaerobic starch converting processes to yield yeast biomass, ethanol and $CO_2$.

According to this invention, new DNA sequences are provided which lead to expression and secretion of proteins in *Saccharomyces cerevisiae, Schwanniomyces alluvius, Schizosaccharomyces pombe* and *Kluyveromyces lactis*, since the new DNA sequences contain new secretion signals which allow secretion in the yeasts named.

In addition, sequences are provided by the new DNA sequences which allow regulated gene expression.

Another object of this invention is the provision of a vector without any *E. coli* sequence for the integration of the amylase genes into the *Saccharomyces cerevisiae* genome.

DETAILED DESCRIPTION OF THE PRESENT INVENTION

In the following, a more detailed description of all aspects of the present invention is given.

BRIEF DESCRIPTION OF THE FIGURES

FIG. 1

Figure 4A:
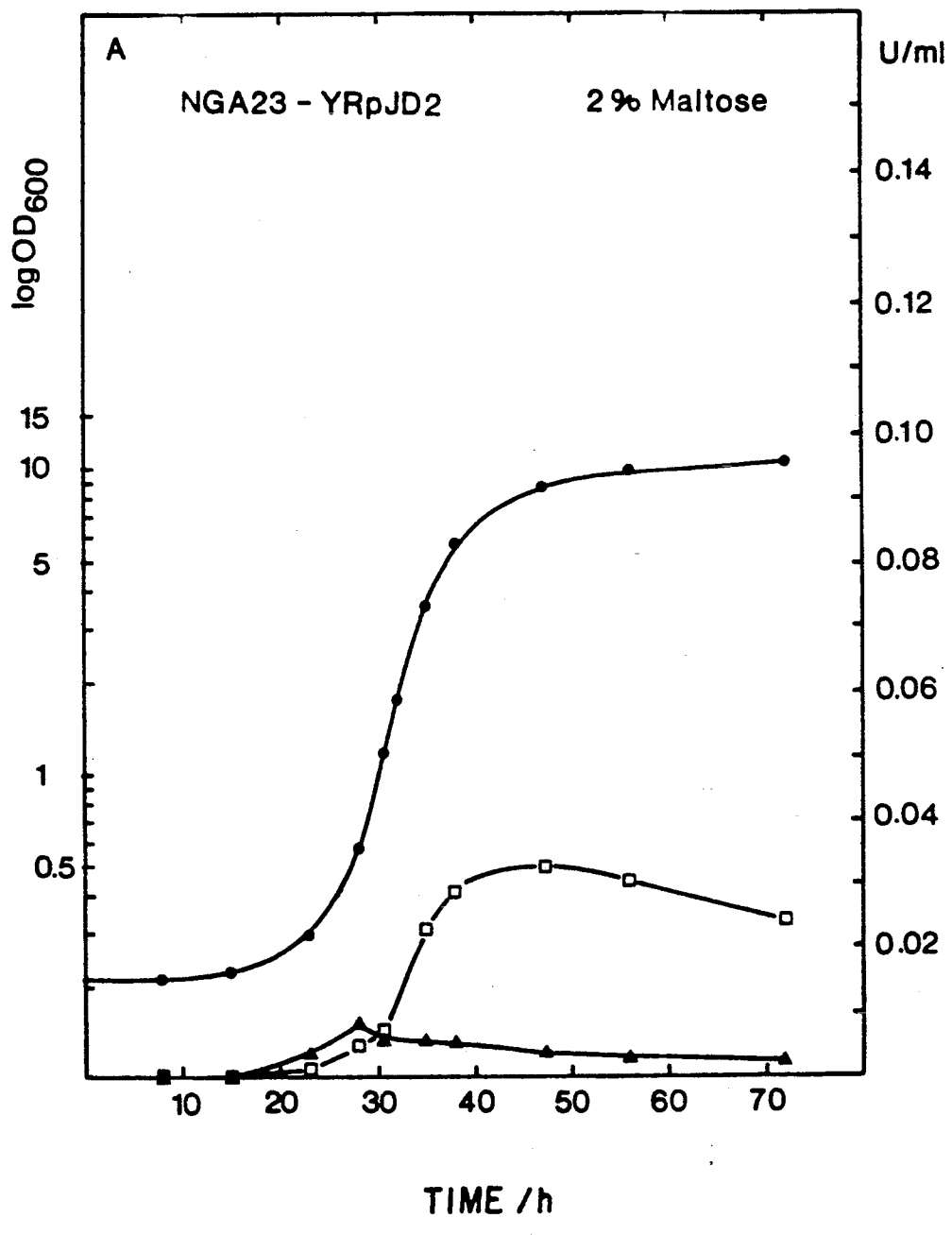
Figure 4B:
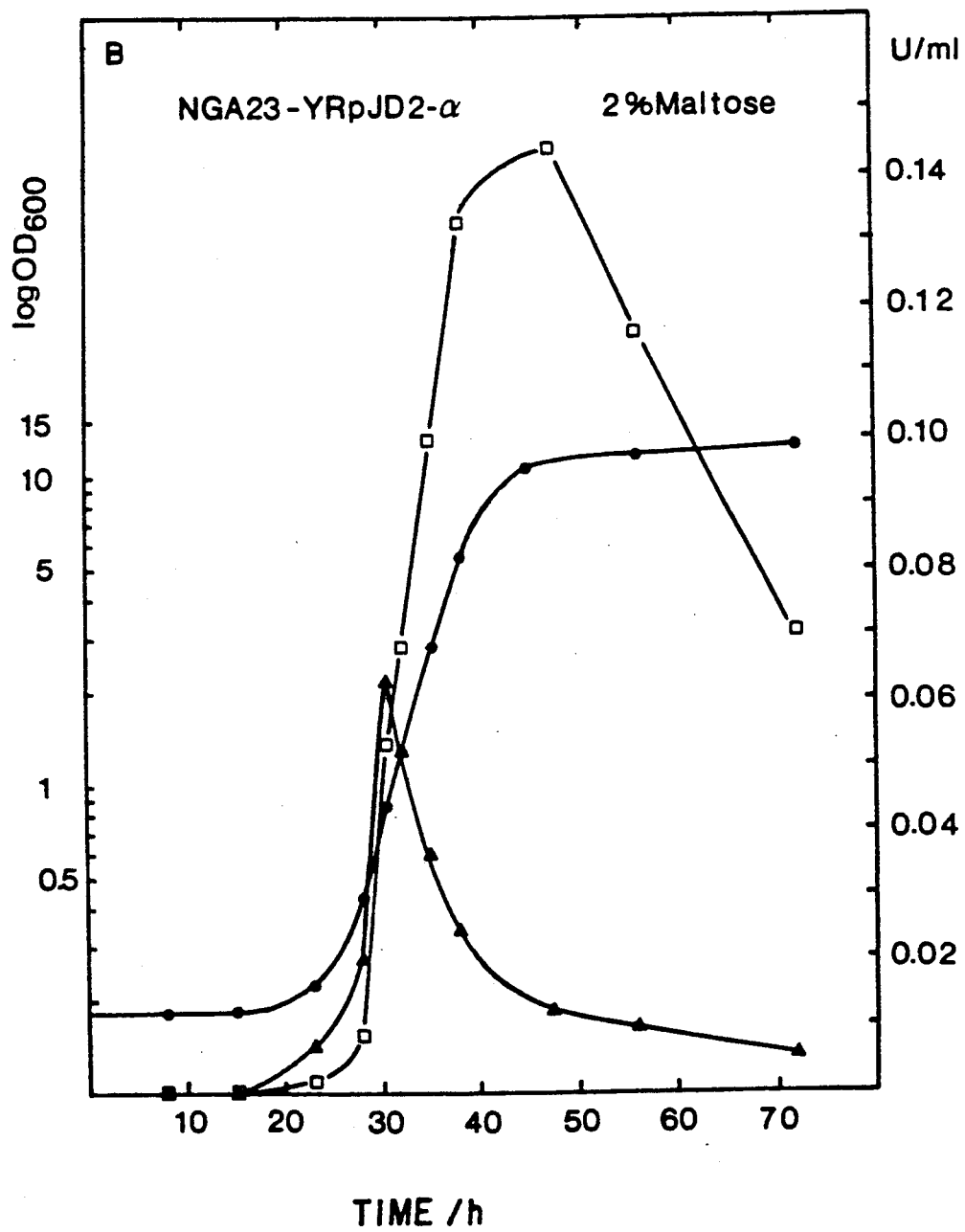

A: Alignment of plasmid pYc1-αderived by insertion of a 5 kb fragment of *S. castellii* DNA, which contains the α-amylase gene, into the cosmid pYc1.

B: Restriction map of the cloned EcoRI fragment of *S. castellii*.

C: Fragments (1, 2 and 3) subcloned into the plasmid pJDB207 do not lead to functional expression of the α-amylase gene in *S. cerevisiae* GRF18 transformants.

D: Sequencing strategy: For sequencing according to Maxam & Gilbert (1980) the EcoRI/SalI fragments were 3' labelled with $^{32}P$-dTTP. The orientation and the extension of the sequencing are indicated by arrows.

FIG. 2

(Parts A–C)

The nucleotide sequence of the 5' end of the α-amylase structural gene and its 5' flanking region.

FIG. 3

Amino acid sequences of 5 isolated tryptic peptides of glucoamylase.

FIG. 4

(Parts A–E)

Secreted α-amylase activity of the transformants in different growth phases.

The cells were grown up overnight in precultures with 0.67% YNB and 4% glucose. After washing the cells with the medium of the different main cultures, the main cultures were inoculated to $O.D._{600}$ of 0.2. The main cultures (1 liter YNB medium with the given carbon sources in Fernbach vessels) of the *S. alluvius* NGA23 transformants were buffered with 0.2M sodium phosphate buffer pH 6.2 and of the *S. cerevisiae* MC34 transformants with 0.1M citrate buffer pH 6.2. The cultures were incubated at 30° C. with constant shaking (2 Hertz) on a longitudinal shaker. The measurements of the α-amylase activity and the glucose concentration in the culture supernatant were determined as described. For further details, see specification.

FIG. 5

FPLC ion exchange chromatography on a Mono Q column for separation of the α-amylase protein from concentrated extracellular medium of *S. cerevisiae* MC34 transformed with pYc1-α.

Using a 10 mM Tris-Cl buffer pH 7.5, the α-amylase could be eluted by an increased NaCl gradient at approximately 300 mM NaCl.

a: $A_{254}$ nm
b: % buffer B
Buffer A: 10 mM Tris-Cl, pH 7.5
Buffer B: 10 mM Tris-Cl, pH 7.5, 2M NaCl

FIG. 6

Analysis of the purified α-amylase protein from extracellular medium of *S. cerevisiae* MC34 transformed with the plasmid pYc1-α by SDS-PAGE.

Lane a: purified α-amylase
Lane b: molecular weight standard proteins myosin from rabbit muscle (205 kd); β-galactosidase from *E. coli* (116 kd); phosphorylase b from rabbit muscle (97 kd); albumin, bovine (66 kd); albumin, egg (45 kd); carbonic anhydrase from bovine erythrocytes (29 kd).

FIG. 7

Thin layer chromatography of starch hydrolysis products.

The α-amylase activity of culture supernatants on soluble starch after 2 hours at 40° C. was additionally characterized and determined by a thin layer chromatography of the reaction products using Kieselgel 60 from Merck. The chromatography was done with 2:2:1 acetone-isopropanol-0.1M lactic acid solvent system. The chromatogram was developed using naphtoresorcinol as described by Touchstone & Dobbins (1978).

FIG. 8

Construction of *S. alluvius* Plasmids

A (Parts 1–5)

a: The plasmid YRp7HIS4 which was isolated from a genomic Sau3A library of *S. castellii* DNA in the plasmid YRp7 (Struhl et al. 1979) by complementation of the his4-519 mutation of *S. cerevisiae* AH22, was digested with BamHI and ClaI and religated. One of the resulting plasmids (YpRHIS4) contains a 1.5 kb BamHI/ClaI fragment from the his4 region of *S. castellii* in YRp7.

b: Deletion of the 1.45 kb ARS1-TRP1-EcoRI fragment from the plasmid YpRHIS4.

c: Insertion of the 5 kb AMY-EcoRI fragment into the plasmid pBRSwARS1.

d: Isolation of the 3.2 kb TRP5-BamHI fragment from the plasmid pYAS1 by preparative gel electrophoresis.

e: Insertion of the 3.2 kb TRP5-BamHI fragment into the plasmids YpRHIS4, pBRSwARS1 and pBRSwARS1-α.

B (Part 6)

The plasmids YRp7TRP5-A and -B were constructed by inserting the 3.2 kb TRP5-BamHI fragment from pYAS1 into YRp7. Plasmids with both orientations (−A and −B) of the fragment were obtained.

C (Part 6)

The plasmids pEK2TRP5-A and -B were constructed by inserting the 3.2 kb TRP5-BamHI fragment from pYAS1 into the *K. lactis* vector pEK2 in both possible orientations (−A and −B).

FIG. 9

Copy Number Estimation of the Plasmid YRpJD2 in *S. alluvius* NGA23 and in *S. cerevisiae* X3656 2D (Part 1)

A: Ethidium bromide stained plasmid and yeast minilysate DNA separated in a 0.7% agarose gel.

B: Autoradiogram after Southernblot and hybridization with nick translated YRpJD1 DNA (48 hours exposition at −70° C.).

(Part 2)

C: Autoradiogramm of lanes j–q after 312 hours exposition at −70° C.

D: Map of the hybridization probe YRpJD1 (thin line: pBR322; open boxes, *S. cerevisiae* DNA; black box, *S. castellii* DNA).

Lanes a–c, control plasmids;
a: YRpJD1 EcoRI
b: YRpJD1 uncleaved
c: YRpJD2 uncleaved.

Lanes d–g, yeast minilysate DNA; d–f, DNA of *S. alluvius* NGA23: YRpJD2 transformants, d and f, cleaved with EcoRI; e and g, uncleaved; h and i, NGA23:YRpJD1 DNA cleaved with EcoRI (h) and uncleaved (i); j and k, DNA of untransformed NGA23 cleaved with EcoRI (j) and uncleaved (k); l and m, DNA of a *S. cerevisiae* X3656 2D: YRpJD2 transformant cleaved with EcoRI (l) and uncleaved (m); n–q, DNA of untransformed X3656 2D cleaved with EcoRI (n and p) and uncleaved (o and q).

FIG. 10

Copy Number Estimation of Different Plasmids in *S. alluvius* NGA23.

(Part 1)

A: Ethidium bromide stained EcoRI fragments of control plasmids and yeast minilysate DNA after separation in a 0.7% agarose gel.

B: Autoradiogram after Southern blot and hybridisation with nick translated YRp7HIS4 DNA (15 hours exposition at −70° C.).

(Part 2)

C: Autoradiogram after 6 hours (lanes a–d) and after 125 hours (lanes e–p) exposition at −70° C. respectively (faint bands in lanes j and m and the position of the bands of the chromosomal HIS4 locus are indicated by arrows).

D: Scheme of the homologies of YRpJD1 and the choromosomal Schwanniomyces HIS4 region to the hybridization probe YRP7HIS4.

lanes a–e, control plasmids: a, pEK2TRP5-A; b, YRp7TRP5-A, c, pYAS1; d, YRpJD1; lane e, DNA of untransformed *S. alluvius* NGA23; lane f, DNA of untransformed *S. castellii* 26076; lanes g–p, DNA of *S. alluvius* NGA23 transformed with: g, YRpJD1; h and j, YRp7TRP5-A; i, k and l, YRp7TRP5-B; m, pEK2TRP5-A; n, pEK2TRP5-B; o and p, pYAS1 (DNA in lane o is uncleaved).

FIG. 11

Comparison of the Copy Number of SwARS1 and ARS1 plasmids in *S. alluvius* and *S. cerevisiae*

(Part 1)

A: Ethidium bromide stained EcoRI fragments of control plasmids and yeast minilysate DNA after separation in a 0.7% agarose gel.

(Part 2)

B: Autoradiogram after Southern blot and hybridisation with nick translated YRpJD2-αDNA. The position of the 2.0 kb band of the chromosomal *S. cerevisiae* TRP5 locus is indicated by an arrow.

lanes a–d, control plasmids: a, pCJD5-1; b, YRpJD2-α; c, YRpJD1; d, YRp7TRP5-A;

lanes e–h, DNA of *S. alluvius* NJD1; e, f and i, untransformed; g, transformed with pCJD5-1; h, transformed with YRpJD2;

lanes j–m, DNA of *S. alluvius* NGA23; j, untransformed; transformed with: k, YRpJD2-α; l, YRpJD2; m, YRpJD1;

lanes n–r, DNA of *S. cerevisiae* X3656 2D, transformed with: n, YRpJD2-α; o, YRpJD2; p, YRpJD1; q, YRp7TRP5-A; lane r, untransformed.

FIG. 12

In Vivo Labelling of Extracellular Proteins from *S. alluvius* NGA23 Transformants.

The transformants were grown under repressed and induced conditions (see FIGS. 4a, b and c) in 1 ml culture after addition of 100 μCi $^{35}$S-methionine (800 Ci/mmol). After incubation at 30° C. for different times (18, 22, 28, 43 and 90 hours) 30 μl of the cell-free supernatant were analysed by SDS-PAGE and autoradiography.

a, NGA23: YRpJD2 in YNB, 2% glucose (repressed);

b, NGA23: YRpJD2 in YNB, 2% maltose (induced);

c, NGA23: YRpJD2-α in YNB, 2% glucose repressed);

d, NGA23: YRpJD2-α in YNB, 2% maltose (induced).

The positions of the molecular weight standard proteins (see FIG. 6) are indicated by arrows.

Figure 13:
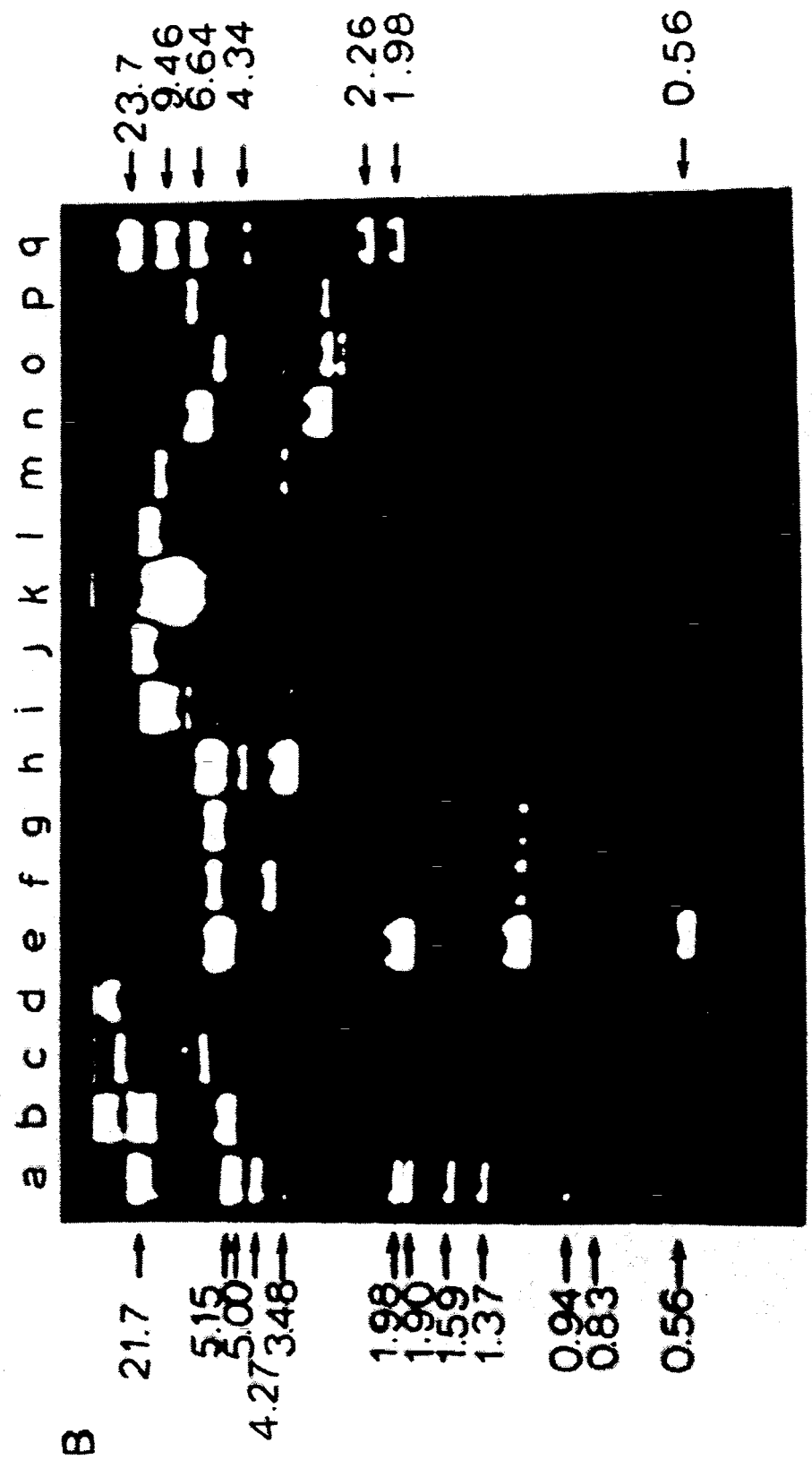

FIG. 13(1) and 13(2)

Restriction Map and Restriction Analysis of the Cosmids pCJD5-1 and pCJD5-2

(Part 1)

A: Restriction map (Part 2)

B: Restriction fragments separated in a 0.7% agarose gel lane a, lambda DNA cleaved with EcoRI and HindIII;

lane q, lambda DNA cleaved with HindIII;

from left to right:

plasmids YRpJD2, pCJD5-1, pCJD5-2:

lanes b, c, d, cleaved with EcoRI;

lanes h, i, j, cleaved with BamHI;

lanes k, l, m, cleaved with BglII;

lanes n, o, p, cleaved with PvuII.

FIG. 14

Restriction Map of the Plasmid pKARS2-α

The 5 kb AMY-EcoRI fragment from plasmid pYc1-α was inserted into the single EcoRI site of the plasmid pKARS2-d.

FIG. 15

(Part 1)

A: Restriction map of the two subcloned fragments containing the functional glucoamylase gene (AMG).

(Parts 2 and 3)

B: The AMG fragments were subcloned into the *S. alluvius*-*S. cerevisiae* vector pCJD5-1 resulting in pCJD5-AMG1 and pCJD5-AMG2, into the *S. cerevisiae*-*S. pombe* vector pJDB207 resulting in pJDB207-AMG1 and pJDB207-AMG2, and into the *K. lactis* vector pEK2, resulting in PEK2-AMG2.

FIG. 16

Inactivation of glucoamylase at different temperatures.

FIG. 17

(Parts A–E)

The nucleotide sequence of glucoamylase structural gene and flanking regions.

TABLE I

| Comparison of preferred codon usage in *S. cerevisiae* and *Schwanniomyces castellii*. | | |
|---|---|---|
| amino acid | preferred codons in *S. cerevisiae* | preferred codons in *S. castellii* |
| ala | GCU, GCC | GCU, GCG |
| ser | UCU, UCC | UCA, UCC, AGC, UCU, AGU (no clear preference) |
| thr | ACU, ACC | ACU, ACC, ACA |

TABLE I-continued

Comparison of preferred codon usage in S. cerevisiae and Schwanniomyces castellii.

| amino acid | preferred codons in S. cerevisiae | preferred codons in S. castellii |
|---|---|---|
| val | GUU, GUC | GUU, GUA, GUC, GUG |
| ile | AUU, AUC | AUU, AUC, AUA, AAU (no clear preference) |
| asp | GAC | GAU, SAC |
| phe | UUC | UUC, UUU (no clear preference) |
| tyr | UAC | UAU, UAC |
| cys | UGU | UGU |
| asn | AAC | AAU, AAC |
| his | CAC | CAU, CAC |
| glu | GAA | GAA, GAG |
| gly | GGU | GGU, GGA |
| gln | CAA | CAA |
| lys | AAG | AAA |
| pro | CCA | CCA, CCU |
| leu | UUG | UUG, UUA, CUU |
| arg | AGA | AGA |

TABLE II

Transformation frequencies obtained with the modified method for strains of different yeast genera.

| Species | Strain | Plasmid | Replicator | Marker | Transformants per μg DNA |
|---|---|---|---|---|---|
| S. alluvius | NGA19 | YRpJD1 | SwARS1 | TRP5 | 300–1000 |
| S. alluvius | NGA23 | YRpJD1 | SwARS1 | TRP5 | 300–1000 |
| S. alluvius | HTR36 | YRpJD1 | SwARS1 | TRP5 | 300–1000 |
| S. cerevisiae | AH22 | YRp7HIS4 | ARS1 | HIS4 | 500–2000 |
| S. cerevisiae | X3656 | YRpJD1 | ARS1 | TRP5 | 500–2000 |
| S. cerevisiae | X3656 | pYAS1 | 2 μm | TRP5 | 1000–10000 |
| S. cerevisiae | GRF18 | pYc1 | 2 μm | HIS3 | 200–1000 |
| K. lactis | SD11 | pEK2 | KARS2 | TRP1 | 500–1000 |
| H. polymorpha | LR9 | pHARS1 | HARS1 | URA3 | 500–1500 |
| S. pombe | leu1-32 | pJDB207 | 2 μm | LEU2 | 1–10 |

TABLE III

Transformation frequencies, mitotic stabilities and copy numbers in S. alluvius NGA23

| Plasmid | Origin of replication | Trp+-transformants per μg plasmid DNA | Trp+-colony forming cells in selective medium | Trp+-colony forming cells after 15 generations in selective medium | Average copy number per cell | Copy number per Trp+-colony forming cell |
|---|---|---|---|---|---|---|
| pYe(trp5)1-53 | — | 0.1–0.2 | 6% | 0% | 0.1–0.2 | 2–3 |
| YRp7-TRP-A | ARS1 | 5–20 | 10% | 1% | 0.2–1 | 2–10 |
| YRp7-TRP-B | ARS1 | 5–20 | 10–20% | 1% | 0.2–1 | 1–10 |
| pEK2-TRP-A | ARS1, KARS2 | 5–20 | 9% | 1% | 0.2–0.5 | 2–5 |
| pEK2-TRP-B | ARS1, KARS2 | 5–20 | 11% | 1% | 0.2–0.5 | 2–5 |
| pYAS1 | 2 μm | 50–100 | 75–90% | 5–10% | 2–3 | 2–4 |
| YRpJD1 | ARS1, SwARS1 | 300–1000 | 85–95% | 10–20% | 5–10 | 6–12 |

TABLE IV

Transformation frequencies, mitotic stabilities and average copy number of the plasmids YRp7-TRp5, YRpJD1 and YRpJD2 in S. alluvius NGA23 and S. cerevisiae X3656.

| Plasmid | Origin | Transformants per μg DNA | | loss of plasmids after 15 generations in non-selective medium | | average copy number per cell | |
|---|---|---|---|---|---|---|---|
| | | S. all. NGA23 | S. cer. X3656 | S. all. NGA23 | S. cer. X3656 | S. all. NGA23 | S. cer. X3656 |
| YRp7-TRP5-A | ARS1 | 5–10 | 500–2000 | 99% | 80–90% | 0.2–1 | 5–10 |
| YRpJD1 | ARS1, SwARS1 | 300–1000 | 500–2000 | 80–90% | 80–90% | 5–10 | 5–10 |
| YRpJD2 | SwARS1 | 300–1000 | 500–2000 | 80–90% | 80–90% | 5–10 | 5–10 |

The yeast strains used are as follows:
Schwanniomyces castellii ATCC 26076. (DSM 3794)
Schwanniomyces alluvius NGA23 and NGS1. (DSM 3792 and 3793)
Kluyveromyces lactis SD11. (DSM 3795)
Schizosaccharomyces pombe leu1-32, his5-303. (DSM 3796)
Saccharomyces cerevisiae GRF 18 leu2-3, leu2-112, his3-11, his3-15. (DSM 3797)
Saccharomyces cerevisiae AH22a leu2-3, leu2-112, his4-519, can1. (DSM 3820)
Saccharomyces cerevisiae X3656 2D a, ade, arg4-1, his6, leu1, trp5. (DSM 3798)
Saccharomyces cerevisiae his3 Mal1[30] (DSM 3799)

The Escherichia coli strains used are as follows:
Escherichia coli, HB101 F−, hsd S20, $r_B^- m_B^-$, recA13, ara-14, proA2, lacY1, galK2, rpsL20 (Sm$^r$), xy15, mtl-1, supE44, λ− (DSM 3788)
Escherichia coli JA221, recA-1, leuB6, trpE5, hsdR−, hsdM+, lacY1. (DSM 3789)
Escherichia coli BHB2688, N205 recA−[imm$^{434}$, cIts, b2, red$^3$, Eam4, Sam7]/λ (DSM 3790)
Escherichia coli BHB2690, N205 recA−[imm$^{434}$, cIts, b2, red$^3$m, Dam15, Sam7]/λ (DSM 3791)

The plasmids and cosmids used are as follows:
Cosmid pYC1.
Plasmid pEK2.
Plasmid YRP7.
Plasmid pJDB207.

As far as they are essential for carrying out the present invention, microorganisms as mentioned above have been deposited with the Deutsche Sammlung für Mikroorganismen (DSM).

A complete medium for yeast strains was YEPD (2% bactopeptone, 1% yeast extract, 2% glucose). Minimal medium contained 2% glucose and 0–67% yeast nitrogen base without amino acids (Difco) supplemented with the appropriate amino acids.

Schwanniomyces cells were grown in 2% soluble starch instead of glucose.

Starch fermenting yeast strains were screened for α-amylase and hence halo formation on YNB minimal medium plates containing 1% glucose, 1% soluble starch and 2% agar. The halos were developed by incubating the plates in an iodine saturated chamber for a few seconds.

Bacterial cells were grown in LB medium (0.5% yeast extract, 1% tryptone, 1% NaCl). When required, ampicillin was added to a final concentration of 150 μg per ml, tetracycline to 20 μg per ml, respectively.

Bacterial transformation was carried out as described by R. W. Davis et al. (1980).

Yeast transformations were performed according to the procedure described in this paper.

Throughout this application, various publications are referenced by the name of the author and date of publication within parantheses. Full citations for these references may be found at the end of the specification as an annex, listed in alphabetical order immediately preceding the claims. The disclosures of these publications in their entireties are hereby incorporated by reference into this application in order to more fully describe the state of the art as known to those skilled therein as of the date of the invention described and claimed herein.

Plasmid DNA was purified either by CsCl gradients centrifugation (Maniatis et al., 1982) or by rapid alkaline extraction of plasmid DNA as described by Birnboim and Doly (1979).

Yeast crude extracts were prepared by the method of Schatz (1979).

Yeast minilysates were prepared by the method of Sherman et al. (1983).

DNA fragments were isolated by "low melting agarose" procedure as described by Gafner et al. (1983).

Methods Used for Carrying Out the Invention

DNA sequencing was carried out as described by Maxam and Gilbert (1980). DNA was nick translated according to Rigby et al. (1977).

Southern hybridization was carried out as described by Southern (1975).

Restriction endonucleases, T4 DNA ligase, *E. coli* polymerase I, Klenow polymerase can be purchased from Boehringer (Mannheim) and used as specified by the suppliers. α-$^{32}$P dNTPs and ($^{35}$S) methionine can be purchased for example from Amersham. Zymolyase 5,000 and zymolyase 60,000 can be obtained from Kirin Brew (Japan). Nitrocellulose filters can be obtained from Schleicher and Schüll.

The cosmid library of *Schwanniomyces castellii* DNA was constructed in the *Saccharomyces cerevisiae* shuttle vector pYc1 (Hohn and Hinnen, 1980) and in the *Saccharomyces cerevisiae-Schwanniomyces alluvius-E. coli* shuttle vector pCJD5-1 constructed according to this invention as described by Ish Horowicz and Burke (1981).

Protein concentration was determined by the method of Bradford (1976) with bovine serum albumin used as a standard. The protein was separated by SDS polyacrylamide gel electrophoresis according to the procedure of Laemmli (1970).

Amylase activity was measured kinetically with an enzymatic colour test, for example, α-amylase Mercko test, from Merck. The rate of formation of 2-chloro-4-nitrophenol is determined by photometry at 405 nm at 37° C. in 0.1M potassium phosphate activity in the sample material.

Enzyme units (U) are defined as the amount of enzyme catalysing the formation of 1 μmol 2-chloro-4-nitrophenol×min$^{-1}$ at 37° C.

Glucoamylase activity was measured by a stop assay method: After incubation of the sample in 10% soluble starch in 0.05M KH$_2$PO$_4$-NaOH (pH 5.0) at 50° C. The amount of glucose produced is determined by the glucose dehydrogenase method (system glucose Merck). The quantity of NADH formed is proportional to the glucose concentration.

The enzyme unit (U) is defined as the amount of enzyme catalyzing the formation of 1 μmol glucose min$^{-1}$ at 50° C.

Isolated α-amylase from culture supernatant of *Schwanniomyces castellii* forms a halo on agar plates containing soluble starch after staining with iodine. From these observations, the scheme to clone the α-amylase was based on the assumption that *Saccharomyces cerevisiae* cells which form no halo can be converted to halo-forming ones when a plasmid vector containing the gene for a starch hydrolysing enzyme, namely α-amylase, is present. To clone the α-amylase gene, a recombinant cosmid library was constructed from genomic DNA of *Schwanniomyces castellii* ATCC 26076. Using the cosmid cloning technique described above, a genomic library of about 17,000 independent clones could be generated in the vector pYc1 (Hohn and Hinnen, 1980). The cosmid library was screened for inserts containing the α-amylase gene by transforming *Saccharomyces cerevisiae* GRF18 to histidine prototrophy and checking for the ability to degrade starch.

Approximately 4500 transformants of GRF18 were screened for their ability to form halos after iodine staining on plates containing leucine, glucose and soluble starch. 13 halo-forming transformants were obtained. From these transformants, total yeast DNA was isolated and used to transform *E. coli* JA221 cells with selection for ampicillin resistance. Two different recombinant cosmids containing a 32 kb and a 39 kb fragment of *Schwanniomyces castellii* DNA respectively were obtained. These recombinant cosmids were reintroduced into GRF18. The transformants showed the His+ and halo-forming phenotype. In a mitotic stability test (Beggs, 1978) both cosmid markers, the HIS3 and the halo-forming function, were segregated out simultaneously, indicating that both genes were present on the cosmid.

The smaller cosmid containing the 32 kb insert was used to identify the DNA region responsible for the halo-forming phenotype. To achieve this, the cosmid was digested with EcoRI, religated and transformed into JA221. The DNA from ampicillin resistant *E. coli* cells was used to transform GRF18 with selection for histidine prototrophy.

From five halo-forming transformants, total yeast DNA was isolated and used to transform JA221. Plasmid DNA was isolated from ampicillin resistant *E. coli* transformants. Restriction enzyme analysis revealed that each of these plasmids carries a 5 kb EcoRI *Schwanniomyces castellii* DNA fragment in the original vector pYc1. This plasmid is called pYc1-α (FIG. 1A). The restriction map of the 5 kb EcoRI fragment is presented in FIG. 1B.

Fragments 1, 2 and 3 (FIG. 1C), subcloned into the vector pJDB207 (Beggs, 1981) and transformed into *Saccharomyces cerevisiae* GRF18 did not result in α- amylase secreting transformants and hence do not contain the functional gene. Therefore, it can be assumed that the functional α-amylase gene spans the HindIII, BgIII sites.

Taking into account that the molecular weight of α-amylase is approximately 61,000 daltons (Wilson et al., 1982), it can be predicted that a DNA fragment of approximately 2 kb should contain the functional gene.

To verify this assumption, DNA sequence analysis was performed according to Maxam and Gilbert (1980). For sequencing both EcoRI-SalI fragments of the 5 kb EcoRI fragments were radioactively labelled at the SalI site (FIG. 1D). DNA sequence analysis revealed a 5' noncoding region followed by an open reading frame spanning the SalI site. The DNA sequence is presented in FIG. 2.

The TATA box (Gannon et al., 1979) usually located 25–32 bp upstream and the CAAT box (Benoist et al., 1980) which has been found about 80 bp upstream from the transcription initiation point, are thought to be important for transcription initiation. While the TATA box is present in almost all examined genes, the CAAT box is not always present.

In the regulation region of the α-amylase gene there is a perfect TATA box at −89 and a CAAT box at −115.

In the 5' region of the α-amylase gene, there is a CAAG sequence at position −7. The codon usage of the α-amylase is given in Table I.

Expression of the Schwanniomyces α-Amylase Gene and Secretion of the Protein by *Saccharomyces cerevisiae*

GRF18:pYc1-α transformants are not able to grow on soluble starch as a sole carbon source. This could be shown to be due to a defect in maltose utilisation. Therefore, the plasmid pYC1-α was used to transform *Saccharomyces cerevisiae* MC34 (his3), having a Mal+ phenotype with selection for starch degradation. All histidine phototroph transformants were able to grow on starch as a sole carbon source and could form halos surrounding the colony after staining with iodine. For α-amylase activity measurements, MC34:pYc1-α transformants were cultivated with selection for histidine prototrophy in YNB medium containing glucose.

During the growth of *Saccharomyces cerevisiae* in unbuffered YNB medium, the pH drops to approximately 3.5.

The α-amylase becomes inactivated below a pH of 4 and has a pH optimum at about 6.2 (Sills and Stewart, 1984). Therefore, the medium was buffered with 0.1M citrate buffer pH 6.2.

Figure 4C:
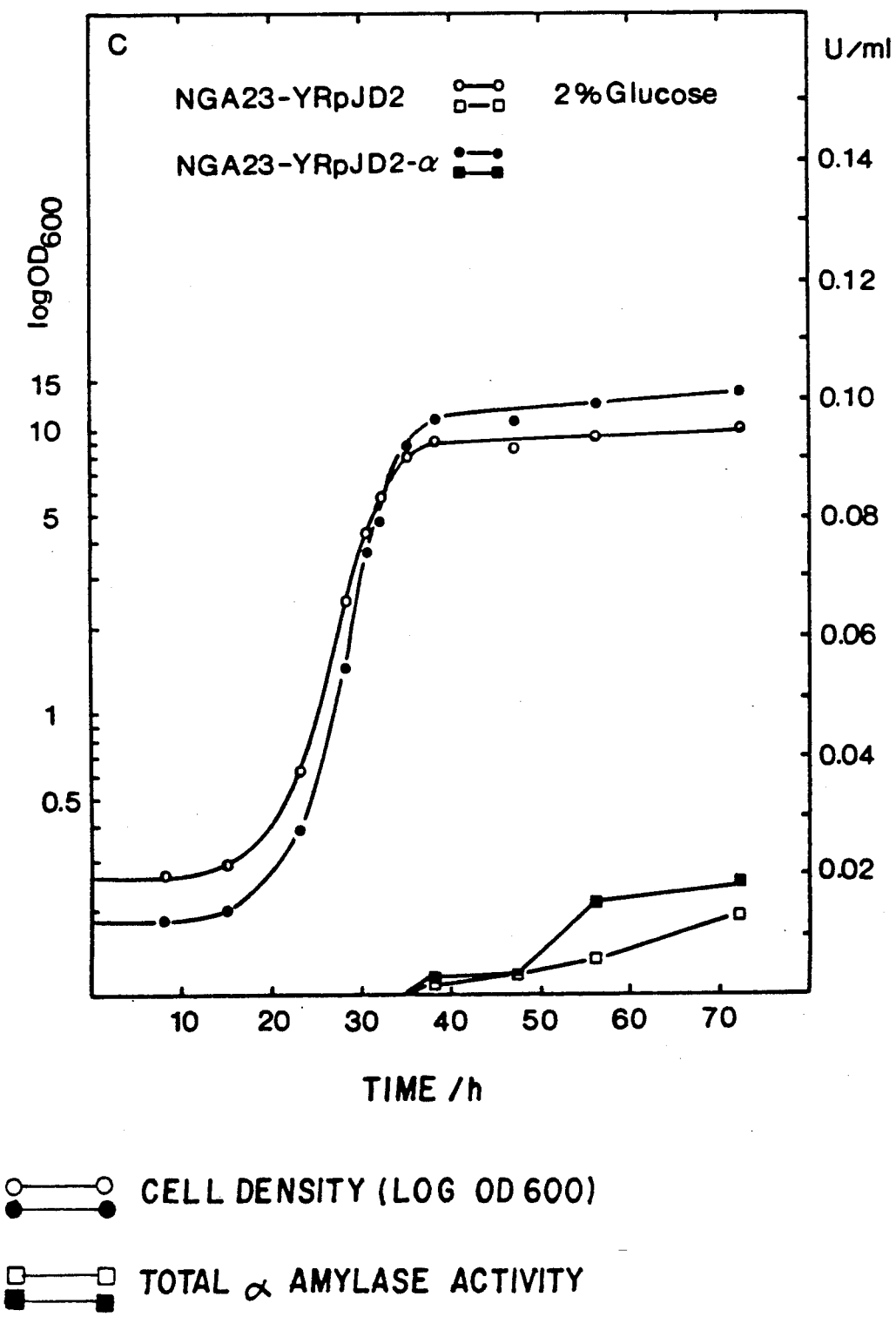
Figure 4D:
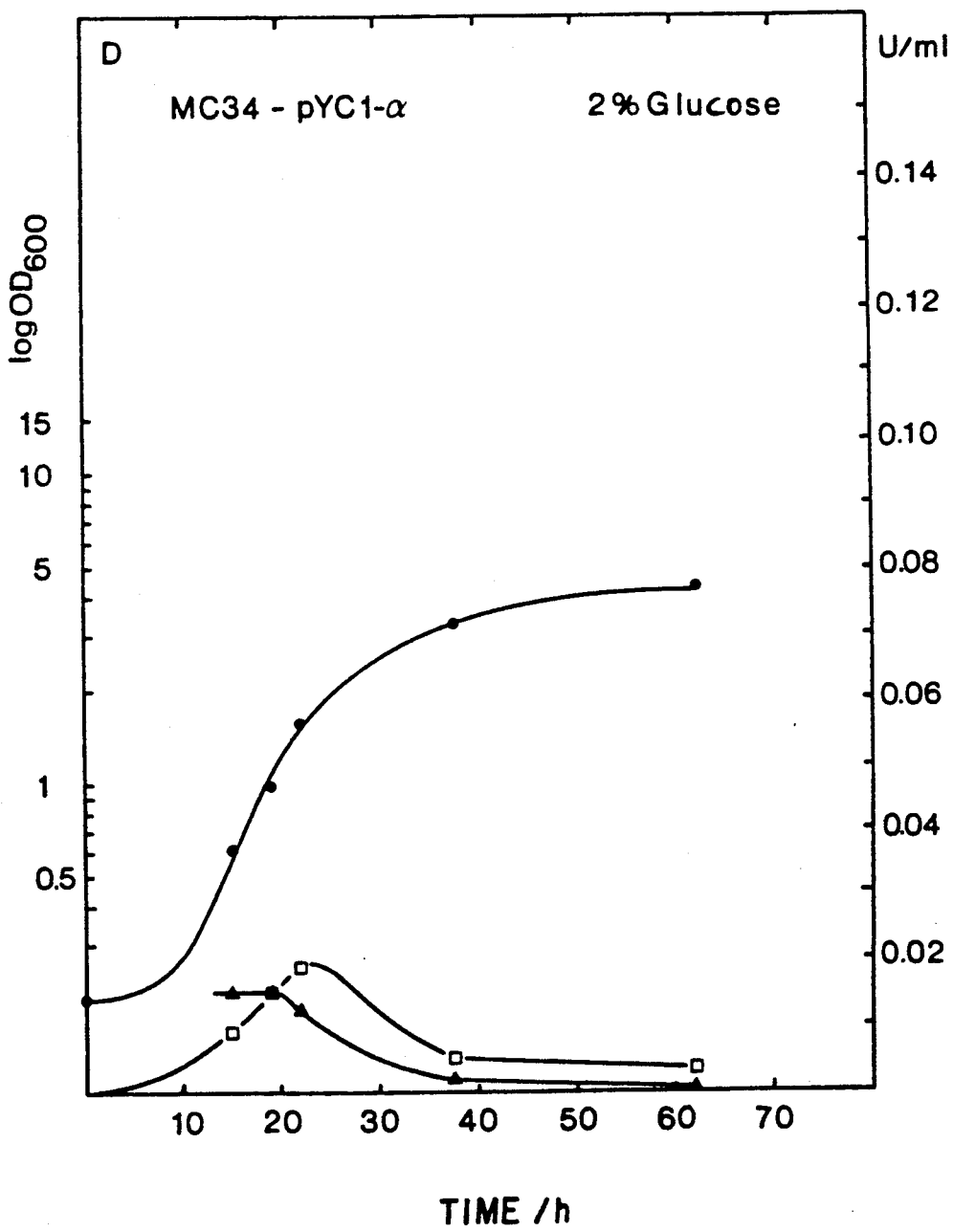

During growth of MC34:pYc1-α, crude extract and extracellular medium was assayed for α-amylase activity.

α-amylase activity could only be detected in the extracellular culture medium and not in crude extracts, indicating that the α-amylase is secreted. The total activity in the extracellular medium decreases at late logarithmic growth (FIG. 4D). This loss of enzymatic activity could be explained by proteolytic degradation of α-amylase, because proteolytic activities accumulate during the transition from the logarithmic to stationary growth phase (Ferguson et al., 1973). However the stability of α-amylase could not be improved by adding the protease inhibitor PMSF. It can therefore only be concluded that the inactivation is not due to a serin protease.

The total α-amylase activity in the extracellular medium of stationary grown MC34:pYC1-α cells in complete medium YEPD was significantly higher, compared to cells grown in YNB medium. The most likely explanation is the two-fold higher proteolytic activities when *Saccharomyces cerevisiae* is grown in YNB, compared to growth in YEPD (Tsai et al., 1973).

Sometimes enzymes can be stabilized by the addition of substrate (Katsunuma et al., 1972). MC34:pYc1-α transformants which are grown in YNB containing soluble starch as a sole carbon source showed no difference in the α-amylase activity profile during different growth phases, compared to cells grown in glucose as a sole carbon source, indicating that the α-amylase could not be stabilized in the presence of substrate.

However, it was observed that MC34:pYc1-α had an initial lag period in its ability to ferment starch either by an induction period at maltose uptake or probably due to a time dependent accumulation of secreted α-amylase into the medium. From the recent investigations, it could be shown that the α-amylase gene is also expressed and the gene product secreted by *Schizosaccharomyces pombe* and *Kluyveromyces lactis*. For this purpose, *Schizosaccharomyces pombe* was transformed with plasmid pYcIα (FIG. 1) and *Kluyveromyces lactis* with plasmid pKARS2-α (FIG. 14a). The former transformants could form halos on starch plates after iodine staining. Quantification of the α-amylase system by these two transformed yeast strains is the subject of the present investigation.

Moreover, the α-amylase gene was cloned into a wild type bottom-fermenting brewers' yeast strain of *Saccharomyces cerevisiae* var. *carlsbergensis* by transformation with the plasmid containing α-amylase gene (pYC1-α) and screening for α-amylase activity by halo formation on plates containing soluble starch.

Isolation and Characterisation of the Enzymes α-amylase and glucoamylase from *Schwanniomyces castellii*

Both enzymes were isolated from the medium of a continuous culture of *Schwanniomyces castellii*.

Medium: YNB+1% starch; 20 mM PO4; pH 6.3.
Conditions: temp.=30° C.; PO2=70%; D=0.15 h$^{-1}$.

Yeast cells were separated from the medium by ultrafiltration (UF) and the filtrate was concentrated with an UF-membrane, cut-off 10,000 D. The concentrated filtrate was loaded on a DEAE-Sephacel column in 20 mM phosphate buffer, pH 5.6.

Glucoamylase was eluted from the column between 150–180 mM NaCl, α-amylase was eluted between 180–250 mM NaCl. Fractions containing enzyme activity were collected, dialysed against 100 mM Ammonium acetate buffer pH 6.5 and concentrated by Amicon YM 10 filtration.

Aliquots of ±4 mg of each protein were further purified using HPLC gel permeation chromatography on a TSK 2000 SW column using 100 mM ammonium acetate buffer pH 6.5.

The enzymes purified in this way were tested for homogeniety by SDS-PAGE, resulting in one single protein band for each enzyme.

Preparation of glucoamylase Peptide Fractions

Glucoamylase (50 mg) was incubated with trypsine (1 mg) for 24 hr., 37° C. in 50 mM ammonium acetate buffer pH 6.5, resulting in ±30% breakdown of the enzyme. Peptides were separated by means of HPLC on a TSK 2000 SW column and further purified on RPHPLC using C18 and C8 columns. Elution was carried out with a gradient system 0–100% acetonitrile. From 5 peptides, the amino acid sequence was determined (see FIG. 3).

Characterisation of glucoamylase

Figure 16:
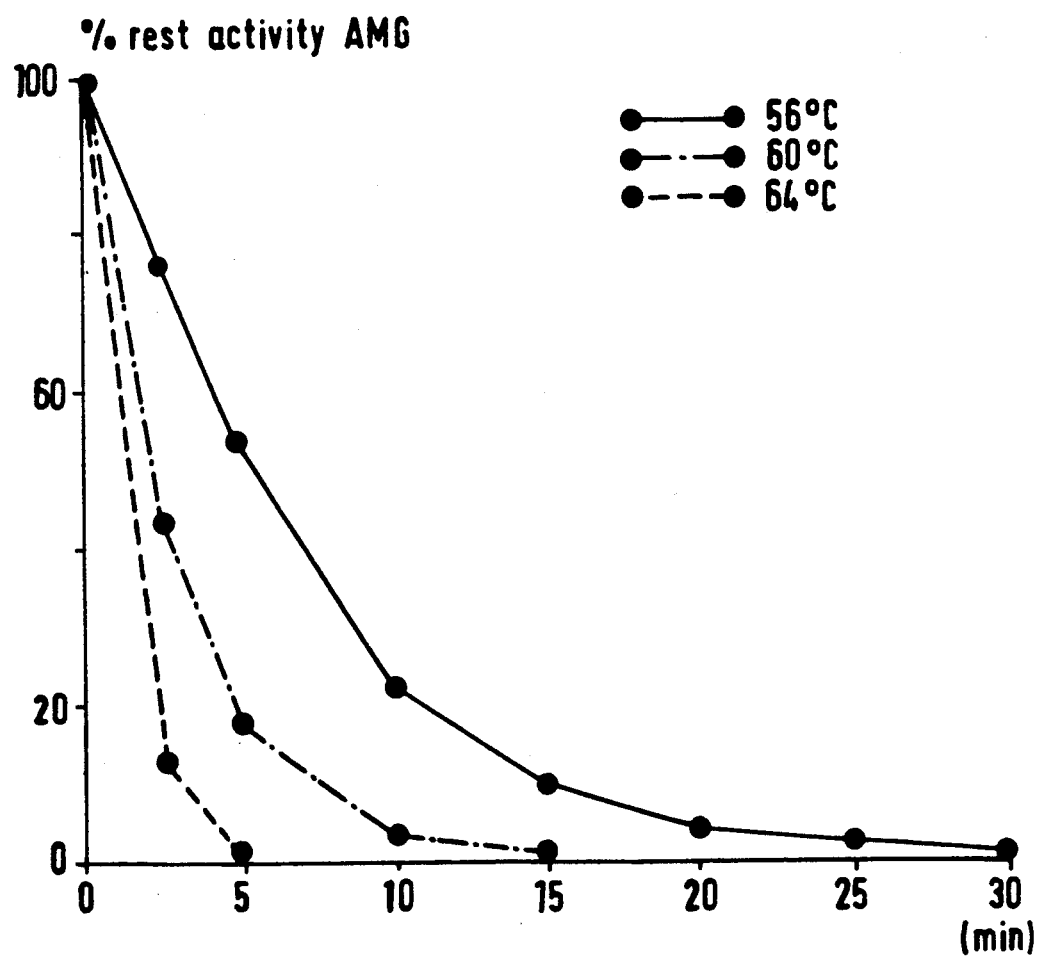

| MW: | 120,000 D |
|---|---|
| pH optimum | 5.0 |
| temp. optimum | 50° C. |
| Km: | 1.0–1.5% dextrin (Serva) |
| pI | 3.6 |
| glycosilated | |
| activity repressed by glucose | |
| temp. inactivation - see FIG. 16. | |

Characterisation of α-amylase

| MW | 53,000 D |
|---|---|
| pH optimum | 6.0 |
| temp. optimum | 37° C. |
| Km: | 0.004–0.7% soluble starch |

Isolation of Secreted α-amylase from *Saccharomyces cerevisiae*

The maximal measurable secreted α-amylase activity from MC34:pYc1-transformants growing in YNB medium could be obtained from cells of the early logarithmic phase (FIG. 4D). It is advantageous to isolate the α-amylase from extracellular YNB medium instead of complex medium containing yeast extract and bactopeptone, because the initial specific activity (α-amylase activity/protein ratio) is significantly higher in YNB than in YEPD.

In addition, since the amount of secreted α-amylase is directly correlated to the amount of actively growing yeast cells, a stepwise growth of MC34:pYc1-α in YNB (selection on the plasmid), YEPD (optimal growth condition), and finally YNB (secretion of α-amylase from a high amount of actively growing cells) was used for the isolation of secreted α-amylase. In detail, the transformants were grown in YNB medium containing glucose. When an optical density of approximately 4 at 600 nm was reached (late logarithmic growth phase), the cells were harvested by centrifugation and resuspended in prewarmed (30° C.) YEPD to a final OD$_{600}$ of 7.5.

Figure 5:
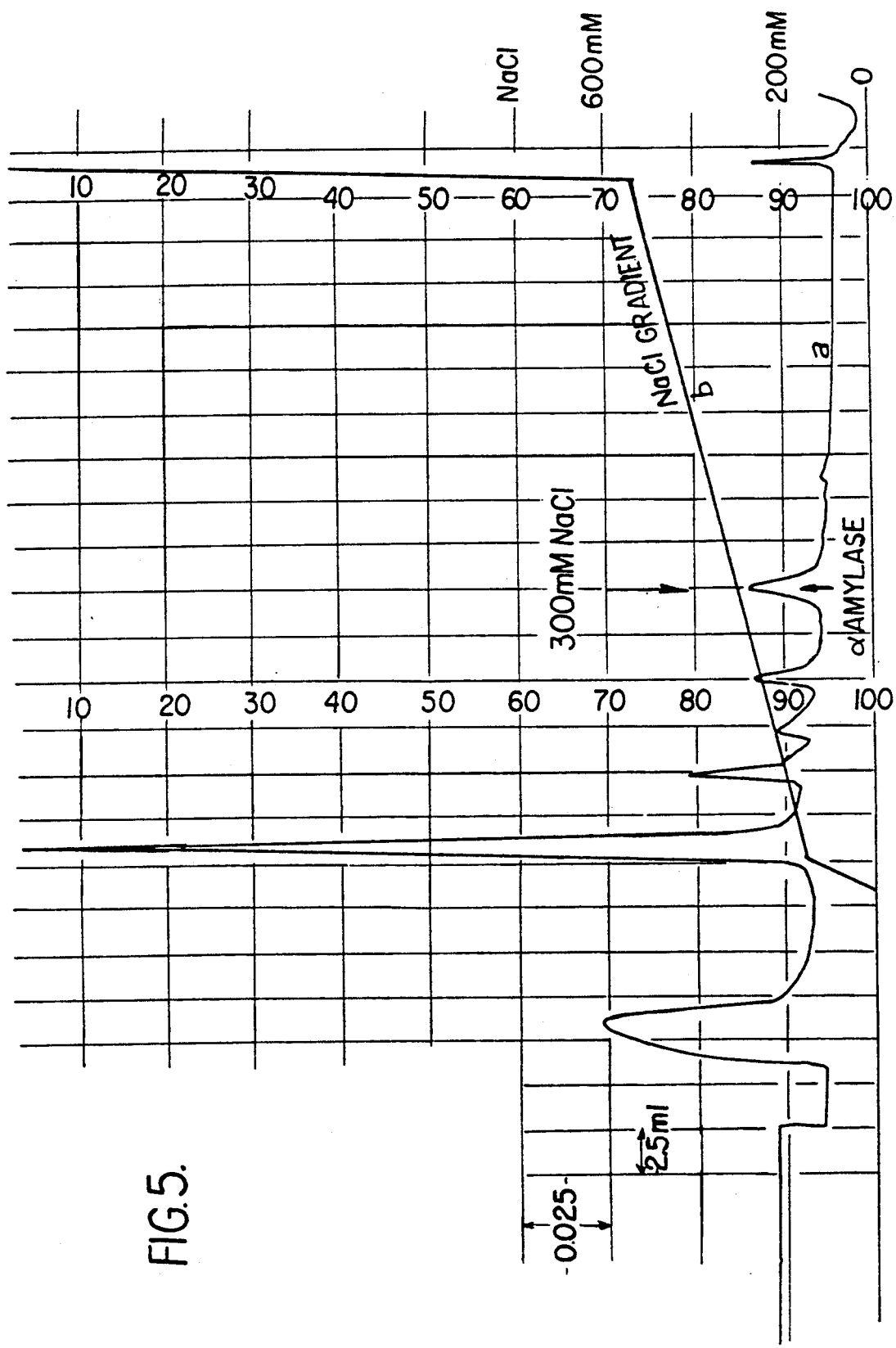

After 2 hours growth at 30° C., the cells were sedimented and resuspended in the same volume of prewarmed (30° C.) YNB containing glucose and 0.1M citrate buffer pH 6.2. After 4 hours incubation at 30° C. (optical density at 600 nm reached a value of 17), the α-amylase was purified from concentrated extracellular medium by means of FPLC ion exchange chromatography using a Mono Q column (Pharmacia). The α-amylase protein could be eluted in 10 mM Tris-Cl, pH 7.5 at 300 mM NaCl using an increasing NaCl gradient (FIG. 5).

Figure 6:
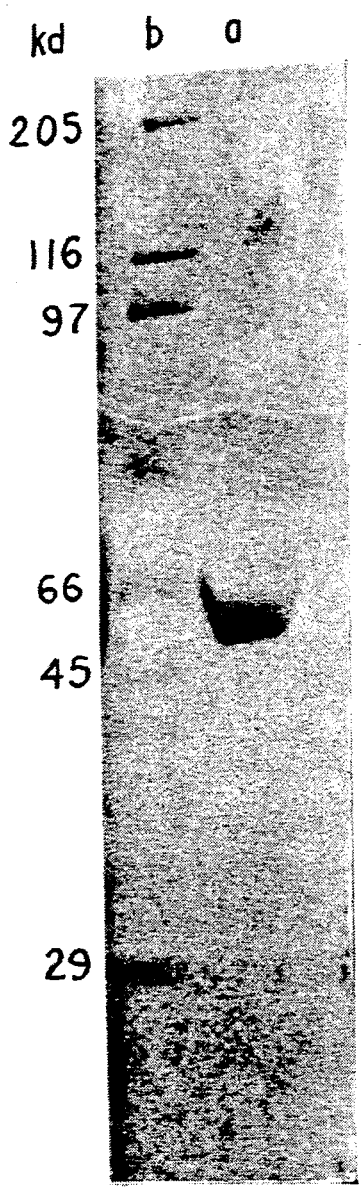

The active protein fraction was concentrated by lyophilisation and analyzed by SDS polyacrylamide gel electrophoresis (FIG. 6). The presence of only one band with a molecular weight of about 55,000 D showed that the α-amylase protein was highly purified by this procedure.

For enzyme characterization, the products of starch degradation by the isolated α-amylase were analysed by thin layer chromatography (FIG. 7). The products of starch hydrolysis are maltose and large amounts of maltotriose and higher oligosaccharides. Glucose is not produced in detectable amounts. This is in agreement with the above mentioned observation, that GRF18(Mal$^-$):pYc1-α transformants are not able to grow on starch as a sole carbon source.

Transformation of *Schwanniomyces alluvius*

One of the prerequisites for the establishment of a transformation system is the availability of an appropriate mutant which can be functionally complemented by a cloned gene.

Various tryptophan auxotrophic *Schwanniomyces alluvius* mutants were analysed for their defect in the L-tryptophan biosynthetic pathway. The mutants were tested for having a defect in the last step of L-tryptophan biosynthesis, namely the condensation reaction of indole and L-serin, which in *Saccharomyces cerevisiae* is catalysed by tryptophan synthetase.

A defect in this last step leads to an accumulation of indole (Manney et al., 1969). The tryptophan auxotrophic mutant NGA23 accumulates indole when grown in YNB medium. In addition, compared to other tryptophan auxotrophs, NGA23 cannot grow on YNB containing indole. It was therefore concluded that NGA23 has a mutation in the tryptophan synthetase gene. NGA23 exhibits a low reversion rate ($10^{-8}$) and is thus suitable for complementation studies with the cloned *Saccharomyces cerevisiae* TRP5 gene (Carbon et al., 1977) coding for tryptophan synthetase (Walz et al., 1978; Zalkin et al., 1982). The initial intention was to transform NGA23 via integration.

The transformation experiment was based on the assumption that there is no extensive homology between the TRP5 gene of *Saccharomyces cerevisiae* and the mutated tryptophan synthetase gene of *Schwanniomyces alluvius* as revealed by Southern hybridisation of nick translated pYaS1 (Strasser, 1982) DNA to chromosomal DNA of *Schwanniomyces alluvius*.

Figure 8:
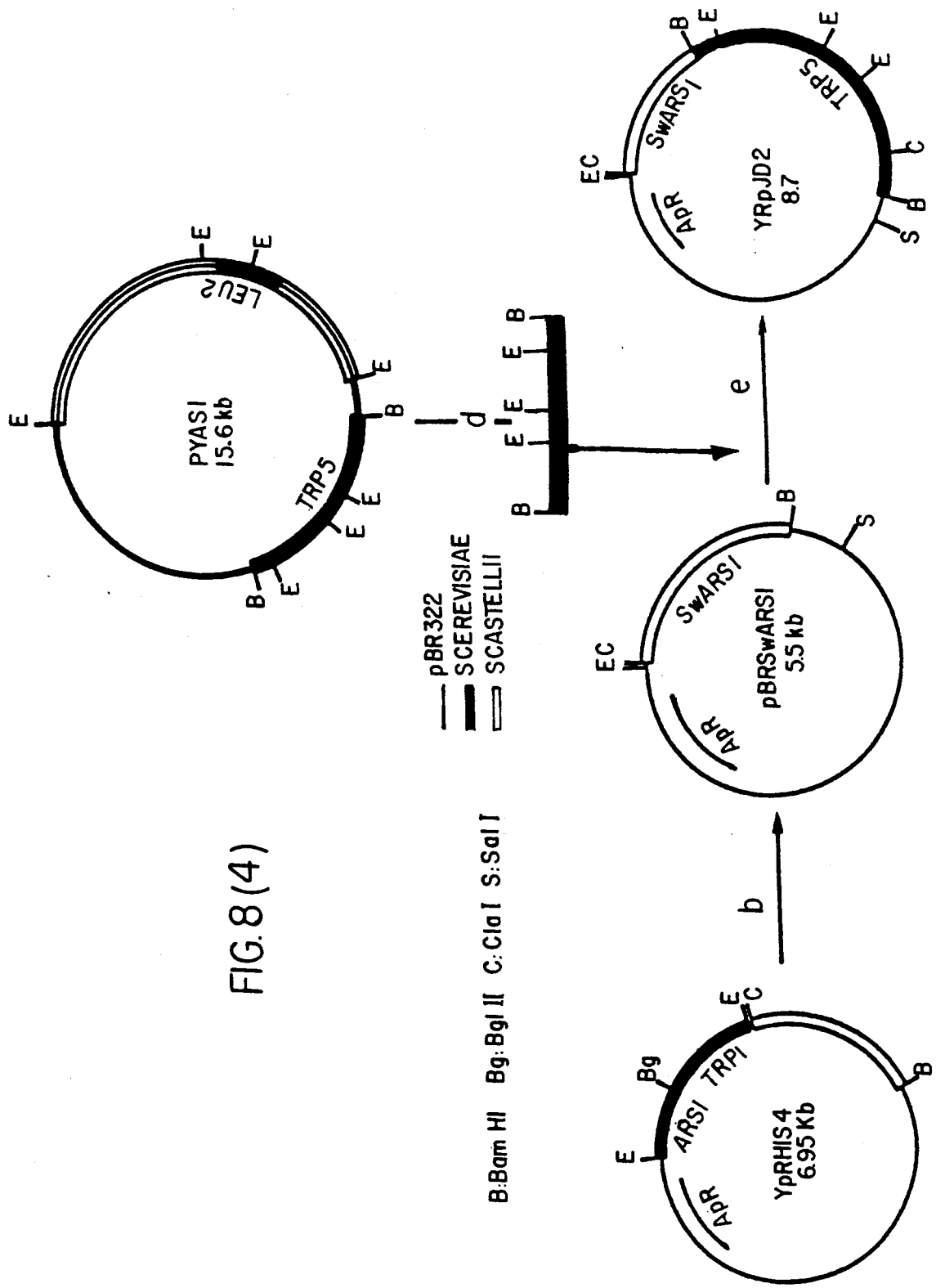
Figure 8:
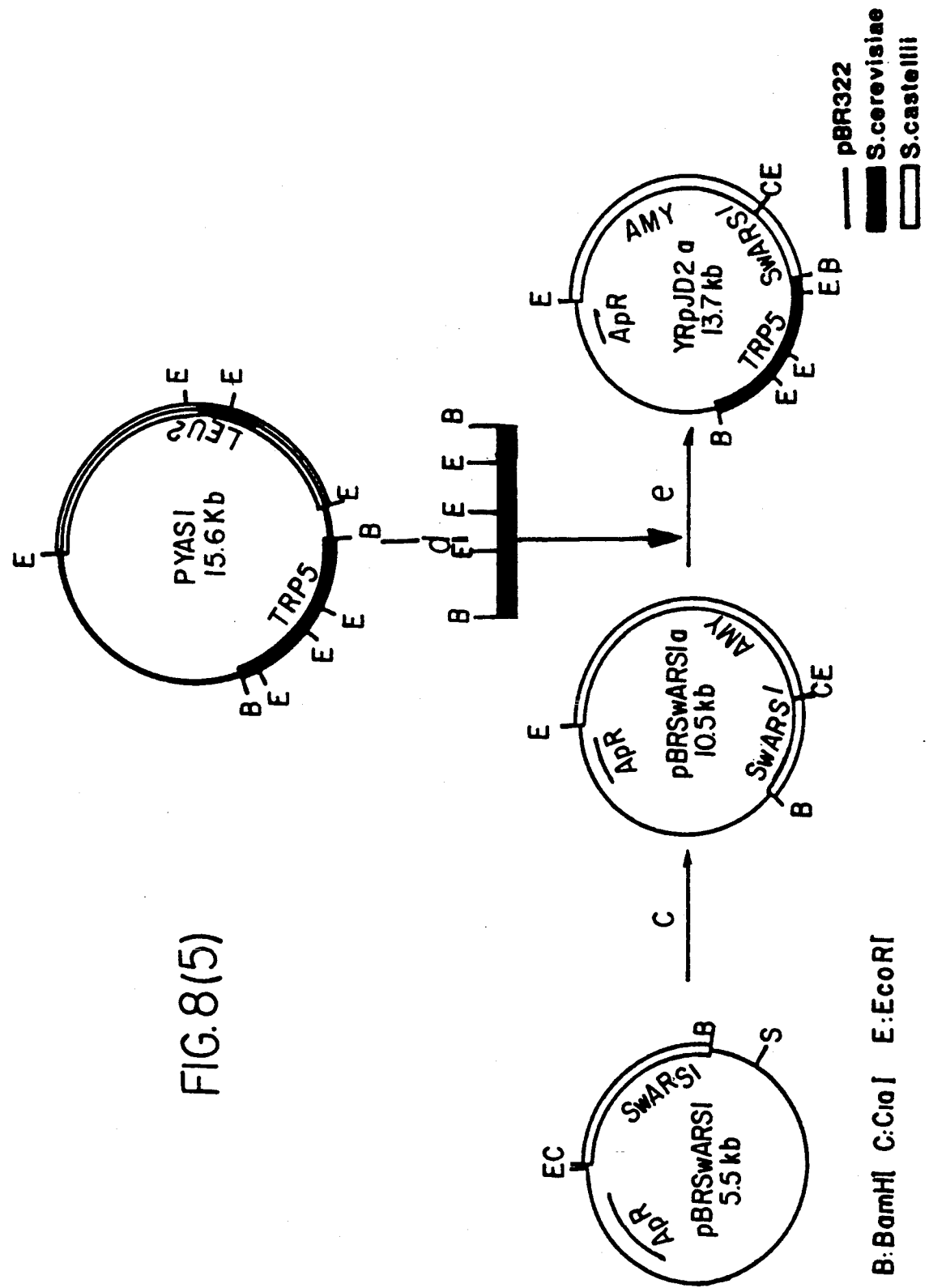

From a partial Sau3A bank of Schwanniomyces DNA in YRP7, a 9 kb DNA fragment was cloned, resulting in plasmid YRP7HIS4 complementing the his4 mutation of *Saccharomyces cerevisiae* strain AH22 (FIG. 8).

It was assumed that a 1.5 kb BamHI-ClaI fragment from this HIS4 region of *Schwanniomyces castellii* should have enough homology to direct integration into the genome of *Schwanniomyces alluvius* NGA23 via homologous recombination. Therefore, the plasmid YRpJD2 was constructed (FIG. 8), containing the *Saccharomyces cerevisiae* Trp5 gene as a selectable marker and the 1.5 kb BamHI-ClaI fragment.

YRpJD2 was used to transform NGA23 by the protoplast method described by Beggs (1978) screening for tryptophan prototrophy on YNB plates. Five transformants per μg plasmid DNA were obtained.

It seemed unlikely that this surprisingly high transformation frequency was due to integration events, taking into acount that the plasmid was not linearised prior to transformation, which would have increased the probability for integration (Orr-Weaver et al., 1981) and that the regeneration frequency of Schwanniomyces using the protoplast method was lower than 0.1%.

The transformation of NGA23 with YRpJD2 is based on autonomous replication as was indicated by the instability of the Trp$^+$ phenotype after growth of the transformants under non-selective conditions in YEPD.

After 15 generations, 80-90% of the cells had lost the ability to grow on selective medium.

The autonomous replication was ascertained by transforming *E. coli* cells with yeast minilysates and retransformation of Schwanniomyces NGA23. In addition, Southern analysis showed the presence of original YRpJD2 sequences (FIG. 9) and thus exclude integration of the TRP5 gene as a cause of the tryptophan prototrophy.

No transformants except for some abortive transformants could be obtained after transformation of NGA23 with pYe(trp5)1-53 (Walz et al, 1978), which does not contain the 1.5 kb fragment of *Schwanniomyces castellii* indicating that this Schwanniomyces DNA fragment contains a sequence which allows autonomous replication of plasmid YRpJD2 in *Schwanniomyces alluvius* NGA23.

Therefore, it is concluded that the 1.5 kb DNA fragment of *Schwanniomyces castellii* in the vector YRpJD2 contains an autonomous replication sequence, namely SwARS1.

Transformation Procedure

The regeneration of Schwanniomyces cells using the protoplast method (Beggs, 1978) for transformation is approximately 0.1%. Because the regeneration rate or protoplast formation correlates directly with the transformation frequency, attempts were made to change the conditions for protoplast formation using different concentrations of helicase or zymolyase and different incubation times for the transformation of YRpJD2 into NGA23.

Using helicase, no transformants could be obtained. Only by using zymolyase (1 mg/ml) for 30 min at 37° C. with a regeneration rate of 0.1%, 5 transformants per μg YRpJD2 plasmid DNA could be obtained. Shorter incubation resulted in an increase of the regeneration frequency to approximately 0.5%, but no transformants were obtained.

These findings demonstrate that the protoplast formation (and not the regeneration frequency and hence the enzymatic degradation of the cell wall) is the critical step in the transformation of Schwanniomyces using the protoplast method. Therefore, the transformation procedures described by Ito et al. (1983) and Klebe et al. (1983) were tested.

Both procedures do not require the enzymatic degradation of the cell wall. With the lithium sulphate method of Ito et al. (1983), no transformants were obtained. However, using the freeze-thaw method of Klebe et al. (1983) NGA23 could successfully be transformed with YRpJD2 plasmid, yielding reproducibly 50-100 transformants per μg YRpJD2 plasmid DNA.

Using the method of Klebe et al (1983), log phase yeast (10 ml) was washed with 5 ml of SBEG (1M sorbitol, 10 mM bicine, pH 8.35, 3% ethylene glycol) by centrifugation at 1000×g for 3 min at 22° C. All subsequent incubations were carried out at 30° C. The pellet was resuspended in 0.2 ml SBEG; and after 5 min, 1 to 20 μl plasmid DNA was added. After 10 min, the preparation was placed in a −70° C. freezer for 10 min (or longer) and thawed by rapid agitation in a 37° C. water bath. 1.5 ml of 40% purified PEG 1000 (Klebe et al., 1983), 200 mM bicine pH 8.35 (stored frozen) was added; and after a 1 h incubation, the cells were washed with 2 ml 0.15 mM NaCl, 10 mM bicine pH 8.35. After centrifugation, the pellet was resuspended in 1 ml 0.15 mM NaCl, 10 mM bicine pH 8.35, and plated on selective medium. Using the conditions described above, the plasmid DNA is added before the cells are frozen at −70° C. However, the possibility of adding the DNA to the frozen cells just before thawing would be of advantage to have competent cells at any time for the transformation with any plasmid available.

The attempts of adding YRpJD2 DNA to frozen cells of the *Schwanniomyces alluvius* mutant NGA23 were successful in that the same transformation frequencies (50-100 transformants per μg) as compared to the orginal procedure described above were obtained.

Klebe et al. (1983) describes that the PEG used is critical for reproducible transformation. Therefore Klebe et al. (1983) performed a time consuming PEG 1000 preparation for optimal transformation efficiency.

To circumvent this tedious procedure, the influence of several PEGs from Serva and Roth company was tested. Until now, the optimal transformation efficiencies were obtained using PEG 1000 from Roth company. Substitution of 1M sorbitol in SBEG by 1.25M KCl, 30 mM $CaCl_2$ leads to an increase in the transformation frequency by a factor 2, yielding 200 NGA23 transformants per μg YRpJD2 plasmid DNA.

During freezing of yeast cells, the plasma membrane becomes damaged, resulting in a higher permeability; in addition, the degree of cell damage is dependent on the velocity of freezing (Lepock et al., 1984). Based on these observations, the transformation competence of the cells was tested after freezing at −70° C. in a freezer (relatively slow freezing), with dry ice acetone at −78° C. (fast freezing) and with liquid nitrogen −196° C. (very fast freezing).

Using liquid nitrogen, the transformation frequency decreased by 40%, whereas the usage of dry ice acetone increased the yield of transformants by 30% compared to freezing in a −70° C. freezer.

The DNA was added to the frozen cells (stored at −70° C. for 10 min up to 6 months) and thawed by rapid agitation at 37° C. Instead of rapid agitation in a 37° C. water bath, an Eppendorf mixer, type 5432, at 37° C. was used. This condition for rapid agitation during thawing gave the best reproducible transformation frequencies.

With these modifications, a transformation frequency of 300-1000 transformants per μg YRpJD2 plasmid DNA was obtained for *Schwanniomyces alluvius* NGA23 mutants.

With this simplified transformation procedure, high transformation frequencies could also be obtained for *Saccharomyces cerevisiae, Schizosaccharomyces pombe,* and *Kluyveromyces lactis* (Table II).

Estimation of Plasmid Copy Number in *Schwanniomyces alluvius* and *Saccharomyces cerevisiae* Transformants With our simplified transformation procedure, *Schwanniomyces alluvius* NGA23 was transformed with:

| | |
|---|---|
| pYe(trp5)1-53 | containing pBR313 (Bolivar et al., 1977) and the TRP5 gene of *Saccharomyces cerevisiae* |
| pYAS1 | a 2 μM derivative containing both the LEU2 and TRP5 genes of *Saccharomyces cerevisiae* (Strasser, 1982) |
| YRP7TRP5 | containing ARS1 and both the TRP1 and TRP5 genes of *Saccharomyces cerviasiae* |
| YRpJD1 | containing both SwARS1 and ARS1 and both the TRP1 and TRP5 genes of *Saccharomyces cerevisiae* |
| YRpJD2 | containing SwARS1 and the TRP5 gene of |

| | |
|---|---|
| pEK2TRP5 | Saccharomyces cerevisiae containing both KARS1 and ARS1 and the TRP5 gene of Saccharomyces cerevisiae |

The plasmids are summarised in FIG. 8.

The transformation frequencies and stabilities of these plasmids in Schwanniomyces alluvius NGA23 are summarised in Table III. The copy numbers of the different plasmids were estimated by Southern blot analysis (FIGS. 9 and 10).

The chromosomal HIS4 locus representing one copy per cell was used as an internal standard. There are three chromosomal EcoRI fragments (0.9 kb, 6.0 kb, 8.0 kb) which hybridize with $^{32}$p-labelled YRP7HIS4 DNA. The homology of the chromosomal HIS4 locus and of the YRpJD1 plasmid to the hybridisation probe YRP7HIS4 is represented in FIG. 10D.

For copy number estimation of the plasmids pYAS1, YRP7Trp5, YRpJD1, (YRpJD2) and pEK2TRP5, the intensity of the common 5.3 kb EcoRI band was compared with the 6 kb EcoRI band of the chromosomal HIS4 gene.

The intensity of staining in the autoradiogram reveals that the plasmids YRpJD1 and YRpJD2 have a copy number of about 5-10 copies per cell (FIGS. 9 and 10).

Both the plasmids YRP7TRP5 and pEK2TRP5 have about the same average copy number per cell, which is in the range of about 0.2-1, independent of the orientation of the TRP5 fragment, whereas pYAS1 exists in about 2-3 copies per cell (FIG. 10).

Figure 11:
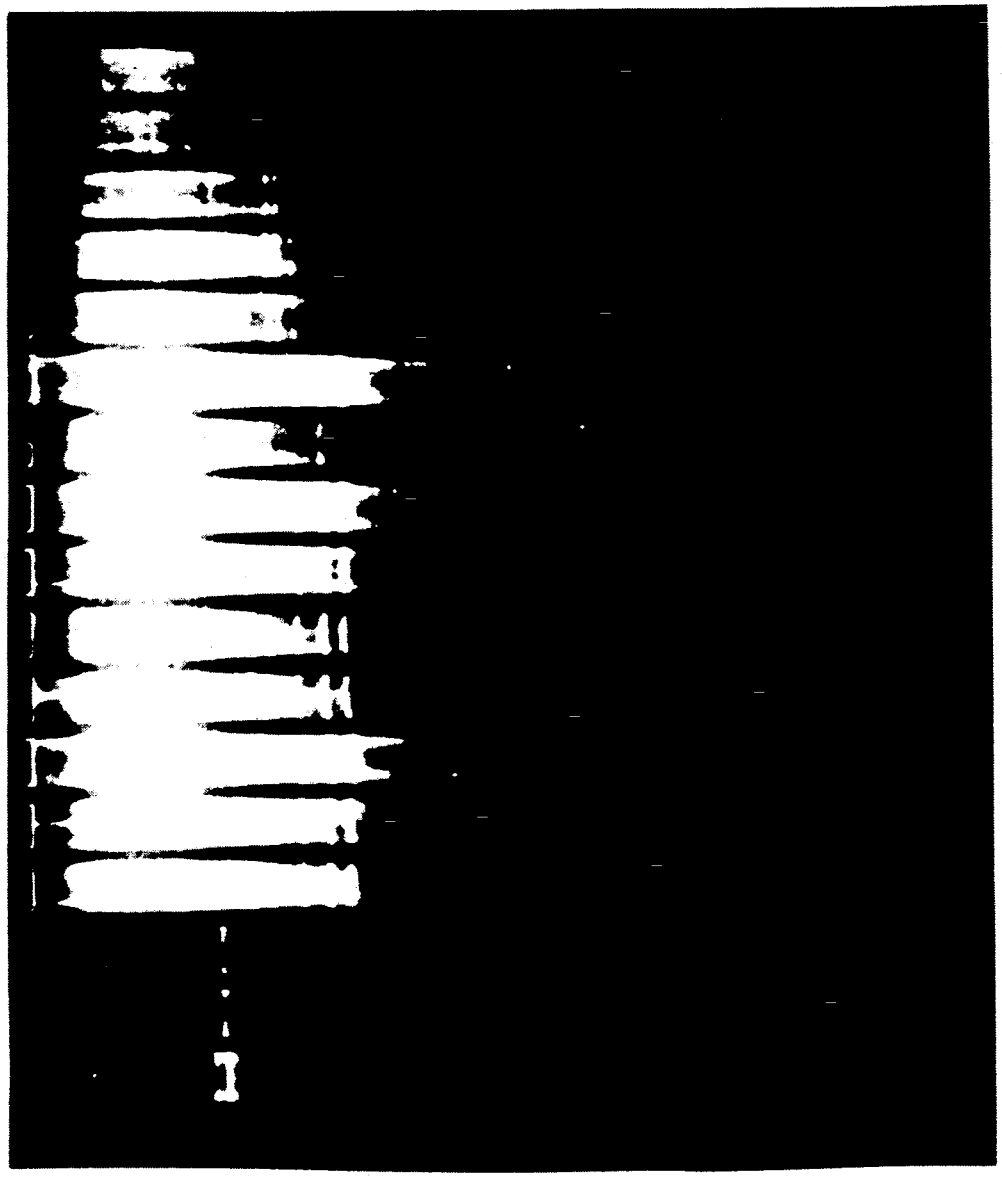
Figure 11:
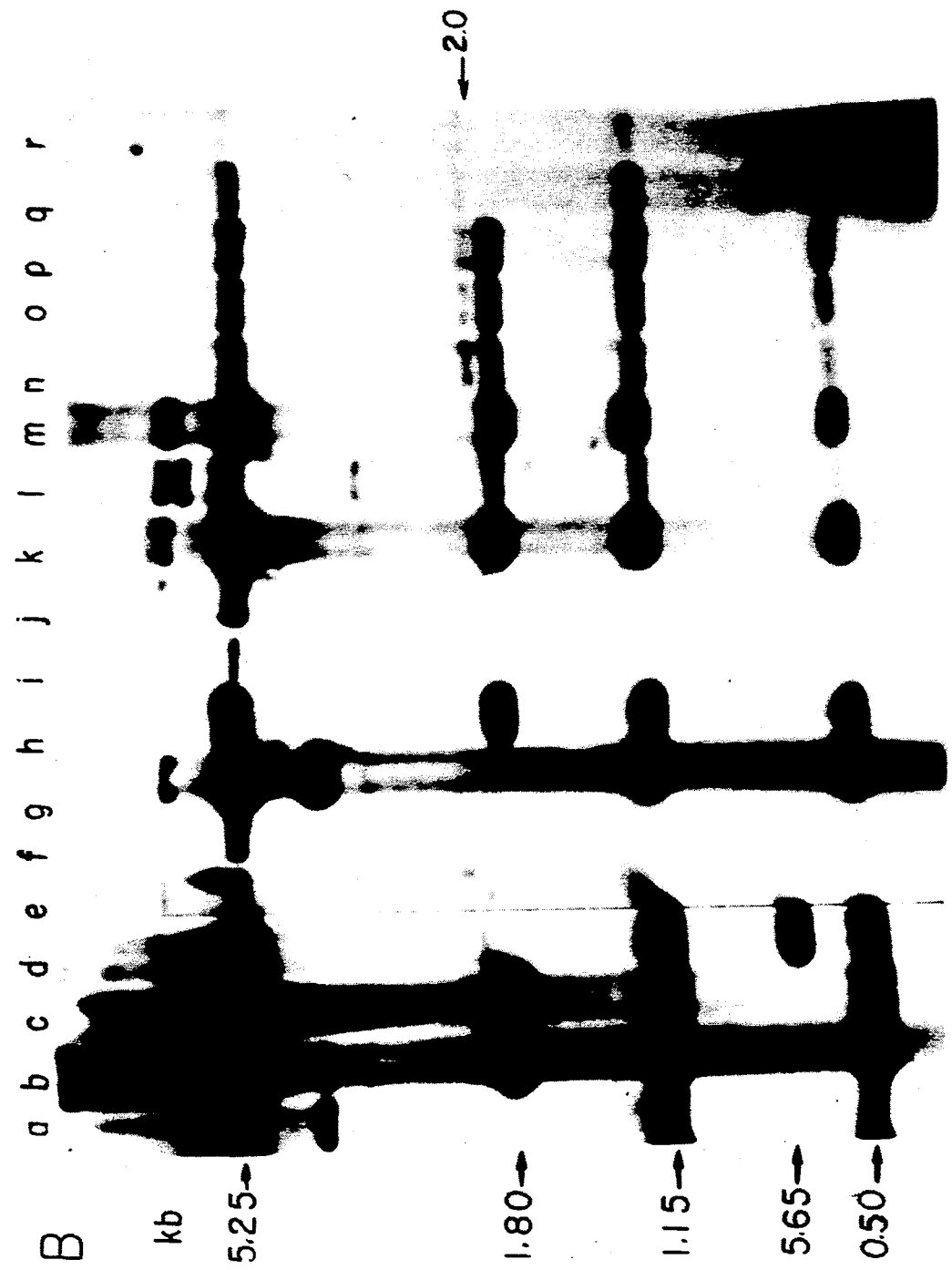

ARS1 and 2 μm DNA sequences of Saccharomyces cerevisiae can be used for autonomous replication in Schwanniomyces alluvius NGA23 although not as efficiently as SwARS1. SwARS1 behaves in Schwanniomyces alluvius as ARS1 in Saccharomyces cervisiae, yielding 5-10 copies per cell (FIG. 11, Table IV). The plasmid YRpJD1 which has the ARS1 element in addition to SwARS1 element, showed no increased copy number as compared to YRpJD2, which only has the SwARS1 element. The plasmid pEK2TRP5, which has the KARS2 element in addition to the ARS1 element, has the same copy number as the plasmid YRp7TRP5, which only has the ARS1 element. It is therefore assumed that KARS2 cannot serve as an efficient autonomous replication element in Schwanniomyces alluvius.

The transformation of Schwanniomyces alluvius NGA23 with pYe(trp5)1-53 (Walz et al., 1978) can be explained by an abortive transformation event concerning the high instability of these transformants (Table III).

Regulation of the Cloned Schwanniomyces castillii α-amylase Gene and Over-Production of the Portein in Schwanniomyces alluvius Transformants The production of α-amylase in the yeast species Schwanniomyces underlies catabolite repression in the presence of glucose (Sills et al., 1982).

The synthesis of α-amylase is induced by soluble starch dextrins and maltose (Sills et al., 1982). Maltose, which is part of the products after starch degradation, was found to be a stronger inducer than soluble starch (Sills et al., 1984b). It appears that a very low basal level of amylase is constitutively produced. This low level of α-amylase can hydrolyse starch, releasing low molecular weight sugar such as maltose, which can penetrate the cell membrane and in turn induce the synthesis of α-amylase (Sills et al., 1984b).

To study regulation and expression of the cloned α-amylase gene in Schwanniomyces alluvius, the 5 kb EcoR1 fragment containing the structural α-amylase gene was inserted into the YRpJD2 (FIG. 8), resulting in plasmid YRpJD2-α and transformed into Schwanniomyces alluvius NGA23 with selection for tryptophan prototrophy on YNB plates.

As it is shown in FIG. 5B, the total α-amylase activity of NGA23: YRpJD2-α transformants growing under induced condition in YNB maltose medium is increased 4-5 fold compared to control transformants NGA23: YRpJD2 which do not contain additional plasmid encoded α-amylase (FIG. 4A).

During the induction phase of α-amylase synthesis, the drastical 7-fold increase in extracellular α-amylase activity per cell concentration ($OD_{600}$nm) compared to control transformants, correlates with the estimated 5-10 copies of SwARS1 plasmids in Schwanniomyces alluvius.

It is therefore concluded that the increase in α-amylase activity is due to a gene dosage effect.

When the NGA23: YRpJD1 and NGA23: YRpJD2 transformants were grown under repressed conditions in YNB containing 2% glucose, no α-amylase activity could be measured in the extracellular medium until the glucose concentration dropped to about 0.2 mM (FIG. 4C and E). Thus the plasmid encoded α-amylase is regulated by catabolite repression as chromosomal α-amylase.

By construction of the α-amylase structural gene under control of a high expression promoter as e.g. that of PDC1 or PGK genes, higher expression strains independent of growth stage and C-source can be obtained.

Figure 12:
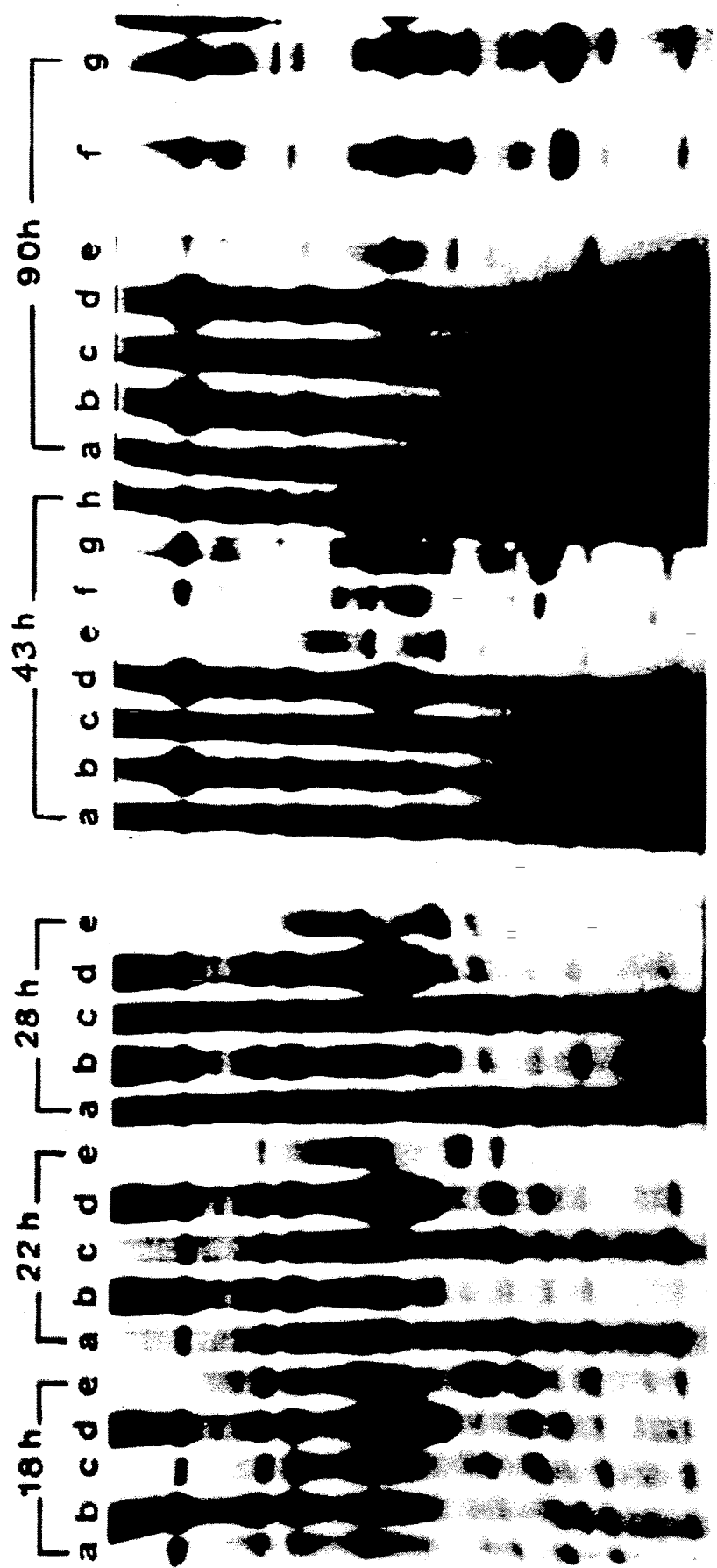

The overproduction of the α-amylase protein was shown by analysis of in vitro labelled proteins of the culture supernatant by fluorography (FIG. 12). α-amylase activity could be measured in the extracellular medium of MC34: pYC1α transformants under growth in YNB containing 2% and also 4% glucose as a sole carbon source indicating that the plasmid encoded α-amylase is not regulated by catabolite repression in Saccharomyces cerevisiae.

Isolation of Auxotrophic Mutants of Schwanniomyces alluvius

For prosecuting the cloning of the glucoamylase gene, the functional complementation of a glucoamylase mutant of Schwanniomyces alluvius was chosen.

A prerequisite is the availability of an appropriate mutant which can be complemented by the cloned gene. For this purpose, a Schwanniomyces alluvius mutant NGS1 which is not able to grow on maltose or soluble starch as a sole carbon source was analysed. When this mutant was grown on plates containing 1% glucose and 1% soluble starch, halo formation could be observed after iodine staining, indicating that α-amylase can be secreted by the mutant. No glucoamylase activity could be detected in crude extracts and culture supernatant.

As already mentioned, α-amylase can hydrolyse starch into dextrin, maltose and higher oligosaccharides (FIG. 7), whereas glucoamylase can use these products as substrates for the enzymatic hydrolysation into glucose. The interesting feature of the NGS1 mutant is the inability to grow on maltose. The Schwanniomyces alluvius wild type secretes glucoamylase which hydrolyses maltose to glucose in the extracellular medium, and hence, in contra to *Saccharomyces cerevisiae*, has no need for a maltose uptake system. It is therefore concluded that NGS1 is an α-amylase+ glucoamylase− mutant, in having no functional glucoamylase either by a point mutation in the structural gene, or in the promoter region.

We have focused our attention on this glucoamylase mutant to clone the glucoamylase gene of *Schwanniomyces castellii* by functional complementation.

For cloning purposes, an additional mutation had to be introduced into the α-amylase+ glucoamylase− mutant, preferentially a trp5 mutation (leading to a defect in the indole tryptophan reaction), because *Schwanniomyces alluvius* could be efficiently transformed using the TRP5 gene of *Saccharomyces cerevisiae* as a selectable marker on SwARS1 containing plasmids e.g. YRpJD1 and YRpJD2. In addition, these mutants can easily be identified by their property of indole accumulation.

For the isolation of trp5 auxotrophic mutants, all procedures were carried out at 30° C. 10 ml NGS1 culture was grown to $OD_{600}=0.6$ in complex medium, washed twice with $H_2O$ and exposed to UV light (254 nm) for 50 seconds (1% survivals). The mutagenized cells were then incubated for 2 days on complex medium for segregation of the trp auxotrophs and plated on YEPD plates for replica plating on minimal medium containing tryptophan and on minimal medium plates containing all amino acids but no tryptophan.

From 2614 NGS1 colonies tested, 7 trp auxotrophic mutants which grow on minimal medium containing tryptophan but not on minimal medium containing all amino acids except tryptophan, could be isolated (reversion rate $10^{-7}$–$10^{-8}$). Two of these seven mutants could be analysed to be defective in the indole tryptophan reaction since both were accumulating indole.

These trp5, α-amylase+glucose− mutants were designated NJD1 and NJD2. These two strains could be efficiently transformed with YRpJD1 yielding approximately 800 transformants per µg DNA, indicating that NJD1 and NJD2 are really mutated in the TRP5 gene.

Further cloning procedures can be carried out in an analogous manner as with the α-amylase gene.

Construction of an *E. coli-Saccharomyces cerevisiae-Schwanniomyces alluvius* Cosmid Shuttle Vector for Cloning Genes in *Schwanniomyces alluvius*

In analogy the the cosmid pYc1 (2µ) and pYc2 (ARS) which were constructed for cloning genes in *Saccharomyces cerevisiae* (Hohn and Hinnen, 1980), a cosmid for cloning in *Schwanniomyces alluvius* was constructed.

Cosmids are plasmids which contain the cos (cohesive sequence) region of bacteriophage lambda (Collins and Hohn, 1978) as well as the essential sequences for cloning (replication origins, a gene as selectable marker and suitable cloning sites). The cos sequence comprises the structural information necesary for packaging the DNA to produce an intact bacteriophage lambda (Hohn, 1975). High molecular oligomeric cosmid DNA can therefore be efficiently packaged by an in vitro packaging system (Hohn, 1979), if the cos sequences are separated by any 37–52 kb DNA fragments corresponding to about 73% to 105% of the lambda phage genome (Feiss et al., 1977). The relatively large size of clonable fragments presents the possibility that only about 1,200 cosmid clones containing fragments with an average size of about 30–40 kb are necessary to encompass the genome of *Saccharomyces cerevisiae* by more than 85% (Hohn and Hinnen, 1980).

For cloning large DNA fragments, the advantage in using cosmid instead of plasmid DNA is that relatively high molecular oligomeric DNA can easily be obtained by ligation of highly concentrated DNA, whereas the efficiency to form circular transformable plasmids by ligation of large DNA fragments with smaller vector DNA is disadvantageous because of the relation between the fragment size and effective concentration of free ends (Dugaiczyk et al., 1975). In addition, the packaged DNA can efficiently be transduced by infection of lambda sensitive *E. coli* cells (Hohn and Hinnen, 1980).

Based on these observations, an *E. coli-Schwanniomyces alluvius-Saccharomyces cerevisiae* cosmid shuttle vector was constructed by subcloning the 1.7 kb BglII fragment of plasmid pHC79 containing the cos region (Hohn and Collins, 1981) into one of the two BamHI sites of YRpJD2. YRpJD2 was therefore partially digested with BamHI (0.5 units/µg DNA at 30° C.) and the resulting largest linear DNA which arises from a single cleavage by BamHI was isolated by preparative gel electrophoresis and ligated with the 1.7 kb BglII fragment of pHC79, which has also been isolated by preparative gel electrophoresis after complete digestion of pHC79 DNA. This ligation mixture was used to transform *E. coli* JA221, selecting on ampicillin resistance. Subclones were screened by colony hybridisation using the nick translated 1.7 kb BglI fragment as a radioactive probe.

From the positive clones, two different cosmids, namely pCJD5-1 and pCJD5-2 (FIG. 13a) could be isolated and analysed after cleavage with EcoRI, BamHI and PvuII restriction enzymes (FIG. 13b). FIG. 13b demonstrates that in cosmid pCJD5-1, the cos sequence is subcloned into the BamHI site of YRpJD2 between the SwARS1 sequence and the TRP5 gene. In pCJD5-2, the cos region was inserted in tandem at the same position. The existence of two, in tandem, orientated cos elements should drastically increase the packaging efficiency compared to cosmids which contain only a single cos element (Lindenmeier et al., 1982). Up till now, it was not tested whether this is also the case for pCJD5-2.

With cosmids pCJD5-1 and pCJD5-2, 500–1000 NJD1 transformants per µg cosmids DNA were obtained by selecting on tryptophan, indicating that the cos element does not influence the transformation frequency. Both cosmids contain (a) the SwARS1 sequence which acts as replication origin in *Schwanniomyces alluvius* as well as *Saccharomyces cerevisiae*

(b) the origin for replication of *E. coli;*

(c) the ampicillin resistance gene as selectable marker in *E. coli;*

(d) the TRP5 gene of *Saccharomyces cerevisiae* as selectable marker in *Schwanniomyces alluvius* as well as in *Saccharomyces cerevisiae* trp5 mutants; and (e) the cos region as prerequisite for the construction of a cosmid library.

In addition, both cosmids contain suitable cloning sites, namely BamHI and SalI for cloning Sau3A, BamHI, BglII, SalI and XHOI fragments, and hence provide a new class of cosmid vectors for the construction of a genomic DNA library to clone genes in *E. coli, Saccharomyces cerevisiae* and *Schwanniomyces alluvius*.

Cloning of the Glucoamylase Gene from Schwanniomyces castellii

The cloning of the glucoamylase gene was started from a Schwanniomyces castellii ATCC 26076 cosmid pool which was established by ligating partially BamHI digested genomic DNA of Schwanniomyces castellii into the E. coli-Saccharomyces cerevisiae-Schwanniomyces alluvius shuttle vector pCJD5-1 using the cosmid cloning technique described by Ish-Horowicz et al., 1981.

After in vitro packaging of the DNA ligation mixture, E. coli strain HB101 was infected, yielding approximately 15,000 ampicillin resistant colonies corresponding to approximately 30 genome size equivalents of Schwanniomyces castellii assuming the same genome size for Schwanniomyces castellii as for Saccharomyces cerevisiae (approx. 15,000 kb) and a cloned DNA fragment ranging between 30 and 40 kb in size. From these transductants, cosmid DNA was isolated and used for the transformation of NJD1 ($\alpha$-amylase$^+$ glucoamylase$^-$trp5) with selection for trp prototrophy on minimal medium containing 2% glucose.

The transformation frequencies using both the protoplast method (Beggs, 1978) and the simplified freeze thaw method was relatively low (1–10 transformants/$\mu$g cosmid DNA). Nevertheless approx. 3,000 transformants could be obtained which were screened for their regained ability to grow on soluble starch as sole carbon source. One NJD1 transformant which has a Trp$^+$ and glucoamylase$^+$ phenotype could be isolated from starch plates. In a mitotic stability test (Beggs, 1978), both the TRP5 phenotype and the glucoamylase complementing functions were segregated out, simultaneously indicating that both genes were carried by the cosmid. The cosmid was rescued by transforming E. coli HB101 with yeast minilysate and selection for ampicillin resistance. Cosmid DNA was isolated and used for retransformation of NJD1, to ascertain that the glucoamylase complementing function is still carried by the isolated cosmid DNA. After cleavage of the cosmid with BamH1, two BamH1 sites could be localised within the cloned fragment, dividing it into the three fragments, two of them being of approx. 10 kb and 12 kb.

In order to decrease the size of the approx. 40 kb size cosmid, BamHI fragments were subcloned into the single BamHI site of pCJD5-1 plasmid. Therefore, the cosmid DNA was digested with BamHI, religated and transformed into E. coli HB101. The plasmid DNA from ampicillin resistant cells was used to transform NJD1 and to screen for growth on soluble starch as a sole carbon source. Plasmid DNA was rescued by transforming HB101 with yeast minilysate and selection for ampicillin resistance. Plasmid DNA was isolated for restriction analysis after digestion with BamHI endonuclease.

Figure 14:
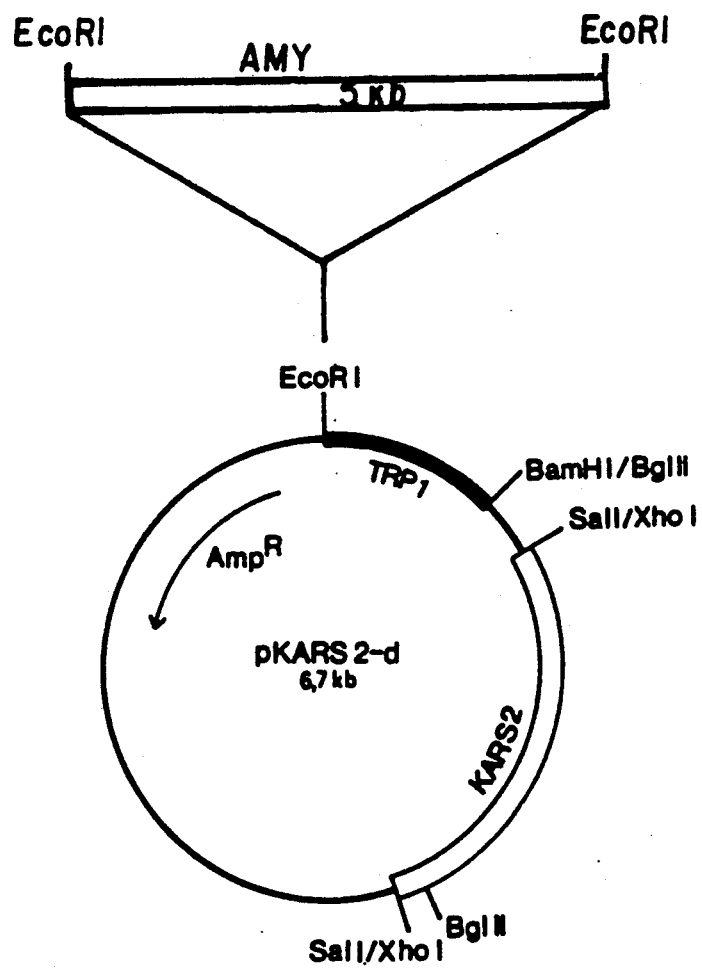

FIG. 15 demonstrates that the glucoamylase complementing function is carried by the 12 kb BamHI fragment, subcloned into pCJD5-1. This plasmid is designated pCJD5-AMG1 (FIG. 14). Since this plasmid contains the SwARS1 element acting in Saccharomyces cerevisiae as well as in Schwanniomyces alluvius, the cloned gene in Saccharomyces cerevisiae was analysed by transforming X3656 selecting on tryptophan prototrophy. Unfortunately the transformants were not able to use soluble starch as a sole carbon source. The first explanation, that the 5–10 copies of pCJD5-AMG1 in Saccharomyces cerevisiae are not high enough to overcome possible proteolytic degradation, failed, since after subcloning of the approx. 12 kb BamHI fragment into the high copy number, plasmid pJDB207 (Beggs, 1981) (FIG. 14) having 50–100 copies per cell, and transformation of GRF18 Saccharomyces cerevisiae cells, none of the transformants were able to grow on soluble starch as a sole carbon source.

Although glucoamylase activity could be measured in NJD1: pCJD5-AMG2 transformants, no activity in both crude extract and culture filtrate of Saccharomyces cerevisiae transformants could be detected. Because Käufer et al. (1985) have recently shown that Schizosaccharomyces pombe has a considerable advantage over Saccharomyces cerevisiae in accurately excising an intervening sequence from a transcript of a higher eucaryotic gene, attempts were made to express the glucoamylase in this fission yeast. However, no expression and secretion of glucoamylase could be detected in Schizosaccharomyces pombe leu1-32 (complemented with LEU2 of Saccharomyces cerevisiae after transformation with plasmid pJDB20$^7$-AMG$^1$ (FIG. 14). The transformation of the gene into Kluyveromyces lactis SD11(trp1) with pEK2-AMG2 (FIG. 14) did not lead to transformants which can grow on soluble starch as sole carbon source. It is therefore concluded that a Schwanniomyces gene was cloned which cannot be functionally expressed in Saccharomyces cerevisiae, Schizosaccharomyces pombe, and Kluyveromyces lactis because of different splicing specifities, promoter recognition or Schwanniomyces specific post transcriptional processing.

For further analysis, subcloning smaller fragments of the 12 kb DNA was carried out in order to find the smallest possible DNA fragment still carrying the functional complementation property. The molecular weight of glucoamylase is approx. 117,000 d (Simoes-Mendes, 1984) corresponding to a long structural gene of about 3 kb in length.

Furthermore, the gene can be sequenced to analyse codon usage and possibly existing introns. Additionally, the 5' non-coding leader sequence of Schwanniomyces castellii DNA can be exchanged by a well characterised promoter such as the ADH1 (Hitzeman et al., 1981) or PDC promoter (Hollenberg et al., 1983) to exclude possible inefficiency of the Schwanniomyces promoter in other yeast species.

In order to characterize the gene, glucoamylase was isolated for the production of glucoamylase specific antibodies to assay the crude extracts and culture filtrate of NJD1 as well as Saccharomyces cerevisiae or Schizosaccharomyces pombe and Kluyveromyces lactis transformants for the presence of inactive glucoamylase. No promoter activity could be detected in Saccharomyces cerevisiae transformants by Northern analysis. In addition there was no protein detectable in culture supernatants and crude extracts of the Saccharomyces cerevisiae transformants'using a specific antibody raised against glucoamylase. In addition, peptides of purified glucoamylase were isolated for amino acid sequencing in order to synthesize synthetic oligonucleotides for analysing the cloned gene.

To exclude cloning artefacts arising from the construction of the Schwanniomyces cosmid library a Charon 4A Schwanniomyces castellii library, as described by Maniatis et al. 1982, containing partial EcoRI fragments (10–30 kb) of Schwanniomyces castellii DNA yielding approximate 150000 inserts was screened directly for the glucoamylase gene.

The Charon library was further analysed by two different oligonucleotide mixtures which were deduced from a part of peptide 3 (amino acid 11-18) and from peptide 4 respectively (see FIG. 3). The smallest restriction fragment hybridizing with both 5' labelled oligonucleotide mixtures was a 3.7 kb BglII DNA fragment. S1 mapping revealed that a complete transcript mapps within that fragment. This fragment was sequenced by Maxam and Gilbert (1980). The DNA sequence is presented in FIG. 17.

All five peptide sequences, (FIG. 3) were found within the open reading frame of 2874 bases.

The expression of the glucoamylase gene can be achieved by promoter exchange. A *Saccharomyces cerevisiae* promoter region initiation of transcription and regulation when inserted 5' upstream to the coding sequence of the glucoamylase gene. There are no suitable restriction sites in front of the translation start point of the glucoamylase gene which could be used for promoter fusions. Therefore, we introduced a BamHI and SalI restriction site 5' to the translation initiation codon by site-directed mutagenesis by the gapped duplex DNA method (Kramer et al (1984)).

A synthetic oligonucleotide of 42 bases (5' CTCATGACTGTGTCGA CGGATCCAAGATGATTTTTCTGAAGC 3') was annealed to the gapped duplex DNA. Filling up the single stranded areas with DNA polymerase (large fragment), ligation and *E. coli* transformation were performed and a recombinant mutagenized plasmid could be isolated containing a BamHI site at position −9 and a SalI site at position −15 with respect to the first base of the translation initiation codon.

From the resultant recombinant plasmid the structural gene can be sub-cloned as a BamHI/SalI, BamHI/HindIII, SalI/SalI, BamHI/PstI, SalI/PstI, BamHI/XbaI and SalI/XbaI in appropriate expression vectors fusing the gene with one of the mentioned restriction sites to different promoters. Every other suitable restriction site can be introduced by a suitable linker.

Different expression vectors using different promoters, different selectable markers and different replication origins (2μ, ARS and CEN) for yeast were constructed.

For example, the gene was fused to the inducible galactokinase (GAL1) promoter in plasmid pBM272, which is directly derived from vector pBM150 (Johnston and Davis 1984) by introducing a Hind III site immediately behind the BamHI site. The DNA sequence of the fusion is as follows:

The glucoamylase secreted by the *Saccharomyces cerevisiae* transformant has maximum activity at 50° C. and can be inactivated at 60° C. as is the case for *Schwanniomyces alluvius* glucoamylase.

The expression of the glucoamylase and secretion of the glucoamylase protein could also be achieved under control of the pyruvate decarboxylase (PDC) promoter (Hollenberg et al., 1983), phosphoglycerate kinase (PGK) promoter (Dobson et al., 1982), glyceraldehyde-3-phosphate dehydrogenase (GAPDH) promoter of the gene on pgap491 (Holland and Holland, 1979), alcoholdehydrogenase 1 (ADH1) promoter (Hitzeman et al., 1981), copper-chelatin (CUP1) promoter (Karin et al., 1984, Butt et al., 1984) and alcoholdehydrogenase 2 (ADR2 or ADH2) promoter (Russell et al., 1983, Beier et al., 1985).

Over production of glucoamylase could be achieved using the PDC-promoter and high copy number plasmid (2μ with leu2d). Expression of the glucoamylase gene and secretion of the glucoamylase protein can also be detected in *Kluyveromyces lactis* after fusion of the transcriptional signals of the β-galactosidase gene (Breunig et al., 1984).

Expression of the glucoamylase gene and secretion of the glucoamylase protein can also be detected in *Schizosaccharomyces pombe* after fusion of the transcriptional signals of the alcohol dehydrogenase (ADH1) gene (Russell et al., 1983).

Expression of the glucoamylase gene and secretion of the glucoamylase protein can also be detected in *Hansenula polymorpha* after fusion of the transcriptional signals of dihydroxyacetone synthase (DHAS) (Janowicz et al., 1985) methanol oxidase (MOX) (Ledeboer et al., 1985).

In addition secretion of the α-amylase could also be detected after exchange of the Schwanniomyces promoter by the MOX promoter in *Hansenula polymorpha*.

The glucoamylase gene was integrated into the chromosome of *Saccharomyces cerevisiae* without *E. coli* sequences. Therefore, the different promoter-glucoamylase fusions were inserted into a suitable DNA sequence of *Saccharomyces cerevisiae*, preferably the homothalism gene (HO) or an ARS-sequence. A linear DNA fragment could then be generated which has ends within the *Saccharomyces cerevisiae* sequences flanking the functional glucoamylase gene. By cotransformation of *Saccharomyces cerevisiae* with YEP 36 (Butt et al., 1984) the gene could be stably integrated. The integrants exhibit glucoamylase activity in the culture supernatant and has the same fermentation and growth 5' ... upstream activation site ...

... GATATATAAATGCAAAAACTGCATAACCACTTTAACTAATACTTTCAACATTTTCG

GTTTGTATTACTTCTTATTCAAATGTAATAAAAGTATCAACAAAAAATTGTTAATATACC

TCTATACTTTAACGTCAAGGAGAAAAAACCCCGGATCCAAGATGATTTTTCTGAAGC ... 3'

The fragment containing the glucoamylase gene was sub-cloned into the vector pBM272 as a BamHI/SalI fragment. The resulting plasmid was transformed into *Saccharomyces cerevisiae* αMZ4 (αgal1, trp1, ura3, leu2). This leads to inducible expression of the glucoamylase gene and to secretion of active glucoamylase.

The amount of activity in the culture supernatant was in the range which was measured in culture supernatants of *Schwanniomyces alluvius* grown under induced conditions.

properties as the wildtype.

Genetically manipulated microorganisms, preferably yeasts, as described above in this specification are of great advantage in a lot of fermenting processes because of their ability to hydrolyze higher molecular carbohydrates.

One of the possible uses of the genetically altered yeast strains described above is in the production of biomasses. Since the yeast strains having the new ability to secrete α-amylase and glucoamylase still remained there other good fermentation abilities biomasses can be produced most efficiently by the use of the inventive yeast strains. The methods of producing the biomasses are the usual ones, known by the man skilled in the art.

A further field of use of *Saccharomyces cerevisiae*, having the new ability of producing α-amylase and glucoamylase is the production of bakers yeast and of bread, using the bakers yeast.

The inventive yeast can be used as pellet yeast, for example, made by convential drum-drying processes or can be powdered yeast, for example, having a particle size of 1.7 mm or less. Making the powdered yeast comprises spray-drying of a liquid yeast composition in air, followed by further drying, as known in the state of the art. The inventive yeast, for example, may be prepared as a dried yeast as described in GB-PS 1 459 407, GB-PS 1 459 085 or GB-PS 1 230 205. Any other methods known in the art for producing bakers yeast or producing baked products by using the new yeast of this invention are also suitable.

The genetically manipulated yeast strains provided according to this invention are further highly suitable for the production of ethanol. The preferred organism for the production of ethanol by fermentation is the yeast *Saccharomyces cerevisiae* and the preferred carbohydrate used in the ethanol production is a starch. Thus, a *Saccharomyces cerevisiae*, being able to ferment starch quantitively is highly advantageous in the production of ethanol. The production of potable spirit or industrial ethanol by the use of the genetically manipulated yeast strain of the present invention can be carried out in a manner known per se. The inventive yeast strain has the ability to ferment concentrated carbohydrate solutions, has ethanol tolerance and the ability to produce elevated concentrations of ethanol, has a high cell viability for repeated recycling and has temperature tolerance.

Possibly the most important field of use of the new *Saccharomyces cerevisiae*, being able to produce α-amylase and glucoamylase is the production of special beers, preferrably low carbohydrate beers. As already described in the specification above, one technique for producing low carbohydrate beers was to add amylolytic enzymes to the wort during fermentation. Because 70% to 75% of the dextrins in wort are of the branched type, debranching enzyme is essential for total hydrolyses of wort dextrins to fermentable sugars. The glucoamylase, produced by the new genetically manipulated *Saccharomyces cerevisiae* possesses debranching activity and therefore can hydrolyse the dextrins completely. An important characteristic of the amylolytic enzymes produced by the new yeast *Saccharomyces cerevisiae* is their sensitivity to the normal pasteurisation cycle employed in brewing.

The method of preparing beers has a series of stages, starting with malting, where barley is soaked in water and allowed to germinate and during this step amylase is released which converts the starch from the grain into sugar. During the next step, grains are removed by filtration and the resulting liquid wort is brewed with hops. The hops give the beer the bitter flavor and during this step the enzymatic conversion of starch to sugar is stopped. Next, the wort is cooled and filtered to remove the precipitated proteins. Then yeast is added to the wort to convert the sugars to alcohol and carbon dioxide in a fermentation process, after which the mixture is stored, the yeast is settling out, the beer is filtered again, bottled or canned and pasteurised.

In order to produce a low-calorie beer, it is desirable to consume as many of the carbohydrates as possible in the fermentation process. For this purpose the new *Saccharomyces cerevisiae*, being able to produce α-amylase and glucoamylase is highly suitable.

A method for preparing the low-calorie beer can be carried out generally as described in the European Patent Application 0 163 135, with the exception that no amylolytic enzymes have to be added during the brewing process. The above-described usual brewing steps can be carried out without any time-consuming or expensive additions of amylolytic enzymes. Carrying out the brewing process as known in the art, using the new genetically manipulated *Saccharomyces cerevisiae* according to this invention, results in a special beer, preferably low-carbohydrate beer, low-calorie beer depending on the degree of the fermentation of sugar. The brewing process, using the *Saccharomyces cerevisiae* of this invention is decreased in time due to a more rapid decrease in Es at the end of the fermentation process.

Using the *Saccharomyces cerevisiae* of this invention, the manufacturing process can be adapted for the production of a beer from a high gravity wort, the carbohydrate level of which can be regulated by a predetermined fermentation time and dilution thereafter. Furthermore, the manufacturing process may be adapted for the fermention of substrates, the constituent of which are for a considerable part suspended hydrated carbohydrates. The genetically engineered *Saccharomyces cerevisiae* can be brought into contact with the fermented wort subsequently to main fermentation but prior to conditioning.

A more detailed description of the production of a low-calorie beer is now given in the following examples.

EXAMPLE I

Brewer's wort was prepared using conventional brewing techniques in such a way that 80% of the extract in the wort was derived from brewer's malt and 20% derived from corn grits. This wort had an original gravity of 11.7 °P. 3 liter fleakers were filled with 2.5 liters of aerated wort and pitched with 1.5 g/l wet yeast of a genetically manipulated *Saccharomyces cerevisiae* lager brewing strain, which had received by transformation the α-amylase and/or glucoamylase gene (s) from *Schwanniomyces castellii*. Both enzymes were secreted by the transformed yeast strains. As a control the original production lager strain of *Saccharomyces cerevisiae* was used.

Fermentation was allowed to proceed at a controlled temperature of 9° C. under anaerobic conditions and with mechanical stirring due to the small volume of fermentation. At the end of the fermentation, the beer was cooled to 0° C.; yeast was separated from the beer and analysed for residual extract and % ethanol. Also a typical gas chromatogram of the green beer was made to determine the amount of esters and higher alcohols.

Analysis of the green beer fermented with the original lager brewing strain (A), the genetically manipulated brewing lager strain, secreting α-amylase (B) or glucoamylase (C) or both enzymes α-amylase and glucoamylase (D).

| | A | B | C | D |
|---|---|---|---|---|
| original gravity °P. | 11.70 | 11.53 | 11.60 | 11.57 |
| ethanol % w/w | 3.99 | 4.02 | 4.72 | 4.74 |

-continued

|  | A | B | C | D |
|---|---|---|---|---|
| apparent extract °P. | 2.14 | 1.88 | 0.30 | 0.22 |
| apparent degree of fermentation % | 81.7 | 83.7 | 97.4 | 98.1 |
| real extract °P. | 3.96 | 3.71 | 2.43 | 2.36 |
| real degree of fermentation % | 66.2 | 67.8 | 79.0 | 79.6 |
| Gas chromatographic analysis | | | | |
| Acetaldehyde mg/l | 2.0 | 2.1 | 3.1 | 3.9 |
| Acetone mg/l | 0.29 | 0.37 | 0.38 | 0.38 |
| Ethyl formiate mg/l | 0.05 | 0.18 | 0.19 | 0.14 |
| Ethyl acetate mg/l | 20.6 | 21.7 | 33.0 | 39.9 |
| Ethyl propionate mg/l | 0.07 | 0.06 | 0.06 | 0.07 |
| Isoamyl acetate mg/l | 2.45 | 2.21 | 2.95 | 2.92 |
| Methanol mg/l | 2.0 | 2.5 | 2.3 | 2.6 |
| N-propanol mg/l | 17.5 | 16.3 | 21.0 | 17.7 |
| Isobutanol mg/l | 14.2 | 12.6 | 14.7 | 15.3 |
| Opt. act. amylalcohol mg/l | 21.5 | 19.0 | 21.8 | 20.4 |
| Isoamyl alcohol mg/l | 62.5 | 54.2 | 57.6 | 55.1 |
| Total higher alcohols mg/l | 115.7 | 102.1 | 115.1 | 108.5 |

EXAMPLE II

The fermentation process was the same as for Example I except that the fermentation temperature was 13.5° C. After 7 days of fermentation the beer was cooled to 0° C.

Analysis of the green beer fermented with the original lager brewing strain (A), the genetically manipulated brewing lager strain, secreting α-amylase (B) or glucoamylase (C).

|  | A | C |
|---|---|---|
| original gravity °P. | 11.8 | 11.8 |
| ethanol % w/w | 4.10 | 4.60 |
| apparent extract °P. | 2.00 | 0.85 |
| apparent degree of fermentation % | 83.1 | 92.8 |
| real extract °P. | 3.90 | 2.90 |
| real degree of fermentation % | 67.0 | 75.4 |

The analysis of the beers fermented with a genetically manipulated lager brewing strain, secreting α-amylase (B) was hardly different from the control.

EXAMPLE III

The fermentation process was the same as for Example I except that the prepared wort had an original gravity of 15° P. After 9 days of fermentation the beer was cooled to 0° C.

Analysis of the green beer fermented with the original lager brewing strain (A), the genetically manipulated brewing lager strain, secreting α-amylase (B) or glucoamylase (C).

|  | A | C |
|---|---|---|
| original gravity °P. | 15.0 | 15.0 |
| ethanol % w/w | 4.57 | 5.22 |
| apparent extract °P. | 4.30 | 2.76 |
| apparent degree of fermentation % | 71.4 | 81.6 |
| real extract °P. | 6.31 | 5.06 |
| real degree of fermentation % | 58.0 | 66.3 |

The analysis of the beers fermented with a genetically manipulated lager brewing strain, secreting α-amylase (B) was hardly different from the control.

EXAMPLE IV

The fermentation process was the same as for Example I except that the prepared wort had an original gravity of 8.23° P. and the fermentation time/temperature profile was as follows:

4 days 9.5° C., 3 days 13.5° C.

Analysis of the green beer fermented with the original lager brewing strain (A), the genetically manipulated brewing lager strain, secreting α-amylase (B) or glucoamylase (C).

|  | A | C |
|---|---|---|
| original gravity °P. | 8.23 | 8.23 |
| ethanol % w/w | 2.88 | 3.60 |
| apparent extract °P. | 1.16 | −0.56 |
| apparent degree of fermentation % | 85.9 | 107.0 |
| real extract °P. | 2.48 | 1.14 |
| real degree of fermentation % | 69.9 | 86.7 |

The analysis of the beers fermented with a genetically manipulated lager brewing strain, secreting α-amylase (B) was hardly different from the control.

EXAMPLE V

The fermentation process was the same as for Example I except that the prepared wort consisted of 66.7% standard brewers' wort as described in Example I and 33.3% suspended hydrated starch (12% w/v).

Analysis of the green beer fermented with the original lager brewing strain (A), the genetically manipulated brewing lager strain, secreting α-amylase (B) or glucoamylase (C) or both enzymes α-amylase and glucoamylase (D).

|  | A | B | C | D |
|---|---|---|---|---|
| original gravity °P. | 12.01 | 12.14 | 12.13 | 12.22 |
| ethanol % w/w | 2.86 | 4.03 | 4.19 | 4.96 |
| apparent extract °P. | 5.15 | 2.49 | 1.63 | 0.37 |
| apparent degree of fermentation % | 57.1 | 79.5 | 86.6 | 96.9 |
| real extract °P. | 6.47 | 4.32 | 3.62 | 2.61 |
| real degree of fermentation % | 46.2 | 64.4 | 70.2 | 78.6 |
| Gas chromatographic analysis | | | | |
| Acetaldehyde mg/l | 3.9 | 3.4 | 8.4 | 11.6 |
| Acetone mg/l | 0.24 | 0.20 | 0.17 | 0.23 |
| Ethyl formiate mg/l | 0.07 | 0.13 | 0.22 | 0.25 |
| Ethyl acetate mg/l | 8.7 | 20.5 | 39.6 | 43.3 |
| Ethyl propionate mg/l | — | 0.02 | 0.01 | 0.01 |
| Isoamyl acetate mg/l | 0.62 | 1.25 | 1.62 | 1.70 |
| Methanol mg/l | — | — | — | — |
| N-propanol mg/l | 13.6 | 14.9 | 18.3 | 19.7 |
| Isobutanol mg/l | 13.0 | 11.5 | 14.7 | 16.5 |
| Opt. act. amylalcohol mg/l | 10.4 | 12.5 | 20.1 | 18.2 |
| Isoamyl alcohol mg/l | 50.9 | 57.1 | 67.5 | 79.2 |
| Total higher alcohols mg/l | 87.9 | 96.0 | 120.5 | 133.6 |

EXAMPLE VI

Milled grains of wheat and maize were suspended in an appropriate buffer, boiled in order to gelatinaze the starch and liquified by treatment with a commercial α-amylase enzyme preparation.

This broth had an original gravity of 18.9° P. and was fermented in 2.5 liters fermentors at a temperature of 30° C. for 72 hours. The yeast strain used was a *Saccharomyces cerevisiae* distilling strain, which had received by transformation the glucoamylase gene of *Schwanniomyces castellii*. Glucoamylase was secreted by the transformed yeast strain. As a control the same fermentation was carried out with the original untransformed distilling strain. After 72 hours the broth was filtered and the ethanol concentration was determined.

| Yeast | ethanol (% w/w) |
|---|---|
| untransformed distilling strain | 8.9 |
| transformed distilling strain | 9.6. |

REFERENCES

BEIER, D. B. SLEDZIEWSKI, A., YOUNG, E.T. (1985) Mol. Cell. Biol. 5, 1743-1749.

BENOIST, C., O'HARA, K., BREATHNACH, R. and CHAMON; P. (1980): Nuc. Acid. Res. 8, 127-142.

BEGGS, J. D. (1978): Transformation of yeast by a replicating hybrid plasmid. Nature 275, 104-108.

BEGGS, J. D. (1981): In Molecular Genetics in Yeast, Alfred Benzon Symposium 16, 383-395.

BIRNBOIM, H. C. and DOLY, S. (1979): A rapid alkaline extraction procedure for screening recombinant plasmid DNA Nuc. Acid. Res. 7, 1513-1523.

BOLIVAR, S., RODRIGUEZ, R. L., BETLACH, M. C. and BOYER, H. W. (1977): Construction and characterisation of new cloning vehicles. I ampicillin-resistant derivates of the plasmid pMB9. Gene 2, 75-93.

BRADFORD, M. (1976): A rapid and sensitive method for the quantitation of microgram quantities of protein utilizing the principle of protein-dye binding. Anal. Biochem. 77, 248-254.

BREUNIG, K. D., DAHLEMS, U., DAS S., and HOLLENBERG, C. P. (1984) Nucl. Acids Res. 12, 2327-2341.

BUTT, T. R., STERNBERG; E. J., GORMAN, J. A., CLARK; P., HAMER, D., ROSENBERG, M., and CROOKE, S. T. (1984) Proc. Natl. Acad. Sci. USA 81, 3332-3336.

CARBON, J., RATZKIN, B., CLARKE, L. and RICHARDSON, D. (1977): The expression of cloned eucaryotic DNA in procaryotes. Brookhaven Symp. Biol. 29, 277-296.

COHEN, J., GORMAN, J., KOLTIN, Y. and DE WILDE, M. (1985): Molecular cloning of a glucoamylase gene of *Candida albicans*: Expression and secretion in *Saccharomyces cervisiae*. Cold Spring Harbour Symp. Molec. Biol. of Yeasts, 345.

COLLINS, J. and HOHN, B. (1978): Cosmids: A type of plasmid genecloning vector that is packageable in vitro in bacteriophage Lambda heads. Proc. Natl. Acad. Sci. USA 75, 4242-4246:

DAS, S. and HOLLENBERG, C. P. (1982): A high-frequency transformation system for the yeast *Kluyveromyces lactis* Curr. Genet. 6, 123-128.

DAS, S., KELLERMANN, E. and HOLLENBERG, C. P. (1984): Transformation of *Kluyveromyces fragilis*. J. Bacteriol. 158, 1165-1167.

DAVIS, R. W., BOTSTEIN, D. and ROTH, J. F. (1980): Advanced bacterial genetics. A manual for genetic engineering. Cold Spring Harbour Laboratory.

DOBSON, M. J., TUITE, M. F., ROBERTS, N. A., KINGSMAN, A. J., KINGSMAN, S. M., PERKINS; R. E., CONROY, S. C., DUNBAR, B. and FOTHERGILL, L. A. (1982) Nucleic Acids Research 10, 2625-2637.

DUGAICZYK, A., BOYER, H. W. and GOODMAN, H. M. (1975): Ligation of EcoRI endonuclease generated fragments into linear and circular structures. J. Mol. Biol. 96, 171-184.

FEISS, M., FISHER, R. A., CRAYTON, M. A. and EGNER, C. (1977): Packaging of the bacteriophage Lambda chromosome: Effect of chromosome length. Virology 77, 281-293.

FERGUSON, A. R., KATSUNUMA, T., BETZ, H. and HOLZER, H. (1973): Purification and properties of an inhibitor of the tryptophane-synthetase-inactivating enzymes in yeast. Eur. J. Biochem. 32, 444-450.

FOGARTY, W. M. and KELLY, C. T. (1979): Starch degrading enzymes of microbial origin. In: BULL, M. J., (ed): Progress in industrial microbiology. Elsevier Scientific Publishing Company, New York, 15, 87-150.

GAFNER, J., DE ROBERTIS; E. M. and PHILIPPSEN, P. (1983). EMBO J. 2, 583-591.

GANNON, F., O'HARA, K., PERRIN, F., LE PENNEC, J. P., BENOIST, C., COCHET, M., BREATHNACH, R., ROYAL, A., GARAPIN, A. and CHAMBON, P. (1979): Nature 278, 248-434.

HITZEMAN, R. A., HAGIE, F. E., LEVINE, H. L., GOEDEL, D. V., AMMERER, G. and HALL, B. D. (1981): Expression of a human gene for interferon in yeast. Nature 294, 717-722.

HOHN, B. (1985): DNA as substrate for packaging into bacteriophage lambda in vitro. J. Mol. Biol. 98, 93-106.

HOHN, B. (1979): In vitro packaging of Lambda and cosmid DNA. In WU, R. (ed): Recombinant DNA, Methods in Enzymology. Academic Press, New York 68, 299-309.

HOHN, B. and COLLINS, J. (1980): A small cosmid for efficient cloning of large DNA-fragments. Gene 11, 291-298.

HOHN, B. and HINNEN, A. (1980): Cloning with cosmids in *E. coli* and yeast. In SETLOW, J. K. and HOLLAENDER, A. (ed.): Genetic engineering—principles and methods. Plenum Press, New York & London 2, 169-183.

HOLLAND, J. P. and HOLLAND; M. J. (1979) J. Biol. Chem. 254, 5466-5474.

HSIAO, C. L. and CARBON, J. (1981b): Characterisation of a yeast replication origin (ars2) and construction of stable minichromosomes containing cloned centromere DNA (CEN3). Gene 15, 157-166.

INNIS, M. A., HOLLAND, M. J., Mc CABE, P. C., COLE, G. E., WITTMAN, V. P., TAL, R., WATT, K. W. K., GELFAND, D. H., HOLAND, J. P. and MEADE, J. H. (1985): Expression, glycosylation and secretion of an *Aspergillus glucoamylase* by *Saccharomyces cerevisiae*. Science 228, 21-26.

ISH-HOROWICZ, D. and BURKE, J. F. (1981): Rapid and efficient cosmid vector cloning. Nuc. Acids. Res. 9, 2989-2998.

ITO, H., FUKUDA, Y., MURATA, K. and KIMURA, A. (1983): Transformation of intact yeast cells treated with alkali cations. J. Bacteriol. 153, 163-168.

JANOWICZ, Z. A., ECKART, M. R., DREWKE, C., ROGGENKAMP, R. O., HOLLENBERG, C. P., MAAT, J., LEDEBOER, A. M., VISSER; C. and VERRIPS, C. T. (1985) Nucleic Acids Res. 9, 3043-3062.

JOHNSTON, M. and DAVIS, R. W. (1984) Mol. Cell. Biol. 4, 1440-1448.

KARIN, M., NAJARIAN, R., HASLINGER, A., VALENZUELA, P., WELCH, J. and FOGEL, S. (1984) Proc. Natl. Acad. Sci. USA 81, 337–341.

KATSUNUMA, T., SCHÖTT, E., ELSÄSSER, S. and HOLZER, M. (1972): Eur. J. Biochem. 27, 520–526.

KÄUFER, N. F., SIMANIS, V. and NURSE, P. (1985): Fission yeast Schizosaccharomyces pombe exises a mammalian RNA transcript intervening sequence. Nature 318, 78–80.

KLEBE, R. J., HARRISS, J. V., SHARP, Z. D. and DOUGLAS, M. G. (1983): A general method for polyethylene-glycol-induced genetic transformation of bacteria and yeast. Gene 25, 333–341.

KRAMER, W., DRUTSA, V., JANSEN, H.-W., KRAMER, B., PFLUGFELDER, M. and FRITZ, H.-J. (1984) Nucl. Acids. Res. 12, 9441–9456.

LAEMMLI, U. K. (1970): Cleavage of structural proteins during the assembly of the head of bacteriophage T4. Nature 227, 680–685.

LEDEBOER, A. M., MAAT, J., VISSER, C., BOS, J. W., VERRIPS, C. T., JANOWICZ, Z., ECKART, M., DREWKE, C., ROGGENKAMP, R. and HOLLENBERG, C. P., (1985) Nucl. Acids. Res. 9, 3063–3082.

LEPOCK, J. R., KEITH, A. D. and KRUUV, J. (1984): Permeability changes in yeast after freeze, thaw damage; comparison to reproductive survival. Cryo-Letts. 5, 277–280.

LINDENMAIER, W., HAUSER, H., GREISER DE WILKE, I., and SCHÜTZ, G., (1982): Gene shuttling; moving of cloned DNA into and out of eucaryotic cells. Nucl. Acids. Res. 10, 1243–1256.

MANIATIS, T., FRITSCH, E. F. and SAMBROCK, J. (1982): Molecular cloning, a laboratory manual. Cold Spring Harbour Laboratory, New York.

MANNEY, T. R., DUNTZE, W., JANASKO, N. and SALAZAR, J. (1969): Genetic and biochemical studies of partially active tryptophane-synthetase mutants of *Saccharomyces cerevisiae*. J. Bacteriol. 99, 590–596.

MAXAM, S. M. and GILBERT, W. (1980): Sequencing end labelled DNA with base specific chemical cleavages. Methods Enzymol. 65, 499–561.

NUNBERG, J. H., MEADE, J. H., COLE, G., LAWYER, F. C., McCABE, P., SCHWEICKART, V., TAL, R., WITTMAN, V. P., FLATGAARD, J. E. and INNIS, M. A. (1984): Molecular cloning and characterisation of a glucoamylase gene of *Aspergillus awamori*. Mol. Cell. Biol. 4, 2306–2315.

ORR-WEAVER, T. L., SZOSTAK, J. W. and ROTHSTEIN, S. J. (1981): Yeast transformation: A model system for the study of recombination. Proc. Natl. Acad. Sci. USA 78, 6354–6358.

OTENG-GYANG, K., MOULIN, G., GALZY, P. (1981): Zeitschrift allg. Mikrobiol. 21, 537–544.

RIGBY, P. W. J., DIEKMANN, M., RHODES, C. and BERG, P. (1977): Labelling desoxyribonucleic acid to high specific activity in vitro by nick translation with DNA-polymerase I. J. Mol. Biol. 113, 237–251.

ROTHSTEIN, S. J., LAZARUS, C. M., SMITH, W. E., BAULCOMBE, D. C. and GATENBY, A. A. (1984): Secretion of a wheat alpha-amylase expressed in yeast. Nature 308, 662–665.

RUSSELL, D. W. and HALL, B. D., (1983) J. Biol. Chem. 258, 143–149.

RUSSELL, D. W., SMITH, M., WILLIAMSON, V. M. and YOUNG, E. T. (1983) J. Biol. Chem. 258, 2674–2682.

SCHATZ, G. (1979): Meth. Enzymol. L VI, 40–50.

SHERMAN, F., FINK, G. R. and HICKS, J. B. (1983): Methods in yeast genetics. In C. S. H. Laboratory, C. S. H., New York, 119.

SILLS, A. M. and STEWART, G. G. (1982): Production of amylolytic enzymes by several yeast species. J. Inst. Brew. 88, 313–316.

SILLS, A. M., PANCHAL, C. J., RUSELL, I. and STEWART, G. G. (1983 a): Genetic manipulation of amylolytic enzyme production of yeast. Gene Expression in Yeast. Proceedings of the Alko Yeast Symposium Helsinki 1983, ed. by M. Korhola and E. Väisänen. Foundation for Biotechnical and Industrial Fermentation Research 1, 209–228.

SILLS, A. M., RUSELL, I. and STEWART, G. G. (1983 b): The production of yeast amylases in the brewing low carbohydrate beer. EBC Congress, 377–384.

SILLS, A. M., SAUDER, M. E. and STEWART, G. G. (1984 a): Isolation and characterisation of the amylolytic system of *Schwanniomyces castellii*. J. Inst. Brew. 90, 311–314.

SILLS, A. M., ZYGORA, P. S. J. and STEWART, G. G. (1984 b): Characterisation of *Schwanniomyces castellii* mutants with increased productivity of amylases. Appl. Microbiol. Biotechnol. 20, 124–128.

SIMOES-MENDES, B. (1984): Purification and characterisation of the extracellular amylases of the yeast *Schwanniomyces alluvius*. Can. J. Microbiol. 30, 1163–1170.

SOUTHERN, E. M. (1975): Detection of specific sequences among DNA fragments separated by gel electrophoresis. J. Mol. Biol. 98, 503–517.

STRASSER, A. W. M. (1982): Biochemische und biophysikalische Studien an der in Hefe überproduzierten Hefe Tryptophan-synthetase. Dissertation, Universität Basel.

STRUHL, K., STINCHCOMB, D. T., SCHERER, S. and DAVIES R. W. (1979): High-frequency transformation of yeast: Autonomous replication of hybrid DNA molecules. Proc. Natl. Acad. Sci. USA 76, 1035–1039.

THOMSEN, K. K. (1983): Mouse α-amylase synthesised by *Saccharomyces cerevisiae* is released into the culture medium. Carlsberg Res. Commun. 48, 5, 545–555.

TOUCHSTONE, J. C. and DOBBINS, M. F., (1978): Practice of thin layer chromatography. A. Wiley-Interscience publication. John Wiley & Sons.

TSAI, H., TSAI, J. H. J. and YU, P. H. (1973): Effects of yeast proteinase and its inhibitors on the inactivation of tryptophane synthetase from *Saccharomyces cerevisiae* and *Neurospora crassa*. Eur. J. Biochem. 40, 225–232.

WALZ, A., RATZKIN, B. And CARBON, J. (1978): Control of expression cloned yeast (*Saccharomyces cerevisiae*) gene TRP5 by a bacterial insertion element (IS2). Proc. Natl. Acad. Sci. USA 75, 6172–6176.

WILSON, J. J. and INGLEDEW, W. M. (1982): Isolation and characterisation of *Schwanniomyces alluvius* amylolytic enzymes. Appl. Environ. Microbiol. 44, 301–307.

YAMASHITA, I. and FUKUI, S. (1983): Molecular cloning of glucoamylase-producing gene in the yeast Saccharomyces. Agric. Biol. Chem. 47, 2689–2692.

ZALKIN, H. and YANOFSKY, C. (1982): Yeast gene TRP5: Structure, function, regulation. J. Biol. Chem. 257, 1491-1500.

We claim:

1. In a process for the production of ethanol, or of a fermented food or beverage, which comprises cultivating a Saccharomyces yeast culture in a suitable culture medium, the improvement comprising the use of a recombinant Saccharomyces yeast culture expressing a Schwanniomyces glucoamylase or alpha-amylase enzyme, said culture medium comprising fermentable material, at least a portion of which is fermentable by said Schwanniomyces enzyme but not by wild-type Saccharomyces amylolytic enzymes, under conditions favoring fermentation of said material.

2. The process of claim 1 wherein the food or beverage produced is an alcoholic beverage.

3. The process of claim 2 wherein the alcoholic beverage is a beer.

4. The process of claim 2 wherein the food or beverage is a bread.

5. The process of claim 1, wherein the yeast culture is the sole source of any amylolytic enzymes used in the process.

6. The process of claim 1 in which the yeast culture produces both an alpha amylase and a glucoamylase.

7. The process of claim 3 in which the glucoamylase has debranching activity, and the yeast culture is capable of totally hydrolyzing wort dextrins to fermentable sugars.

8. The process of claim 2 in which the amyloltic enzyme is sensitive to pasteurization conditions employed in brewing.

9. The process of claim 2, wherein the beverage is a low carbohydrate beer.

10. The process of claim 1 in which the fermentable material comprises branched dextrins.

11. The process of claim 1 in which the fermentable material comprises suspended hydrated carbohydrates.

12. The process of claim 2 in which the manufacturing process is adapted for the production of beers containing levels of aroma components comparable to beers obtained by fermentation of high glucose worts.

13. The process of claim 2 in which the process is decreased in duration as a result of the improvement due to a more rapid decrease in apparent extract at the end of the fermentation process.

14. The process of claim 2 in which the manufacturing process is adapted for the production of a beer from a high gravity wort, the carbohydrate level of which can be regulated by a predetermined fermentation time and dilution thereafter.

* * * * *